United States Patent
Bell et al.

(10) Patent No.: US 10,531,828 B2
(45) Date of Patent: Jan. 14, 2020

(54) METHOD AND SYSTEM FOR TRANSCRANIAL PHOTOACOUSTIC IMAGING FOR GUIDING SKULL BASE SURGERIES

(71) Applicant: THE JOHNS HOPKINS UNIVERSITY, Baltimore, MD (US)

(72) Inventors: Muyinatu Bell, Towson, MD (US); Emad Boctor, Baltimore, MD (US); Peter Kazanzides, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 706 days.

(21) Appl. No.: 14/611,628

(22) Filed: Feb. 2, 2015

(65) Prior Publication Data
US 2015/0223903 A1    Aug. 13, 2015

Related U.S. Application Data

(60) Provisional application No. 61/934,253, filed on Jan. 31, 2014.

(51) Int. Cl.
*A61B 5/00* (2006.01)
*A61B 8/08* (2006.01)
(Continued)

(52) U.S. Cl.
CPC ............ *A61B 5/489* (2013.01); *A61B 5/0095* (2013.01); *A61B 5/065* (2013.01); *A61B 5/6868* (2013.01);
(Continued)

(58) Field of Classification Search
None
See application file for complete search history.

(56) References Cited

U.S. PATENT DOCUMENTS

2009/0137952 A1* 5/2009 Ramamurthy ............ A61B 5/06
  604/95.01
2011/0021924 A1* 1/2011 Sethuraman ......... A61B 5/0095
  600/463
(Continued)

OTHER PUBLICATIONS

Lediju ("Short-Lag Spatial Coherence of Backscattered Echoes: Imaging Characteristics" IEEE Transactions on Ultrasonics, Ferroelectrics, and Frequency Control, vol. 58, No. 7, Jul. 2011).*
Park et al., "Adaptive Beamforming for Photoacoustic Imaging Using Linear Array Transducer", IEEE International Ultrasonics Symposium Proceedings. 2008. pp. 1088-1091 (Year: 2008).*
Lediju Bell et al (2013) Short-lag spatial coherence beamforming of photoacoustic images for enhanced visualization of prostate brachytherapy seeds. Biomed Opt Express. Sep. 4, 2013;4(10):1964-77. doi: 10.1364/BOE.4.001964. eCollection 2013.
(Continued)

*Primary Examiner* — Bill Thomson
*Assistant Examiner* — Farouk A Bruce
(74) *Attorney, Agent, or Firm* — Harrity & Harrity, LLP

(57) ABSTRACT

The present invention is directed to a method and system for photoacoustic imaging for guiding medical procedures. A transducer is placed near the site of the procedure. The optical fiber, coupled to an electromagnetic source, such as a laser, is attached to a medical device. During the procedure, the device and optical fiber are inserted into the procedure site where the optical fiber illuminates the procedure site, which has a thickness of approximately 2 mm. Photoacoustic images are acquired to visualize the procedure site as the procedure is proceeding in order to provide real-time guidance. This system is applicable to multiple surgical and interventional procedures, such as transsphenoidal surgery.

21 Claims, 43 Drawing Sheets

(51) Int. Cl.
*A61B 5/06* (2006.01)
*A61B 34/20* (2016.01)
*A61B 34/30* (2016.01)
*A61B 90/00* (2016.01)
*A61B 17/34* (2006.01)
*A61B 17/00* (2006.01)
*A61B 90/30* (2016.01)

(52) U.S. Cl.
CPC ............ *A61B 8/0841* (2013.01); *A61B 34/20* (2016.02); *A61B 34/30* (2016.02); *A61B 90/37* (2016.02); *A61B 2017/00725* (2013.01); *A61B 2017/345* (2013.01); *A61B 2034/2055* (2016.02); *A61B 2090/306* (2016.02); *A61B 2090/363* (2016.02); *A61B 2090/372* (2016.02); *A61B 2090/378* (2016.02); *A61B 2505/05* (2013.01); *Y10S 901/41* (2013.01)

(56) References Cited

U.S. PATENT DOCUMENTS

2012/0253180 A1* 10/2012 Emelianov .......... A61B 8/0841
600/424
2014/0121505 A1* 5/2014 Irisawa ................ A61B 5/0095
600/424

OTHER PUBLICATIONS

Jin et al (2008) Effects of acoustic heterogeneities on transcranial brain imaging with microwave-induced thermoacoustic tomography. Med Phys. Jul. 2008;35(7):3205-14.
Wang et al (2007) Noninvasive reflection mode photoacoustic imaging through infant skull toward imaging of neonatal brains. J Neurosci Methods. Mar. 15, 2008;168(2):412-21. Epub Nov. 21, 2007.

* cited by examiner

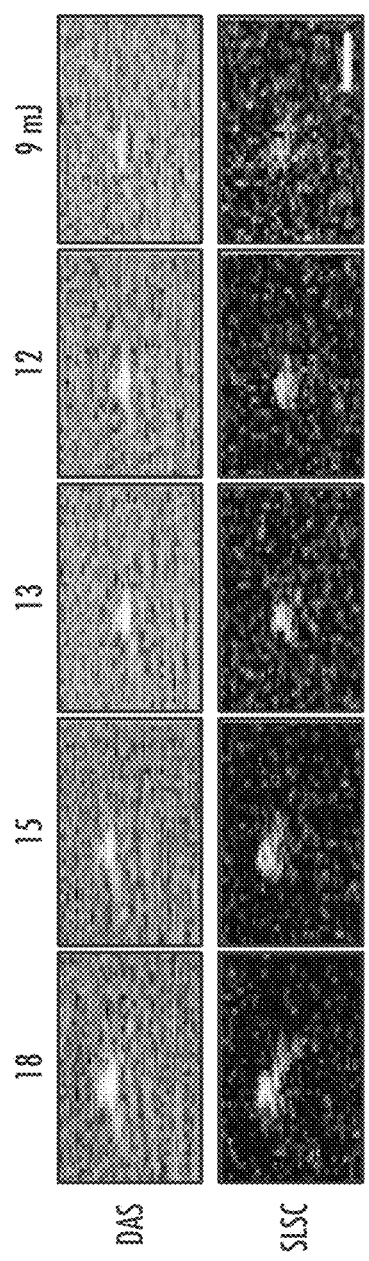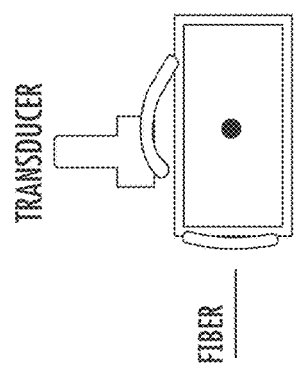
FIG. 7

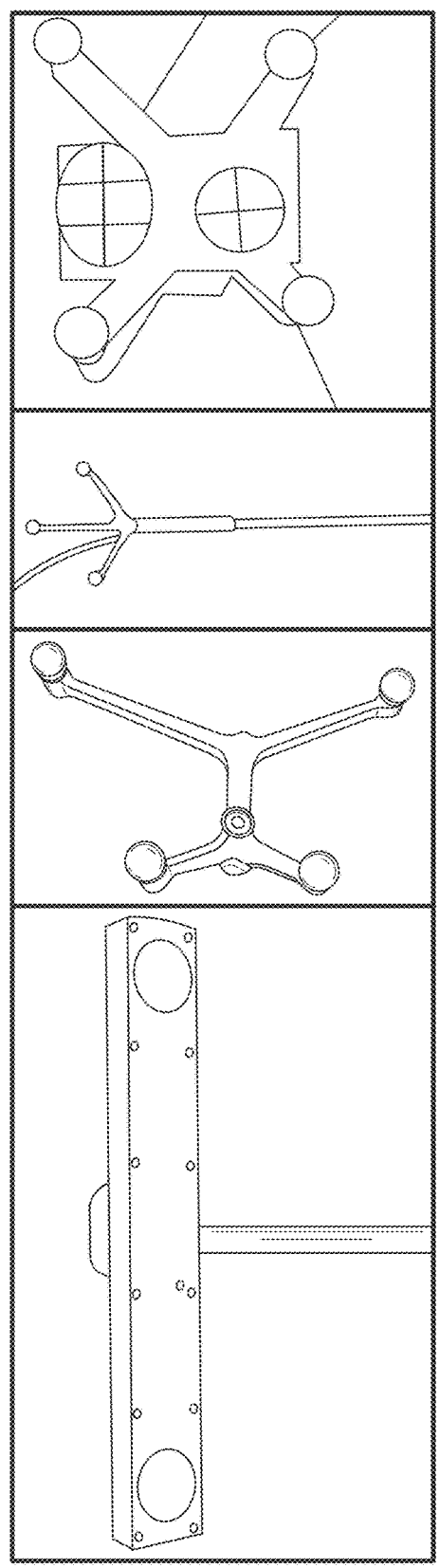

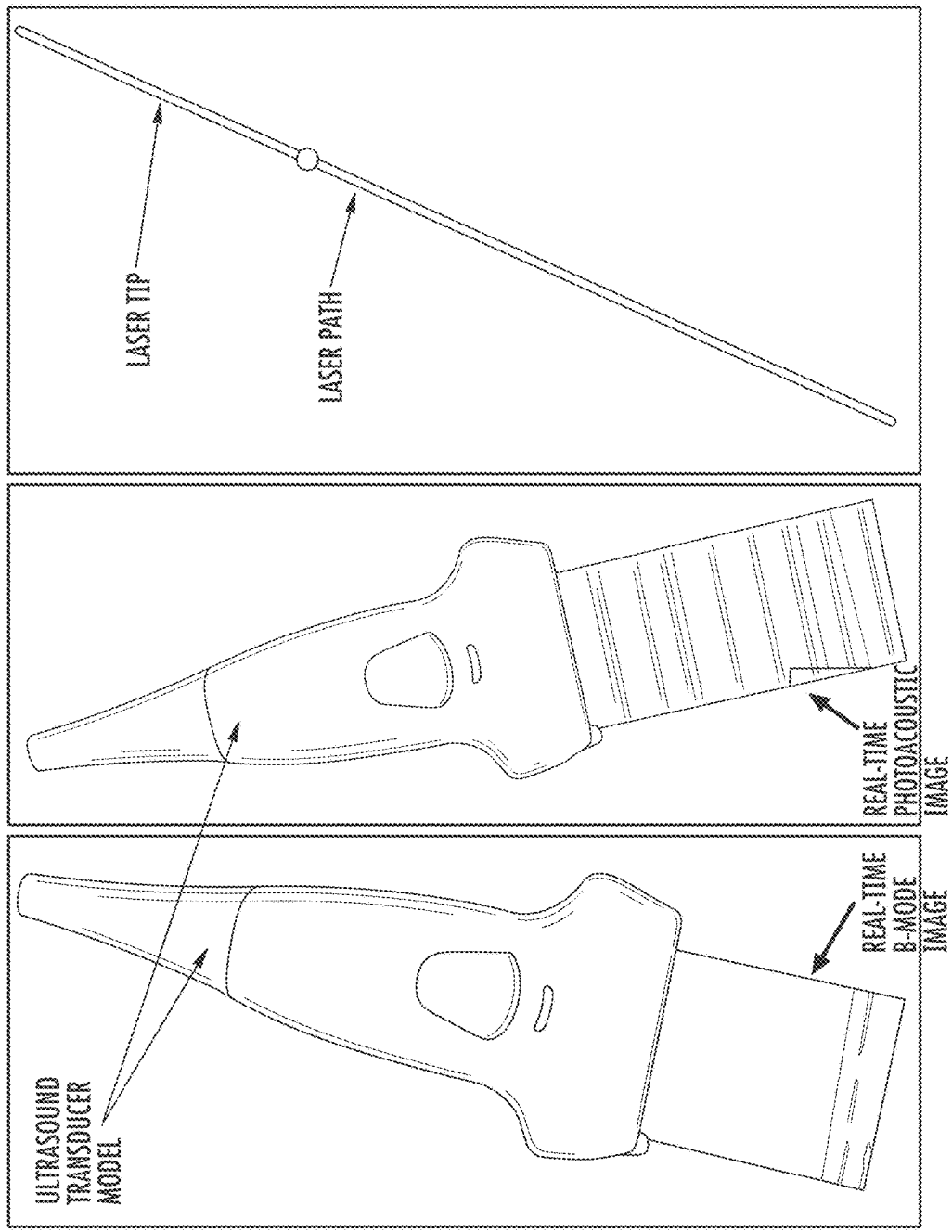

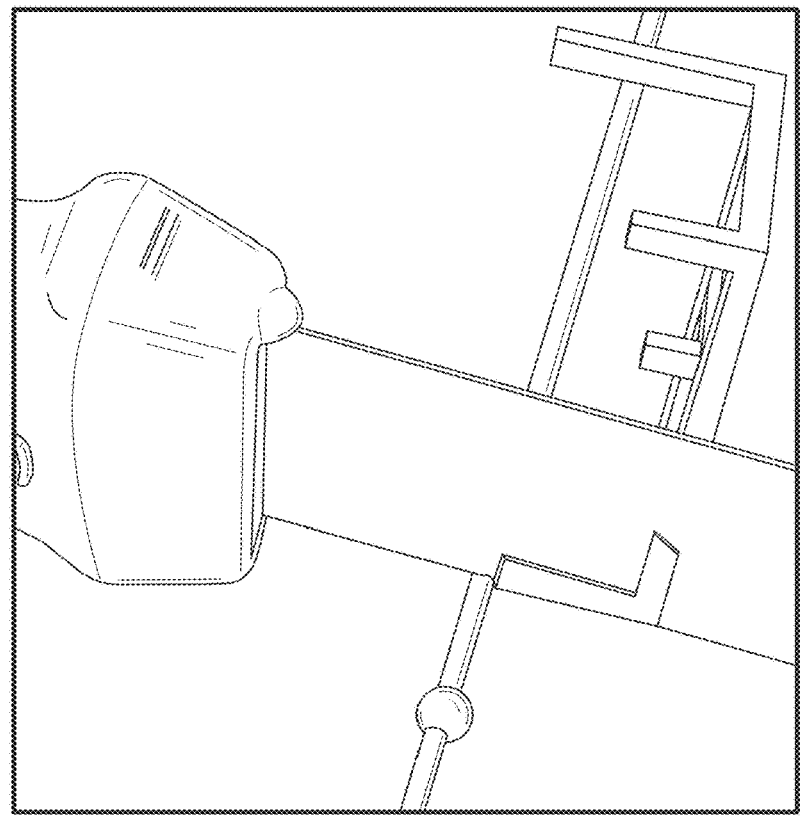
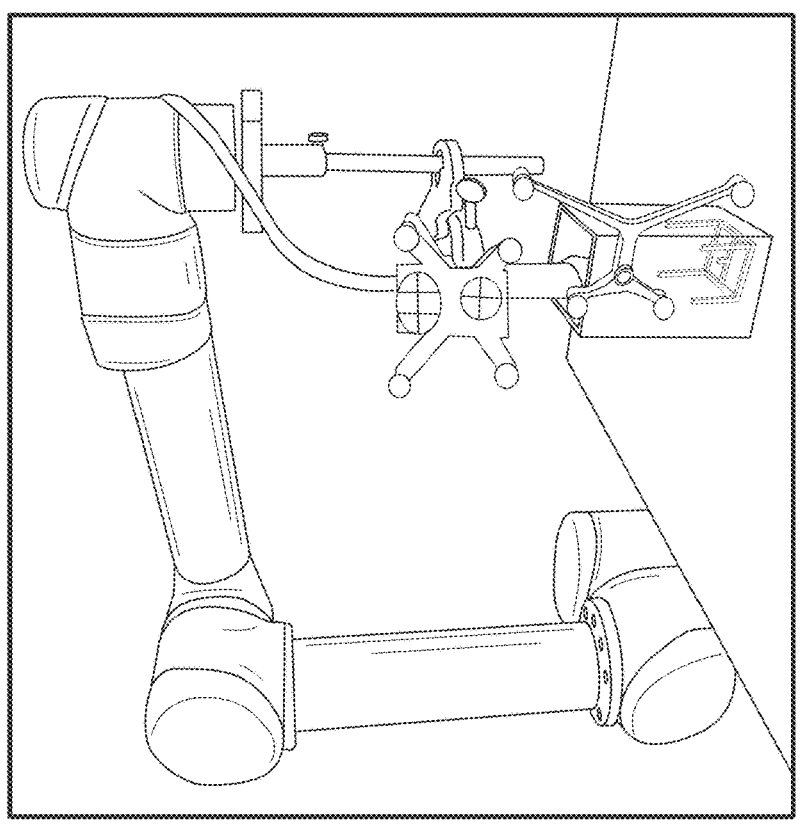
FIG. 33B
FIG. 33A

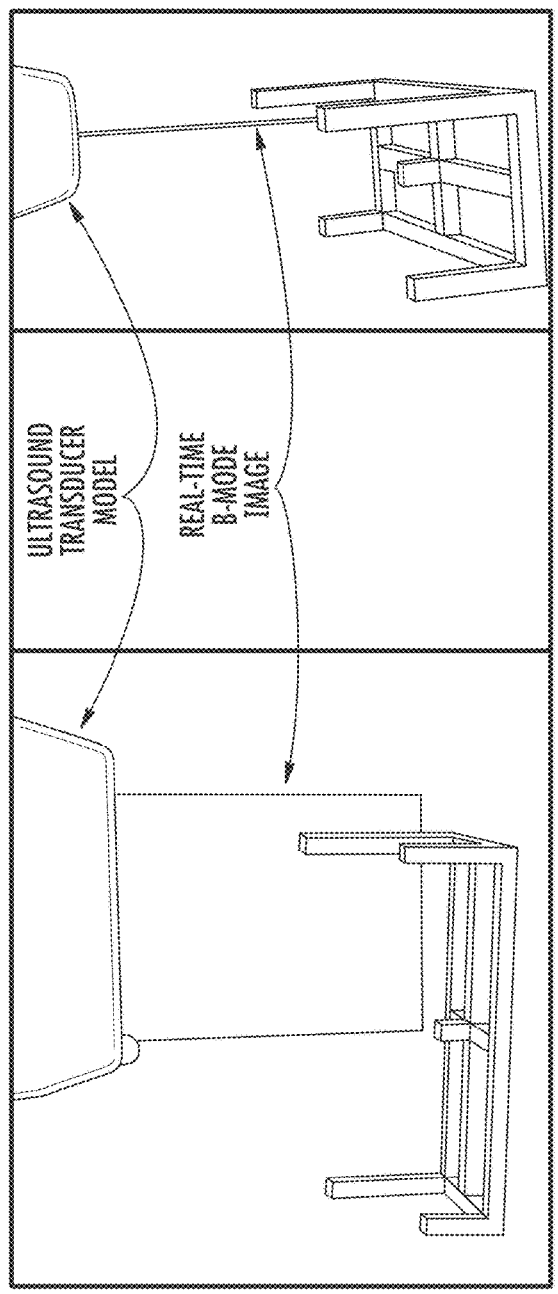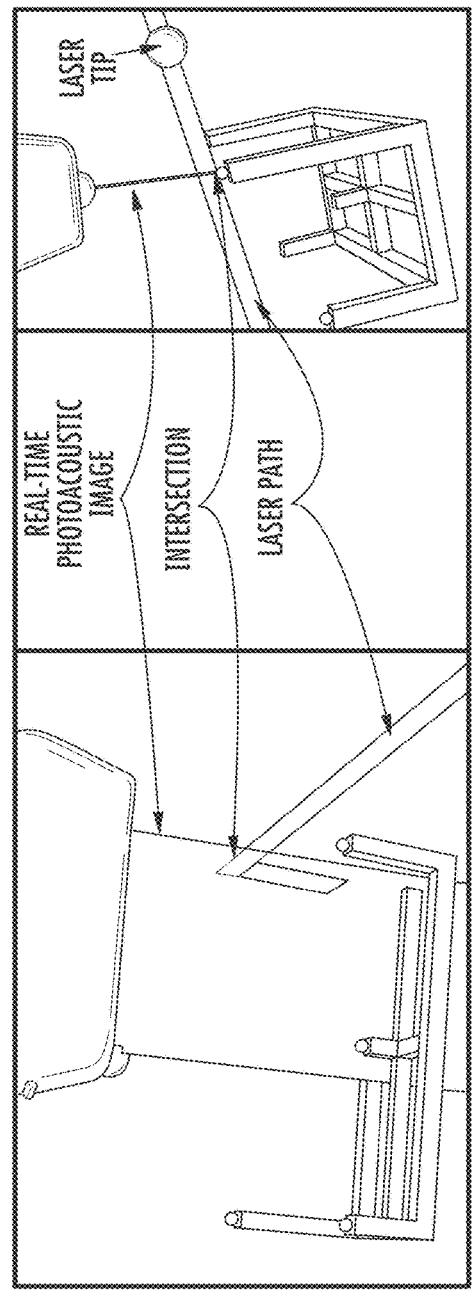
FIG. 34A
FIG. 34B

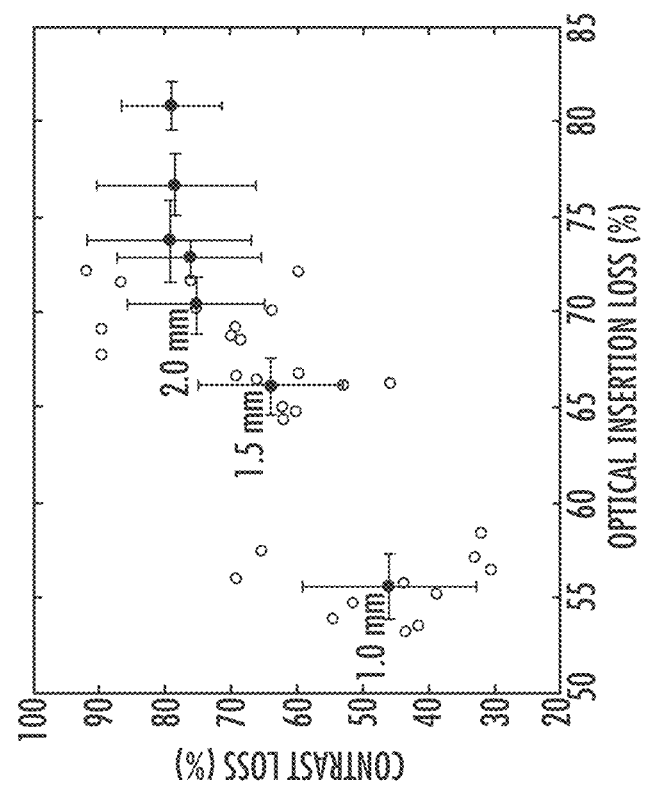
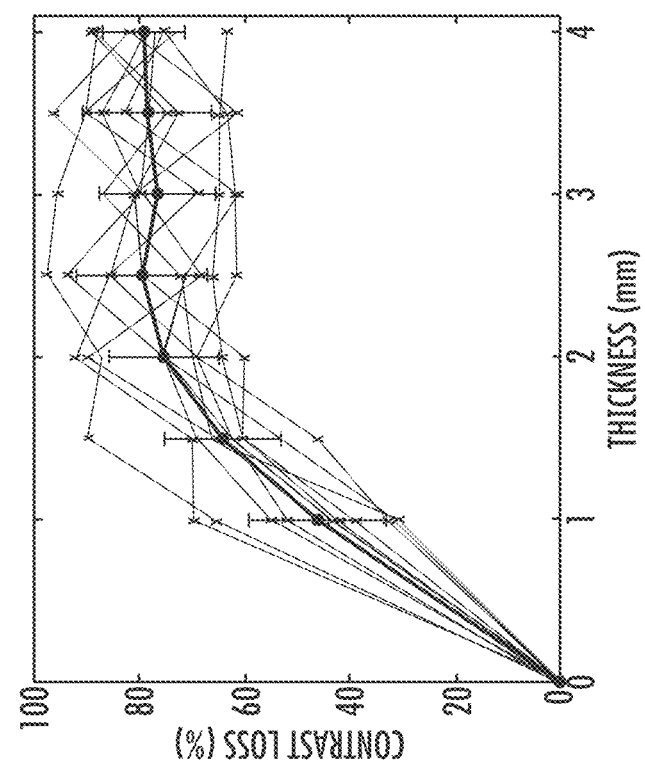
FIG. 41A
FIG. 41B

METHOD AND SYSTEM FOR TRANSCRANIAL PHOTOACOUSTIC IMAGING FOR GUIDING SKULL BASE SURGERIES

CROSS REFERENCE TO RELATED APPLICATION

This application claims the benefit of U.S. Provisional Patent Application No. 61/934,253 filed on Jan. 31, 2014, which is incorporated by reference, herein, in its entirety.

GOVERNMENT SUPPORT

This invention was made with government support under grant number NRI1208540 awarded by the National Science Foundation. The government has certain rights in the invention.

FIELD OF THE INVENTION

The present invention relates generally to imaging. More particularly, the present invention relates to a method and system for medical imaging for use in guiding skull base surgeries.

BACKGROUND OF THE INVENTION

Approximately 8,000 pituitary tumors are diagnosed each year in the United States, causing a variety of hormonal complications, compressing critical nerves and arteries at the base of the brain, and creating a potential for vision loss. Transsphenoidal surgery is the most common method for removal of pituitary tumors to reverse endocrine problems and restore normal hormone balance. This is a minimally-invasive procedure in which instruments such as a drill for sphenoidal bone removal and a curette for tumor resection are passed through the nostrils and nasal septum to access the sphenoid sinus and resect the tumor. In endoscopic endonasal transsphenoidal surgery, an endoscope is inserted through an incision at the rear of the nasal septum, for visualization of the surgical field, as depicted in FIG. 1.

Injury to the carotid arteries, which are located behind the sphenoid on either side of the pea-sized pituitary gland, is a significant complication of transsphenoidal surgery that causes severe blood loss, stroke, or death. It may be treated with emergency interventions, albeit with a high risk of irreversible neurological damage. This complication occurs most frequently with novice surgeons who have performed fewer than 200-500 of these surgeries and thus are not sufficiently familiar with potential variations in the anatomy surrounding the pituitary gland. In addition, this procedure is particularly challenging in pediatric patients who are born with small nasal cavities that mainly develop into their full size after puberty. Approximately 75% of hospitals in the country treat 2-25 cases annually, excluding high-volume institutions like the Johns Hopkins Hospital (a pioneering institution of transsphenoidal surgeries), where neurosurgeons treat 100-150 cases per year. Thus, there are generally limited opportunities for novice surgeons to gain necessary caseload experience.

The availability of imaging methods for localizing blood vessels during endonasal surgery would assist with reducing the occurrence of carotid artery injury. Intraoperative CT may be used for guidance of the bony anatomy surrounding the pituitary tumor, however, it does a poor job of visualizing blood vessels and incurs the risks associated with radiation exposure. Magnetic resonance angiography is another option, but it is costly and patients with pacemakers or metal implants are not suitable candidates for this approach. In addition, these imaging modalities are not quite real-time as one volumetric reconstruction could take as long as 20 minutes. Transcranial ultrasound is a potential option, but it requires low transmit frequencies for skull penetration, which translates to poor spatial resolution and a necessity for expert sonographers to interpret images.

Real-time photoacoustic imaging is a faster, safer, less expensive option which generates images by emitting nanosecond light pulses from a laser. When the light irradiates a target, such as bone or vessels, the target absorbs the light, according to its optical absorption spectrum. Optical absorption causes thermoelastic expansion and generates acoustic waves that are detectable with an ultrasound transducer. Photoacoustic imaging is advantageous over conventional ultrasound imaging because there is less acoustic interaction with the skull. The acoustic waves are only required to pass through the skull one time, rather than twice as in pulse-echo ultrasound and as a result, the waves are less susceptible to the sound scattering and aberrations that occur when they encounter the skull.

One challenge with conventional photoacoustic imaging methods is the diminishing light penetration, signal-to-noise ratios, and signal contrast as local laser fluence decreases. This is particularly challenging for transcranial photoacoustic imaging, given the expected poor signal-to-noise ratios due to light obstruction and sound scattering caused by the presence of sphenoidal and temporal bones, respectively.

It would therefore be advantageous to provide a safe, effective method and system for transcranial photoacoustic imaging.

SUMMARY OF THE INVENTION

The foregoing needs are met by the present invention which provides a system for photoacoustic imaging during a surgical procedure including an ultrasonic transducer positioned at or near a site of the surgical procedure. The system also includes a laser configured to produce ultrasonic waves. Additionally, the system includes an optical fiber coupled to the laser, such that the optical fiber illuminates the site of the surgical procedure with the ultrasonic waves. The definition of surgery includes but is not limited to any interventional procedure that would benefit from blood vessel (and/or other target) visualization (e.g. transcranial surgery, pancreatic surgery, establishing intravaneous access for chemotherapy—particularly in cases where veins are not close to the surface, biopsies, laporoscopic surgery).

In accordance with an aspect of the present invention, the system includes a non-transitory computer readable medium configured to receive image data and configured to process image data. The non-transitory computer readable medium is programmed to execute coherence-based beamforming to correct for insufficient laser fluence. The system is configured for use in a transsphenoidal surgery and/or for use in detecting blood vessels during surgery or any interventional procedure.

In accordance with an aspect of the present invention, a system for photoacoustic imaging during any surgical or interventional procedure includes an acoustic sensor positioned at or near a site of the surgical procedure. The system includes an electromagnetic source such as a laser configured to produce electromagnetic or ultrasonic waves. The system also includes an optical fiber coupled to the laser, such that the optical fiber irradiates or illuminates the site of the surgical procedure with electromagnetic waves.

In accordance with another aspect of the present invention, the system includes a non-transitory computer readable medium configured to receive image data and configured to process image data. The non-transitory computer readable medium is configured to process the image data with beamforming. The non-transitory computer readable medium is programmed to execute coherence-based beamforming to correct for insufficient laser fluence. The non-transitory computer readable medium is further configured to receive data from the optical fiber. The non-transitory computer readable medium is further configured to process the data from the optical fiber with the image data. The system can be configured for use in a transsphenoidal surgery and other interventional procedures. The system can be configured for use in detecting blood vessels during surgery and other interventional procedures. The system can further include a robot to control one or more of a surgical tool, the optical fiber, or the ultrasound probe. The robot is controlled by the non-transitory computer readable medium. The ultrasound transducer is configured to acquire B-mode images.

In accordance with yet another aspect of the present invention, a system for photoacoustic imaging includes a tracking module comprising an optical fiber, a medical device, and a laser wherein the tracking module generates tracking data. The system includes a photoacoustic module, wherein the photoacoustic module is configured to generate image data. The system also includes a computing module comprising a non-transitory computer readable medium wherein the non-transitory computer readable medium is programmed to process the tracking data and the image data using coherence-based beamforming (e.g. short-lag spatial coherence (SLSC)).

In accordance with another aspect of the present invention, the medical device further takes the form of a surgical tool. The ultrasound transducer is configured to acquire B-mode images. The ultrasound transducer is also configured to acquire photoacoustic images. The system can be configured for use in a transsphenoidal surgery. The system is also configurable for use in detecting blood vessels during surgery or any interventional procedure. A robot can be used to control one or more of the medical device, the ultrasound probe, and the optical fiber. The robot is coupled to the medical device, optical fiber, and/or the ultrasound probe. The non-transitory computer readable medium is programmed to provide control of the robot. A second non-transitory computer readable medium is programmed to provide control of the robot. The system can include image quality/performance metrics used to ascertain information for guiding surgical procedures. The photoacoustic module can take the form of at least one selected from a group of an ultrasound transducer and a photoacoustic module optical fiber. The photoacoustic module optical fiber can in some embodiments also the optical fiber of the tracking module. The optical fiber can be coupled to one or more of the medical device and the laser. The tracking module can be coupled to the photoacoustic module.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 7 illustrates DAS vs. SLSC beamforming, for the experimental setup shown, as energy at the tip of the fiber is varied. The white line, 5 mm in length indicates image scale. All images are shown with 25 dB dynamic range.

vessel boundaries as the fiber was translated by an axial distance noted above each figure.

Figure 23A:
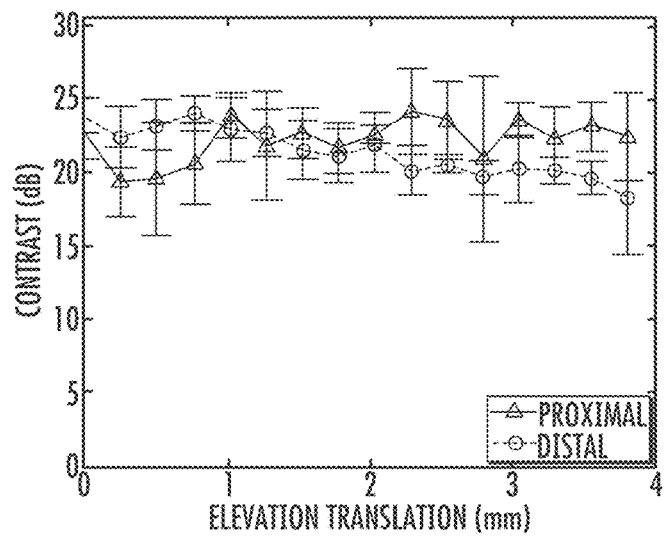
Figure 23B:
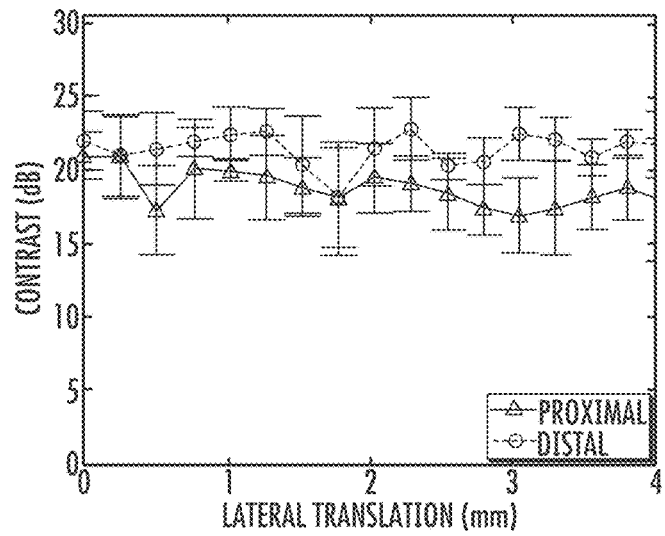
Figure 23C:
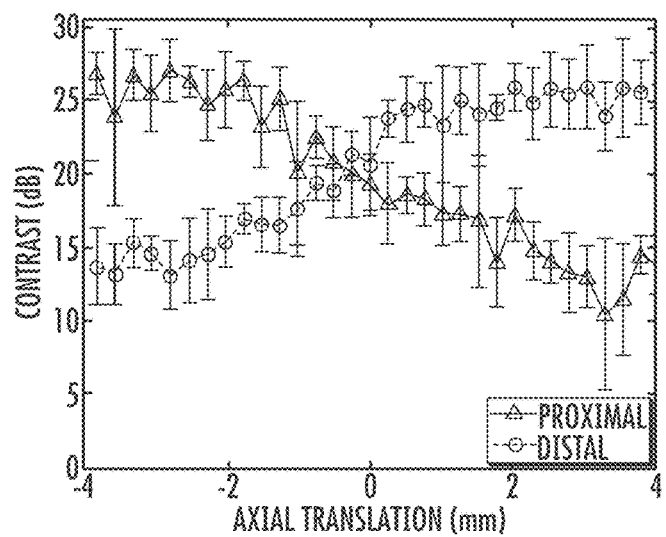

FIGS. 23A-23C illustrate graphical views of mean contrast as a function of fiber translation in the axial (FIG. 23A), elevation (FIG. 23B), and lateral probe dimensions (FIG. 23C).

Figure 24:
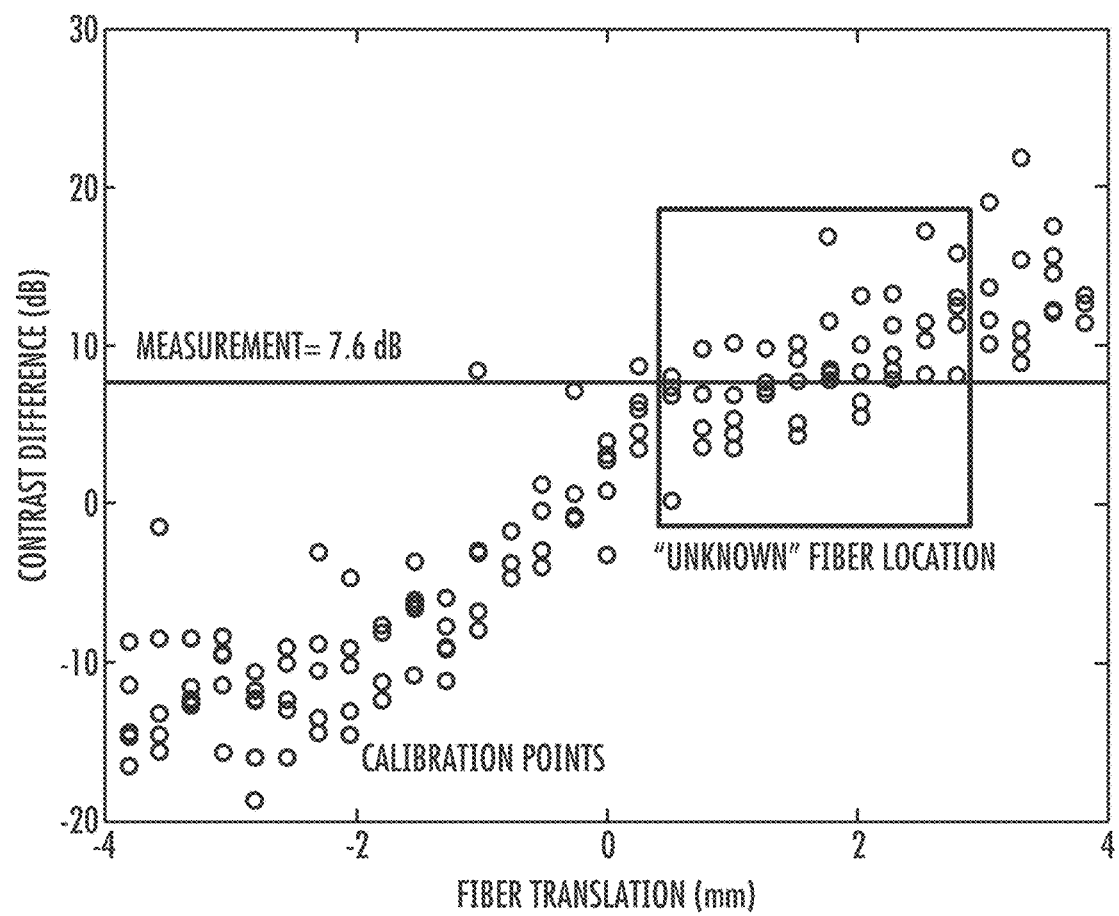

FIG. 24 illustrates a graphical view of calibration points shown along with one measurement from the test set along with the "unknown" fiber position that was estimated and compared with the ground truth location illustrated in the plot.

Figure 25:
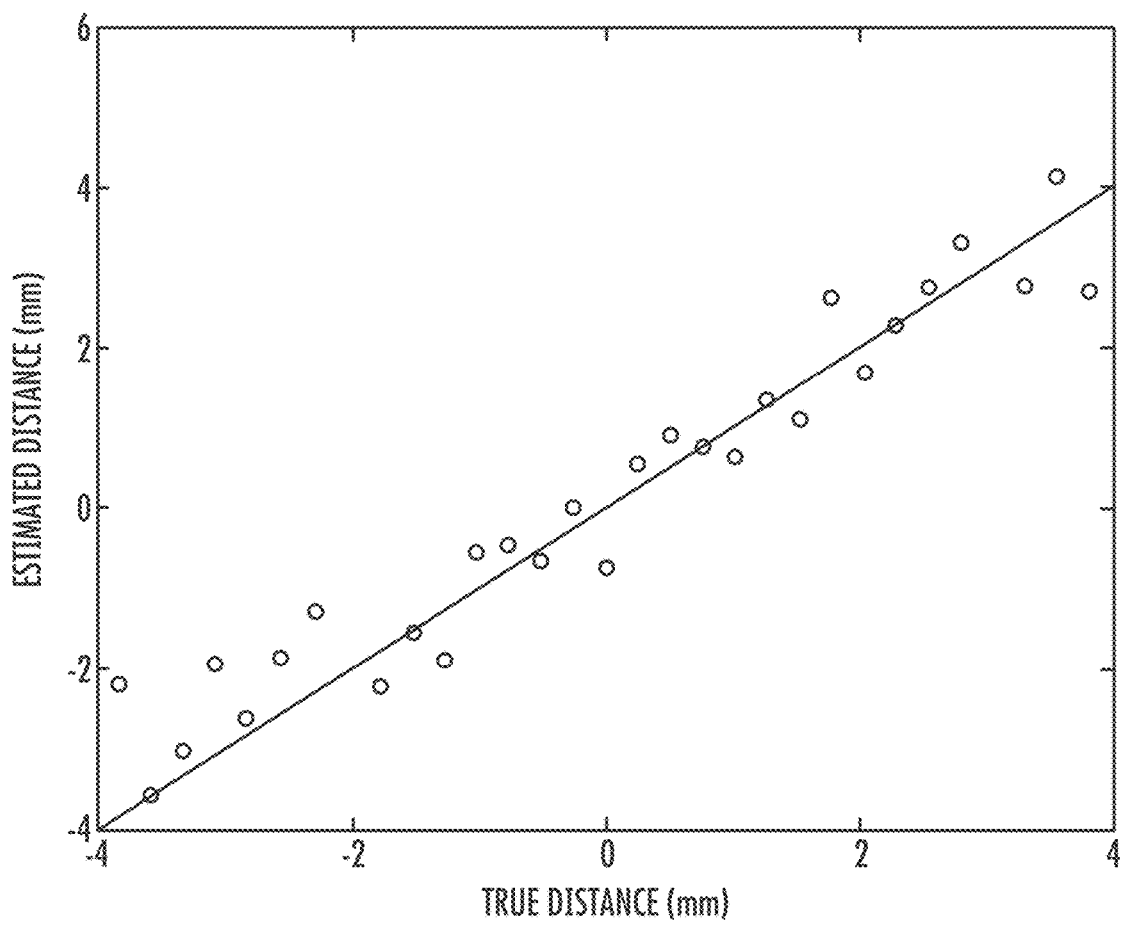

FIG. 25 illustrates a graphical view of estimated versus true distance for thirty fiber positions with the diagonal line indicating the ideal 1:1 relationship.

Figure 26:
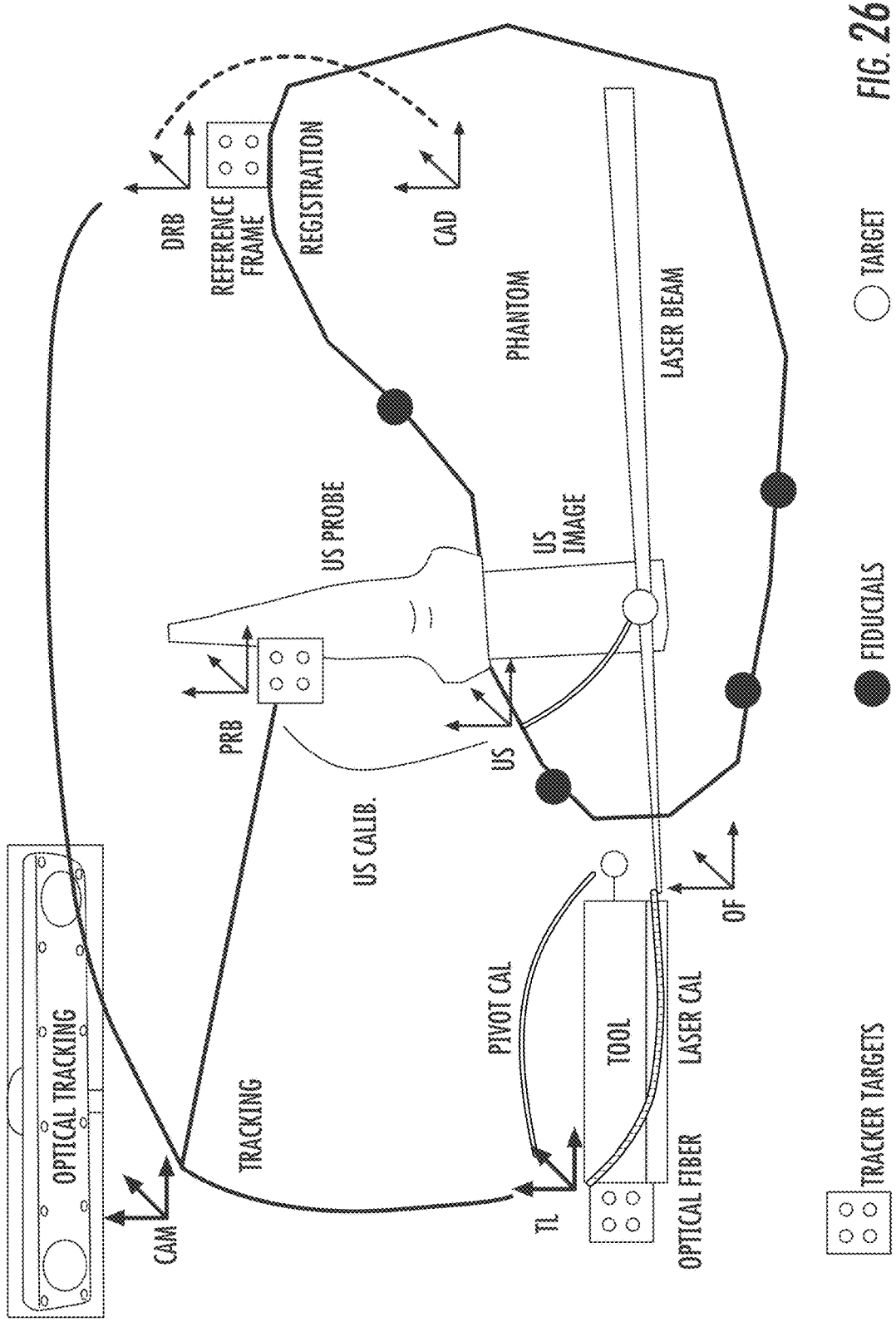

FIG. 26 illustrates a schematic diagram of major components, coordinate frames and transformations for an implementation of a navigational and photoacoustic system, according to an embodiment of the present invention.

Figure 27:
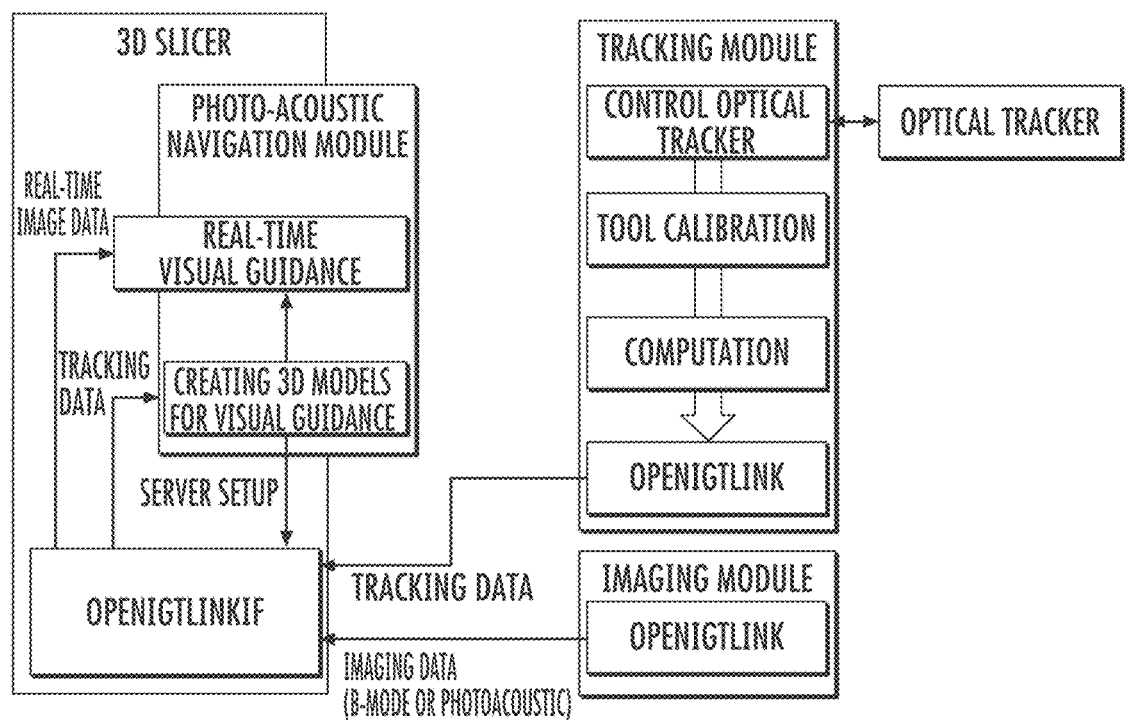

FIG. 27 illustrates a graphical view of a system overview for an assistant system for photoacoustic imaging.

FIGS. 28A-28D illustrate images of optical tracker and tracking tools (FIG. 28A Optical Tracker, FIG. 28B Dynamic Reference Base attached to the phantom, FIG. 28C optical fiber holder, FIG. 28D marker frame attached to the ultrasound transducer).

FIGS. 29A and 29B illustrate a perspective view of an ultrasound probe model and real time ultrasound imaging; FIG. 29C illustrates a schematic diagram of a laser tip and virtual laser path.

Figure 30A:
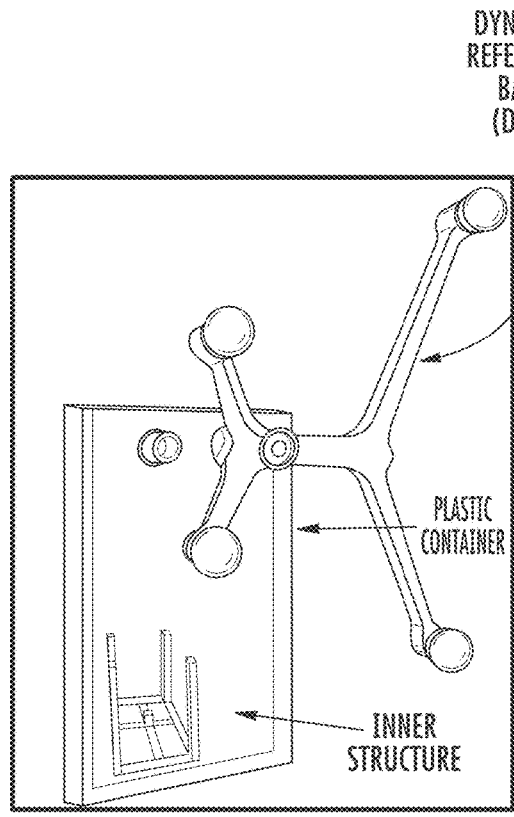
Figure 30C:
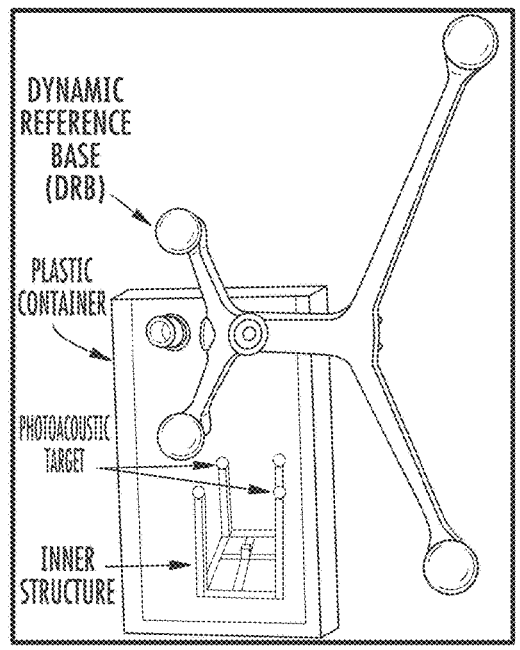
Figure 30B:
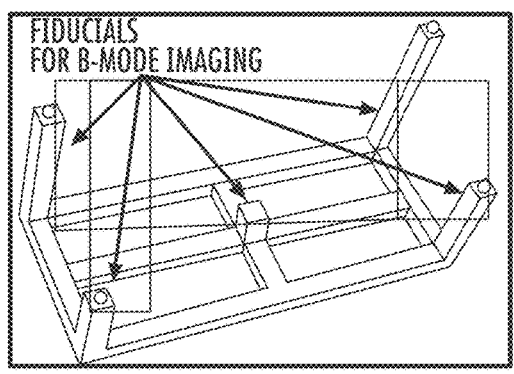
Figure 30D:
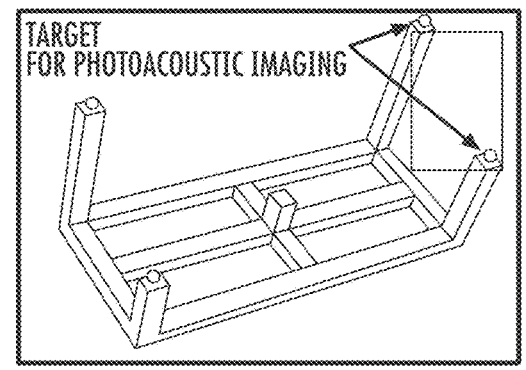

FIG. 30A illustrates a phantom embedded with an inner structure for B-mode imaging. FIG. 30B illustrates a CAD model of the inner structure of the device of FIG. 30A. FIG. 30C illustrates the phantom of FIG. 30A embedded with additional spherical rubber targets, and FIG. 30D illustrates a CAD model of the inner structure of FIG. 30C.

Figure 31:
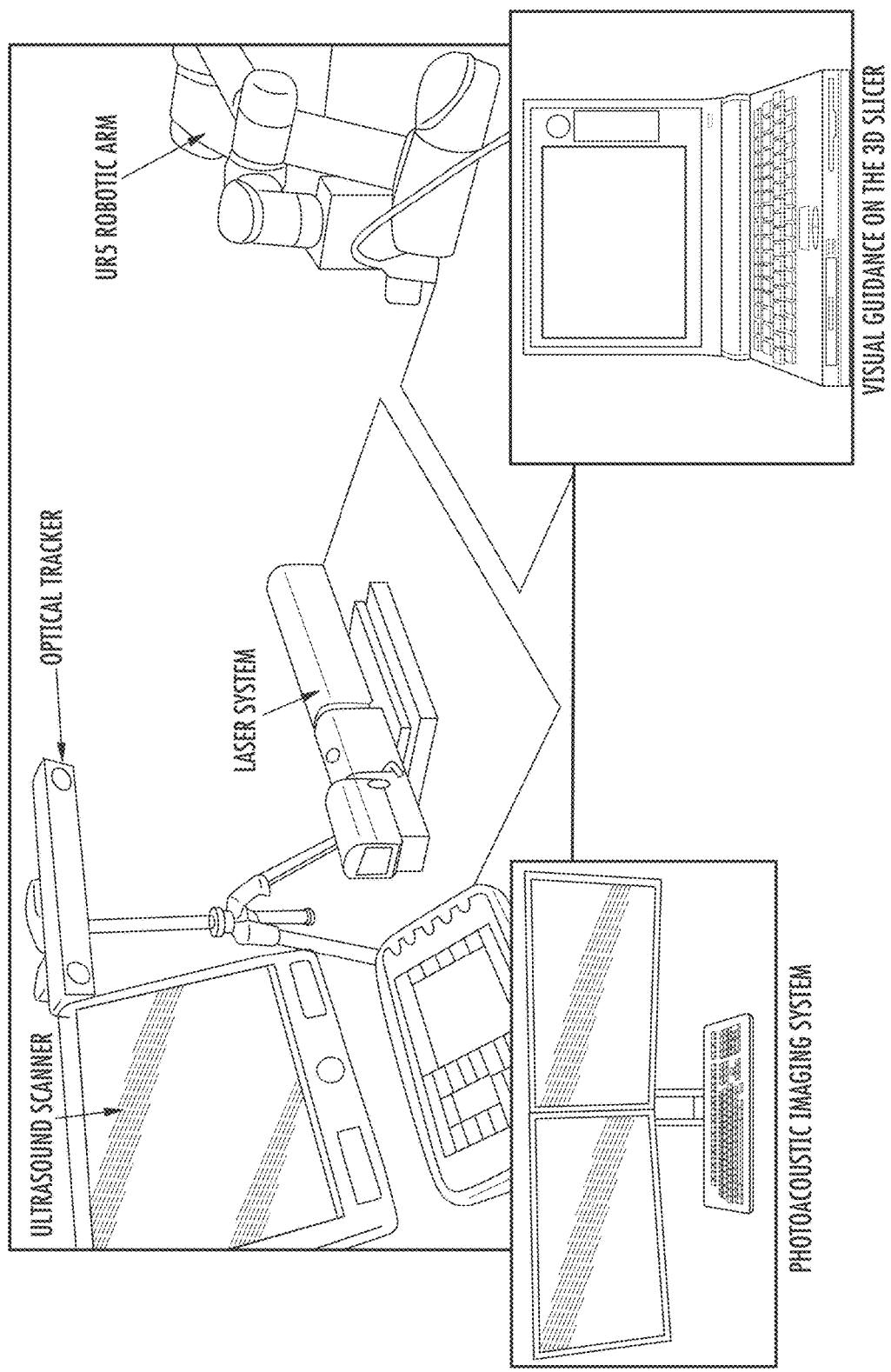

FIG. 31 illustrates images of an experimental setup according to the exemplary embodiment of the invention.

Figure 32A:
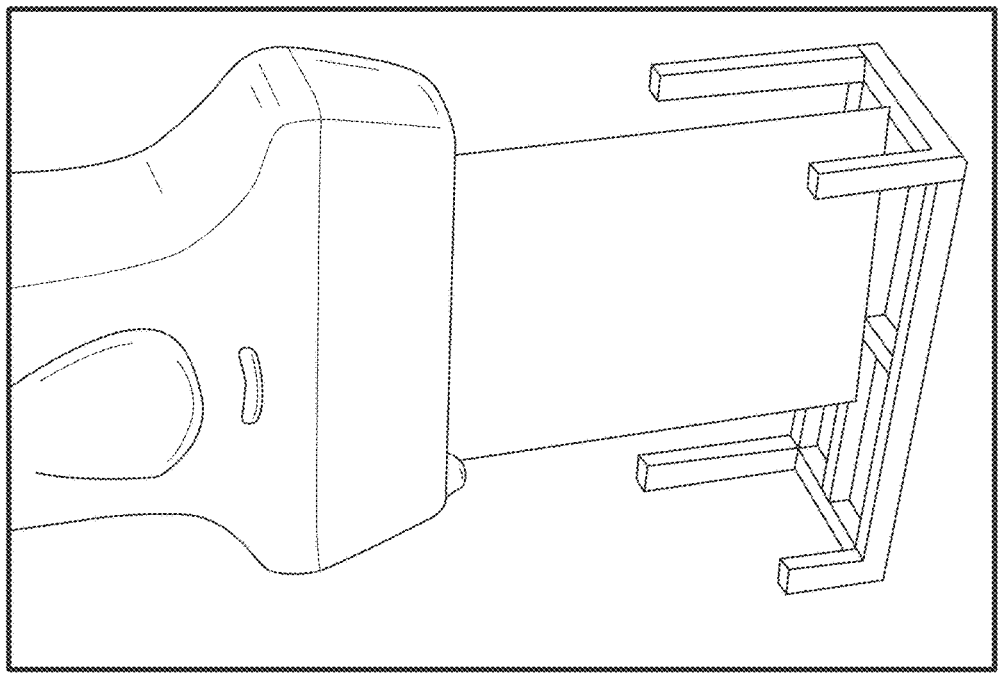
Figure 32B:
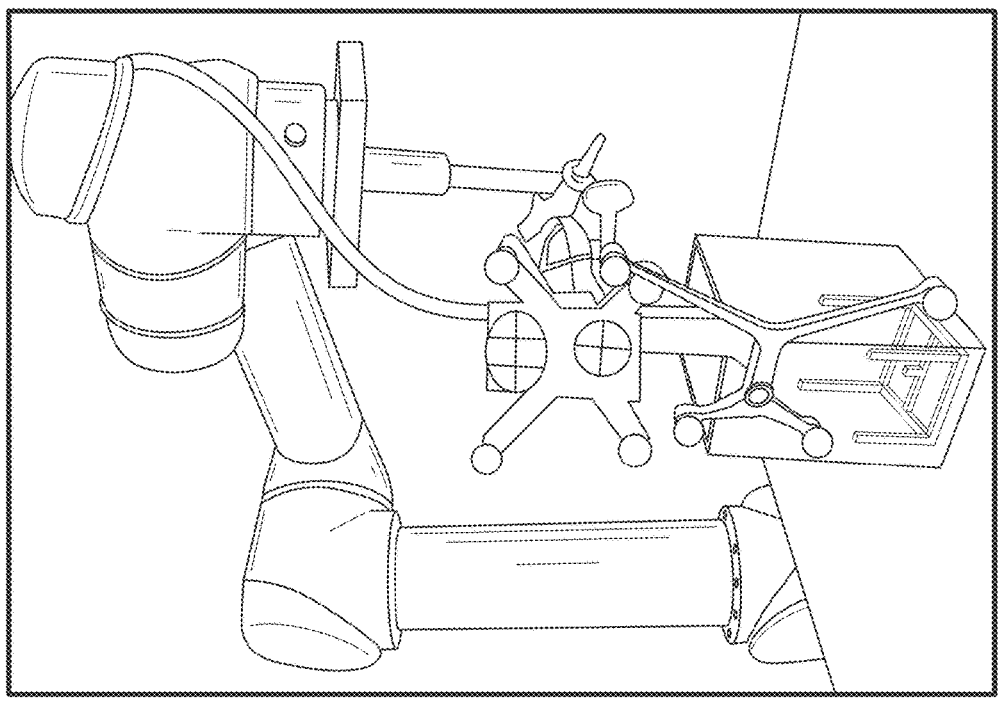

FIG. 32A illustrates an image of positioning an ultrasound transducer for B-mode imaging, and FIG. 32B illustrates an image of a 3D slicer according to FIG. 32A.

FIG. 33A illustrates an image of positioning an ultrasound transducer and laser tip for photoacoustic imaging and FIG. 33B illustrates an image of a 3D slicer according to FIG. 33A.

FIG. 34A illustrates a photoacoustic assistant module with real-time B-mode imaging capabilities.

FIG. 34B illustrates images of the visual guidance interface with real-time photoacoustic images and models of the laser tip and laser path.

Figure 35:
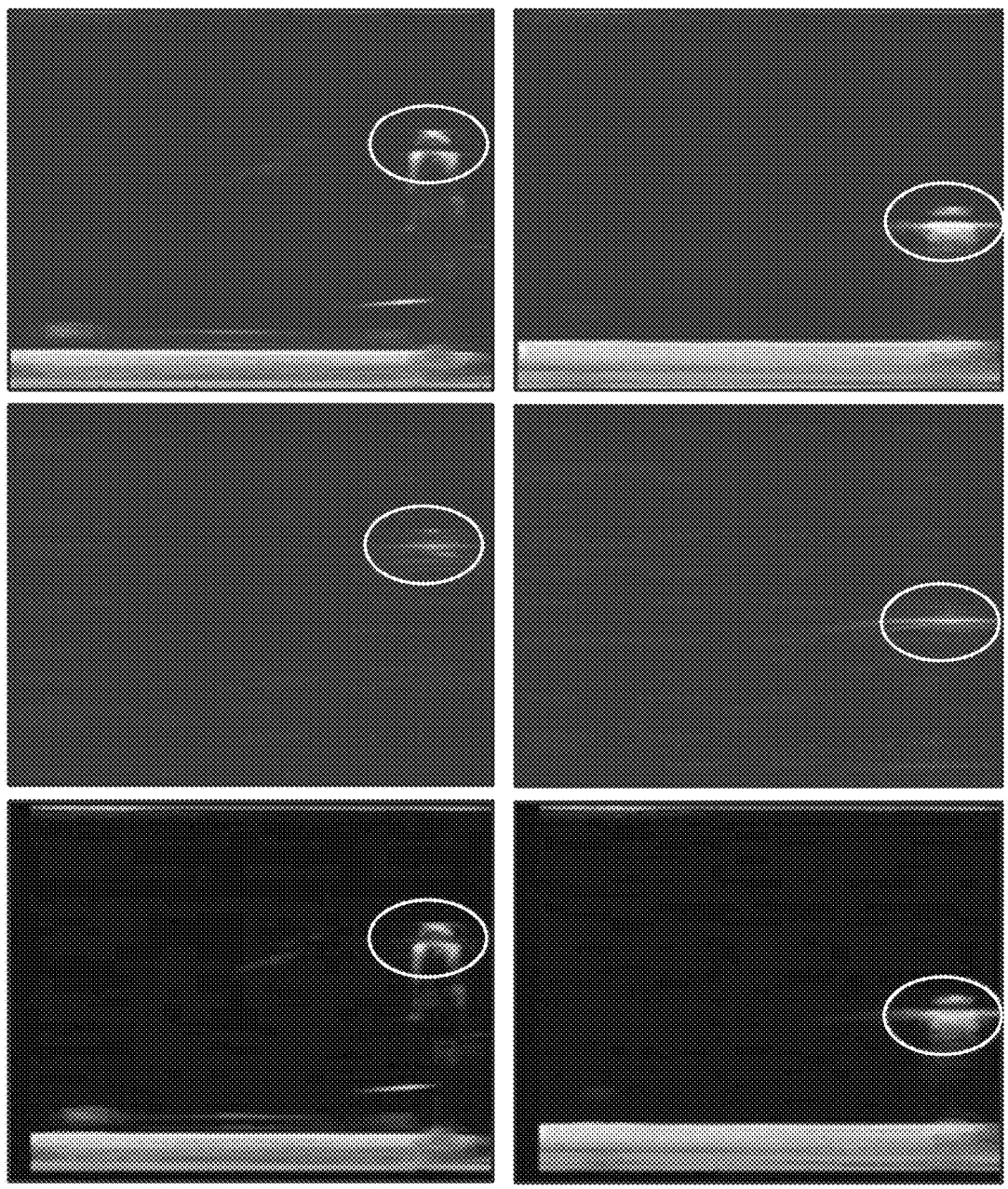

FIG. 35 illustrates photoacoustic image results for two targets: B-mode images (top), photoacoustic images (middle), and overlaid images (bottom); circles indicate target.

Figure 36:
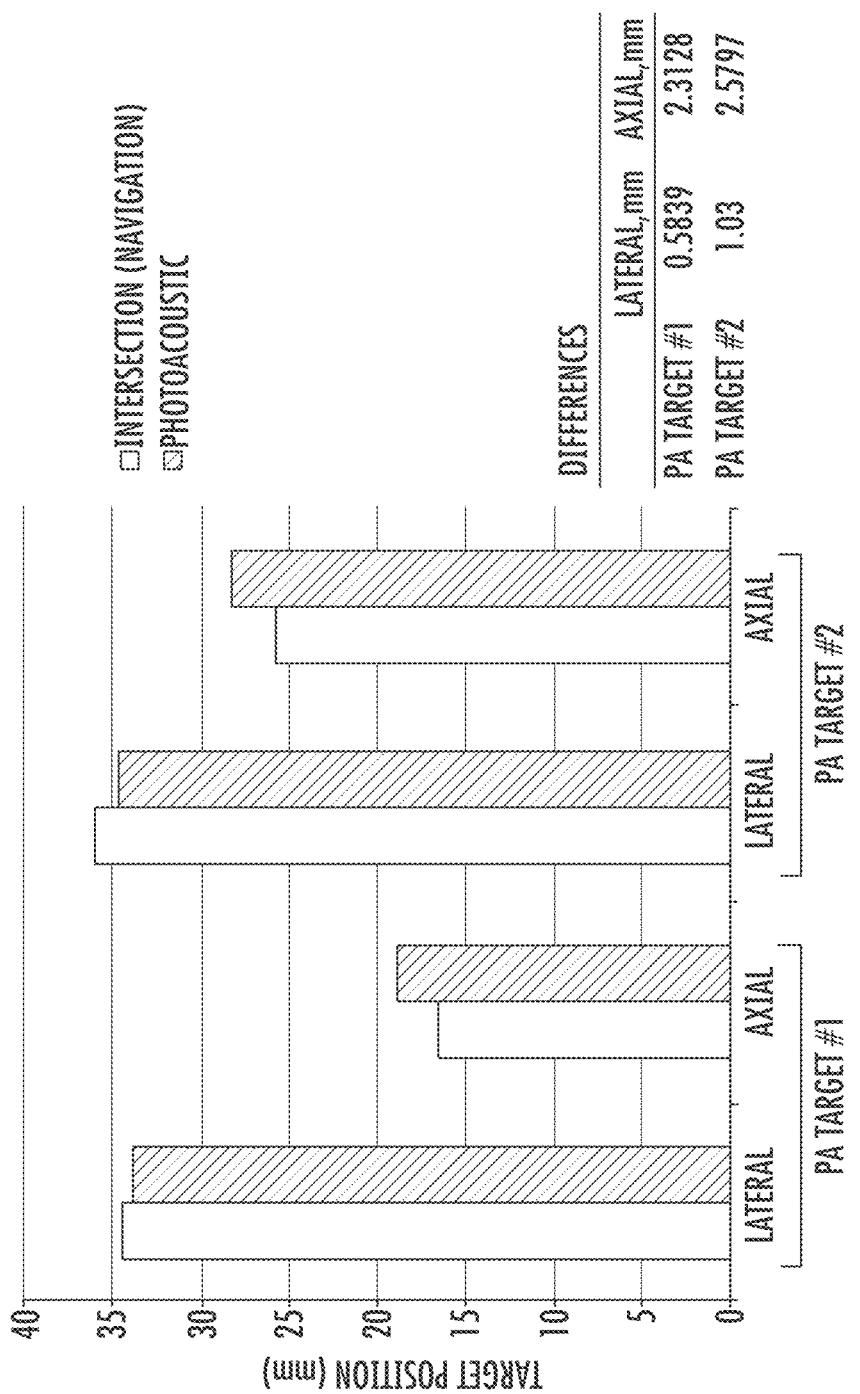

FIG. 36 illustrates a graphical view of the measurements expressed in the US image plane (i.e., lateral and axial directions) for photoacoustic and navigational methods.

Figure 37A:
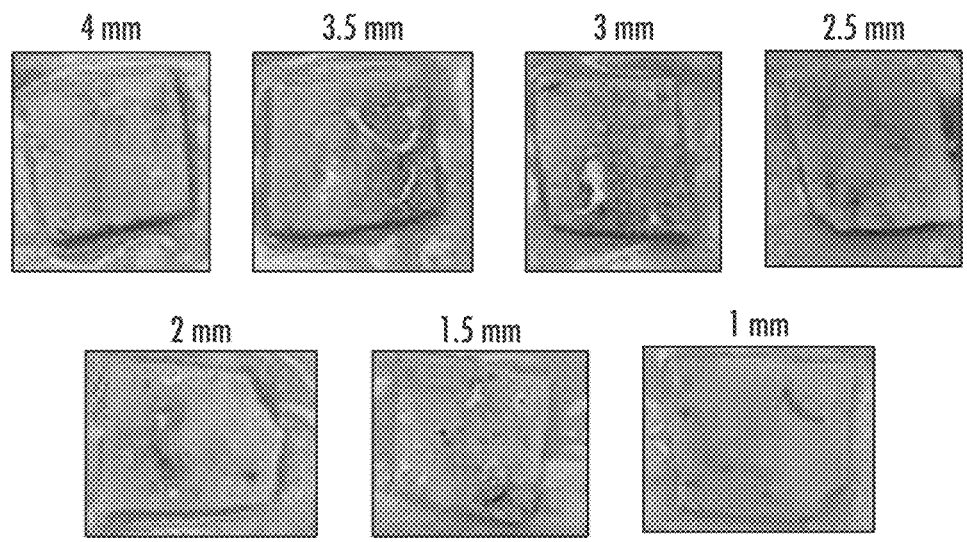
Figure 37B:
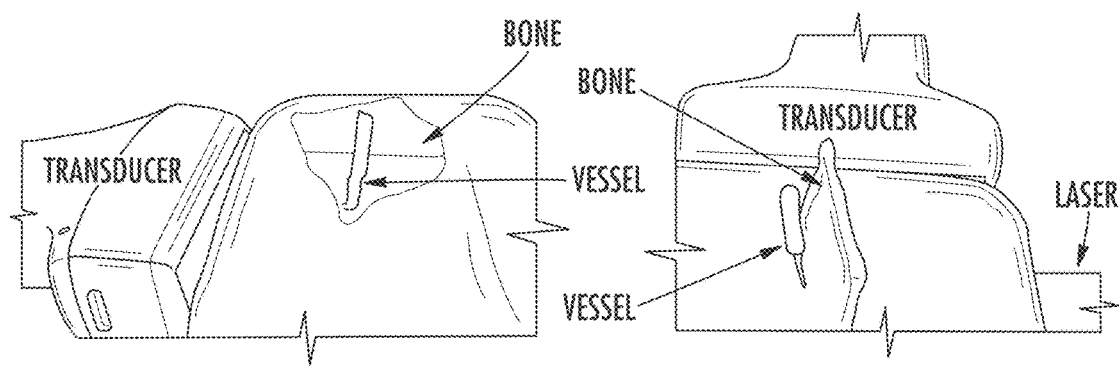

FIGS. 37A and 37B illustrate images of a skull bone sanded to the thickness indicated above each image and the experimental setup, respectively.

Figure 38:
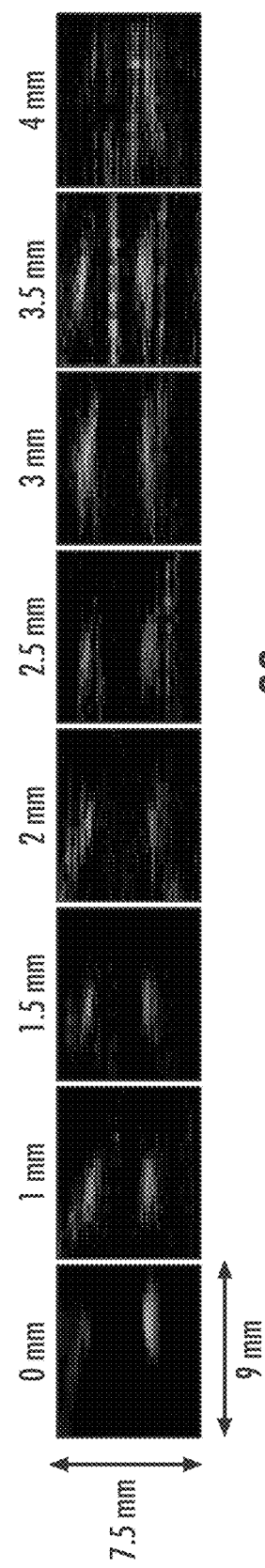

FIG. 38 shows sample photoacoustic images of the target in FIG. 37B, taken with 800 nm wavelength (13.1 mJ per pulse) in the presence of the bone thicknesses indicated above each image and when no bone was present (0 mm), representing the changes in vessel contrast that would be observed as the sphenoid bone is drilled.

Figure 39B:
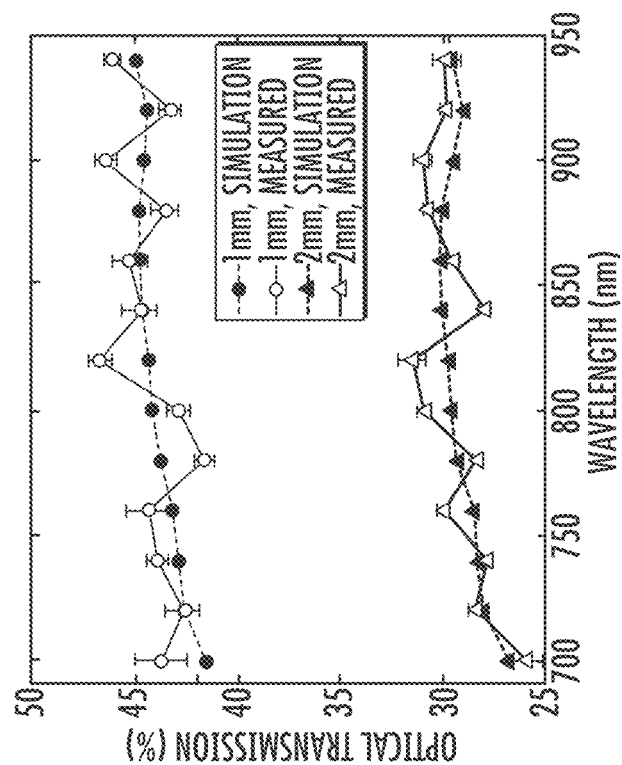
Figure 39A:
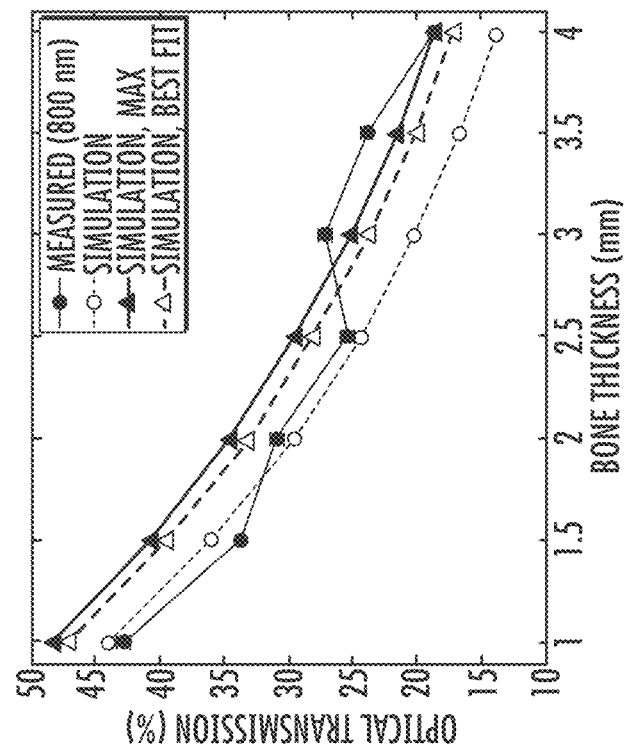

FIGS. 39A and 39B illustrate graphical views of optical transmission rate due to bones of varying thicknesses and varying laser wavelengths respectively, as measured with Monte Carlo simulations and experimental results.

Figure 40A:
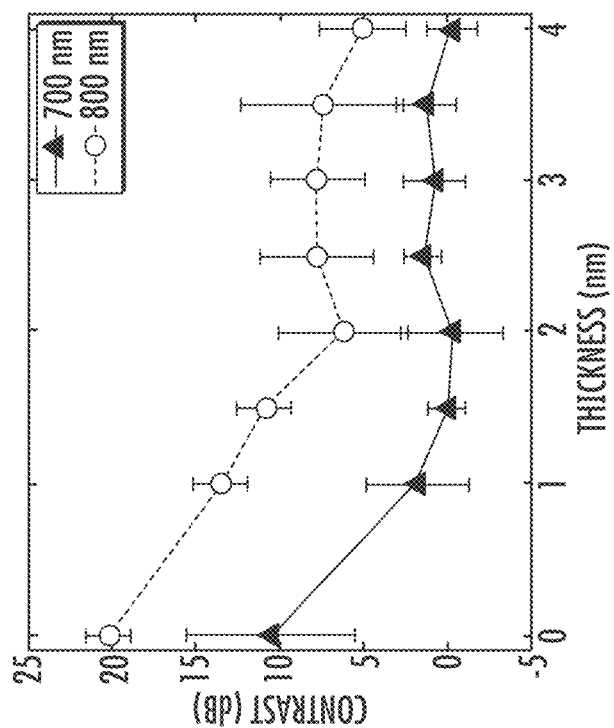
Figure 40B:
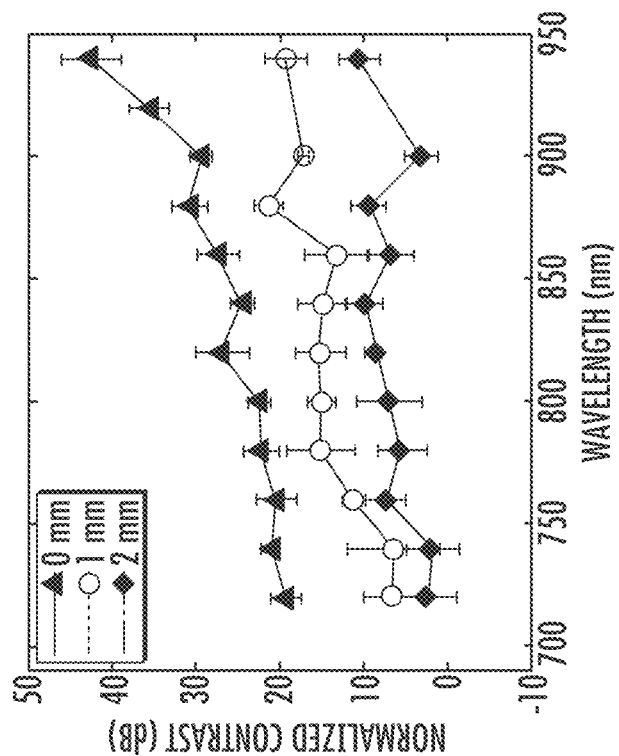

FIGS. 40A and 40B illustrate graphical views of contrast of the photoacoustic signal as a function of bone thickness and laser wavelength, respectively for the wavelengths or bone thicknesses indicated in the legends of each plot.

FIG. 41A illustrates a graphical view of loss in contrast relative to the signal with no bone with gray lines showing individual means for each wavelength and black lines showing mean results for all wavelengths±one standard deviation.

FIG. 41B illustrates a graphical view of mean contrast loss vs. mean optical insertion loss over 720-940 nm wavelengths with gray points showing measurements for each wavelength for 1, 1.5, and 2 mm bone thicknesses, black points showing the mean values for all wavelengths and all thicknesses (1, 1.5 and 2.0 mm thicknesses are noted next to the corresponding points), and vertical and horizontal error bars representing±one standard deviation.

Figure 42:
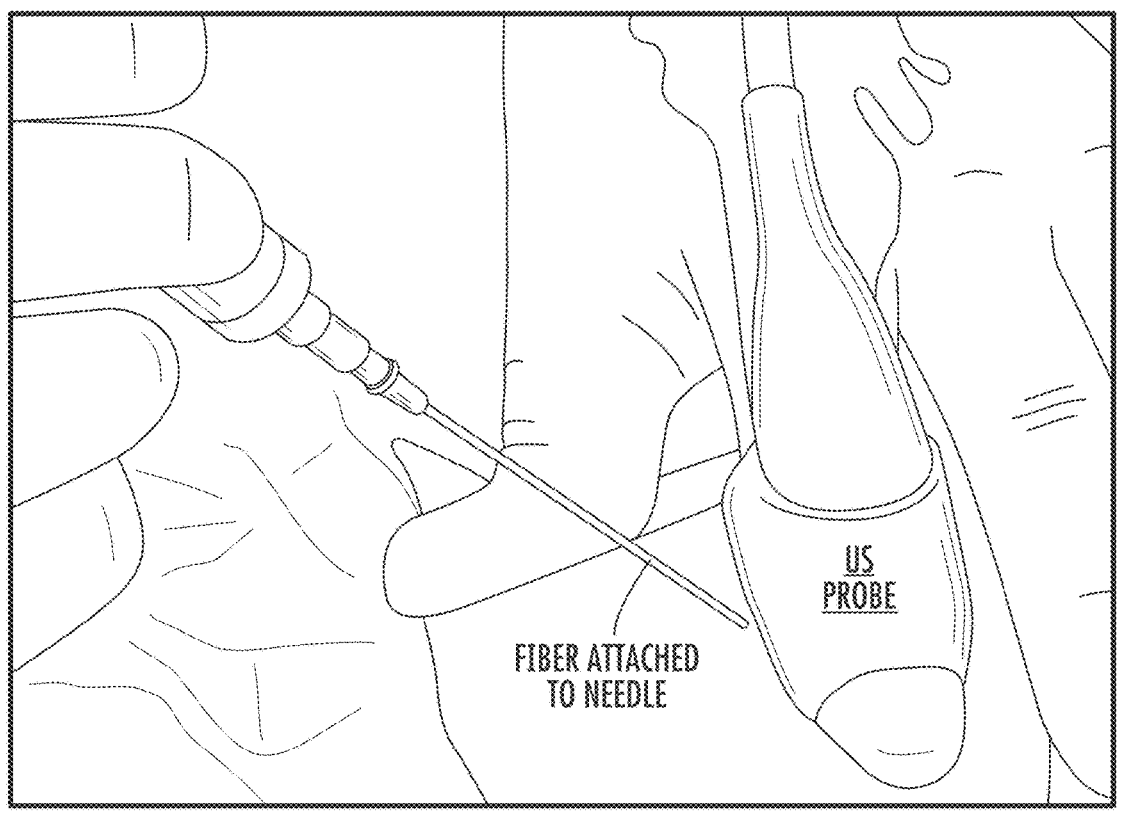

FIG. 42 illustrates an image of a photoacoustic system for finding vessels for IV treatments.

Figure 43:
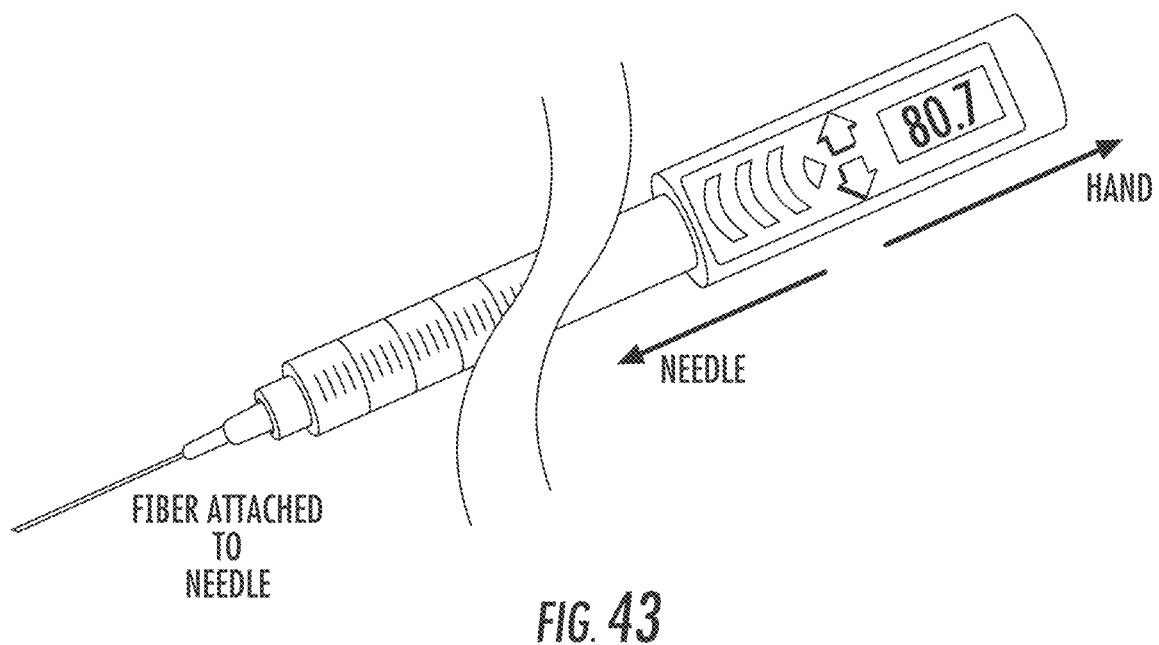

FIG. 43 illustrates an image of an all-optical photoacoustic system for finding vessels for IV treatments with a display housed on the syringe.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a method and system for photoacoustic imaging for guiding medical procedures. A transducer is placed near the site of the procedure. The optical fiber, coupled to an electromagnetic source, such as a laser, is attached to a medical device. During the procedure, the device and optical fiber are inserted into the procedure site where the optical fiber illuminates the procedure site, which has a thickness of approximately 2 mm. Photoacoustic images are acquired to visualize the procedure site as the procedure is proceeding in order to provide real-time guidance. This system is applicable to multiple surgical and interventional procedures, such as transsphenoidal surgery.

In the case of a transsphenoidal surgery, a transducer is placed on the temporal region of the patient's skull. The temporal region includes the pterion bone which is the thinnest portion of the human skull measuring 1-4.4 mm thick. The optical fiber, coupled to an electromagnetic source such as a laser, is attached to a surgical tool, such as a surgical drill. During the surgery, the drill and optical fiber are inserted into the nasal passage where the optical fiber illuminates the sphenoid bone (located at the rear of the nasal septum), which has a thickness of 0.4-8.8 mm. Intraoperative photoacoustic images are acquired to visualize hidden blood vessels as surgeons are drilling to remove the sphenoidal bone.

In one embodiment described herein a system and method is provided to perform photoacoustic imaging of transsphenoidal surgeries. In another embodiment described herein, a novel beamformer is employed to overcome unique, photoacoustic-specific challenges (e.g. insufficient laser fluence). It should be noted that while one possible application of the system, method and beamformer is transsphenoidal surgery, these innovations can also be used in: (1) any surgical application where avoidance or visualization of unseen blood vessels or similar photoacoustic targets is critical (e.g. otolaryngological, laparoscopic, or facial plastic surgery); and (2) improving the image quality of photoacoustic systems in general.

Figure 1:
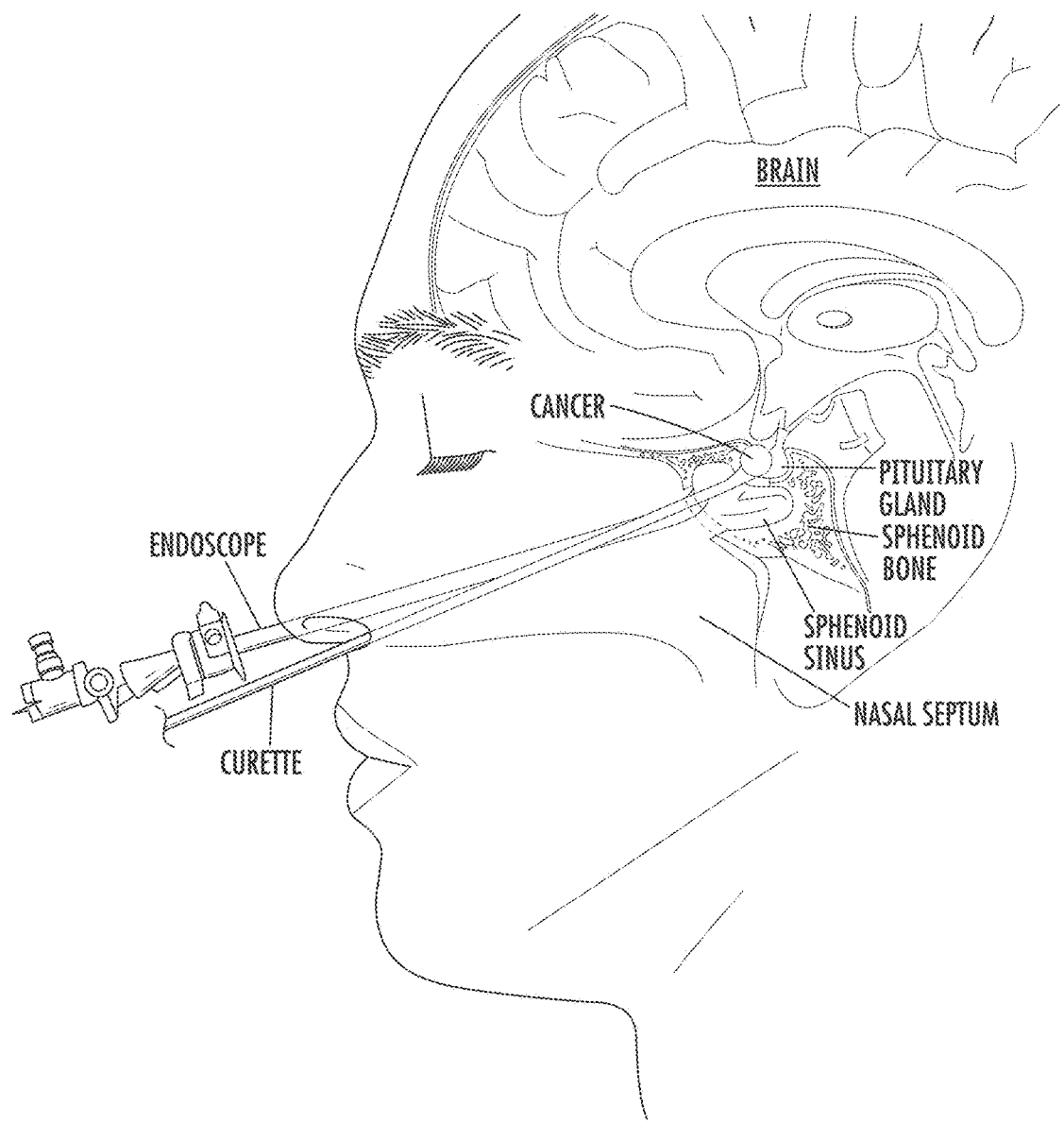
FIG. 1 illustrates an exemplary transsphenoidal surgical field.
Figure 2:
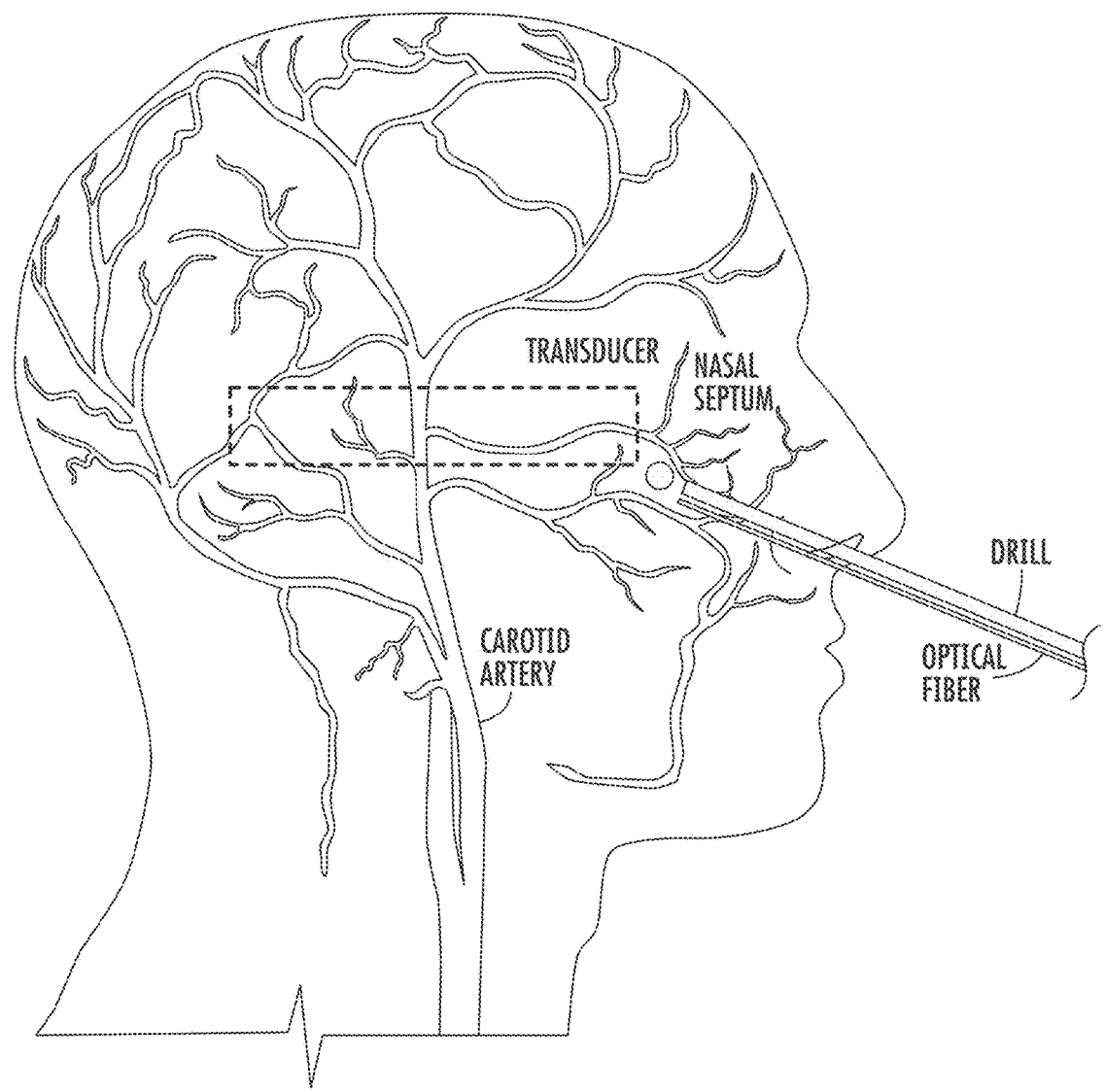
FIG. 2 illustrates a schematic diagram of a system for photoacoustic imaging for guided endonasal surgeries, according to an embodiment of the present invention.

There is currently no dedicated photoacoustic imaging system available for guiding endonasal surgeries. FIG. 2 illustrates a schematic diagram of a system for photoacoustic imaging for guided endonasal surgeries, according to an embodiment of the present invention. To adapt photoacoustic imaging for this task, a transducer is placed on the temporal region on the outside of the patient's skull (and skin), as indicated by the dashed box in FIG. 2. The temporal region includes the pterion bone which is the thinnest portion of the human skull measuring 1-4.4 mm thick. The optical fiber, coupled to a laser, is attached to a surgical drill. During the surgery, the drill and optical fiber are inserted into the nasal passage where the optical fiber illuminates the sphenoid bone, which has a thickness of approximately 2 mm. Intraoperative photoacoustic images are acquired to visualize blood vessels and sphenoidal bone. The ability to visualize the distance between bone and blood in the photoacoustic images informs surgeons of their proximity to the carotid artery as they are drilling the sphenoidal bone. It should be noted that the transducer could also be placed on the tool tip or any other suitable positioning known to or conceivable by one of skill in the art. The transducer also does not have to be on the temporal region as shown. This transducer could also be placed inside the nose, not attached to any tools or in any other suitable position known to or conceivable by one of skill in the art. It is also possible that the transducer take the form of a traditional ultrasound probe or the traditional ultrasound probe can be replaced with an optical fiber. The optical fiber can be the optical fiber used to provide light for the system or an additional optical fiber with a Fabry-Perot interferometer. The fiber also does not have to be attached to the tool as shown. This fiber could exist independently to visualize structures for path planning.

The image information is transmitted to a non-transitory computer readable medium for processing. The non-transitory computer readable medium can take any suitable form known to one of skill in the art. The non-transitory computer readable medium is understood to be any article of manufacture readable by a computer or other computing device. Such non-transitory computer readable media includes, but is not limited to, magnetic media, such as floppy disk, flexible disk, hard disk, USB memory device, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device. The computing device can take the form of a PC, tablet, smartphone, processor, or any other suitable computing device known to or conceivable by one of skill in the art. The computing device and non-transitory readable medium can be specially designed specifically for the implementation of the present invention. In some instances, the computing device and the non-transitory computer readable medium of the present invention perform tasks that are not able to be carried out with a common computing device or non-transitory computer readable medium. These functions are specific to the computing device of the present invention and therefore, provide a unique computing environment.

Figure 3:
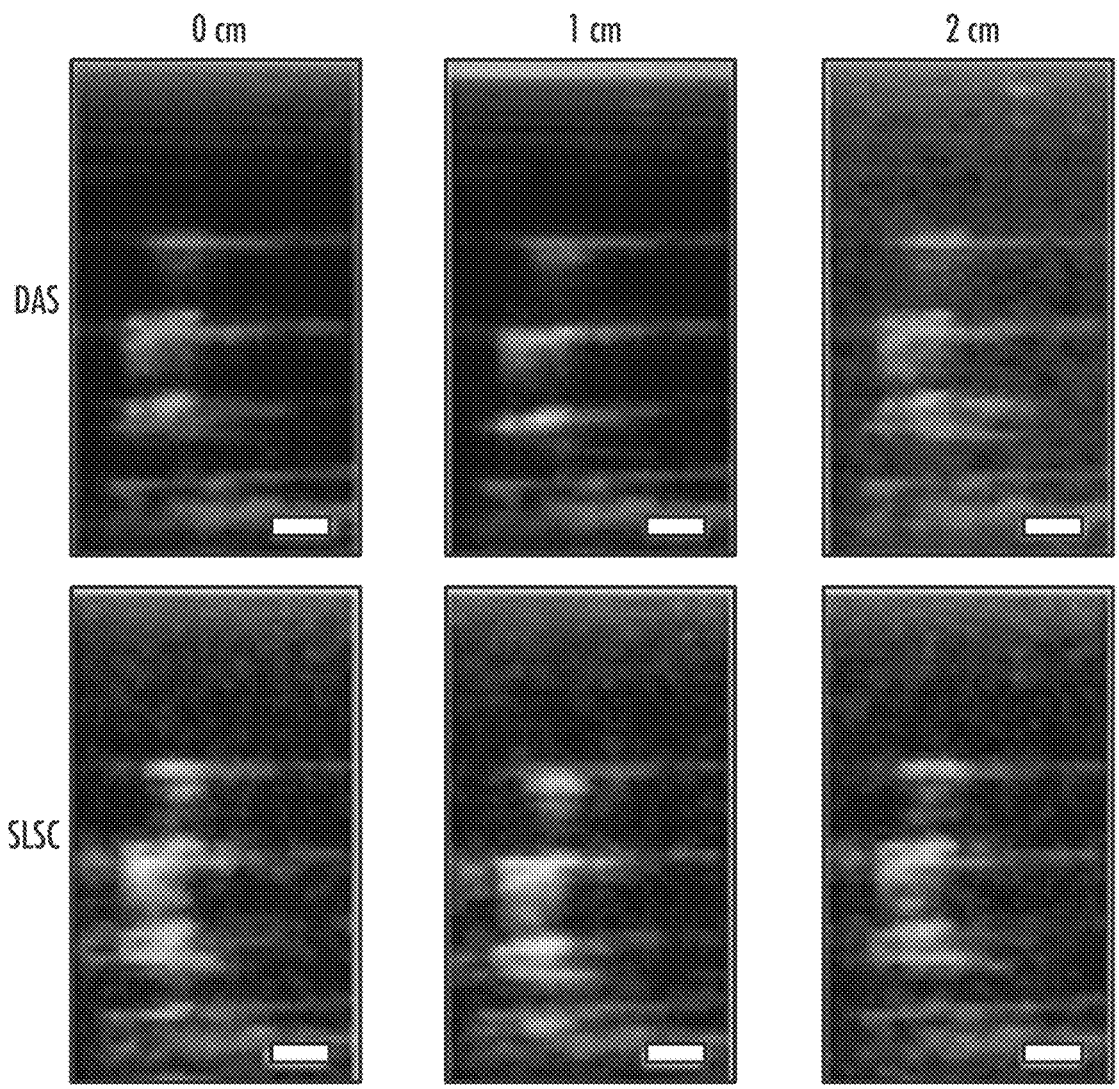
FIG. 3 illustrates images of brachytherapy seeds taken with delay-and-sum (DAS) and SLSC imaging modalities to show benefits of SLSC over DAS in photoacoustic imaging.

With respect to the novel beamformer disclosed herein, conventional beamformers, like delay-and-sum (DAS), use an amplitude based approach that suffers from poor contrast and low signal-to-noise ratios (SNR) when the laser fluence and penetration is insufficient. A coherence based approach, like short-lag spatial coherence (SLSC), used and optimized for the present invention, has potential to overcome the traditional roadblocks associated with insufficient laser penetration for a multitude of applications. FIG. 3 illustrates images of brachytherapy seeds taken with DAS and SLSC imaging modalities to show benefits of SLSC over DAS in photoacoustic imaging. Note the markedly improved signal contrast as distance between the light source and the three targets is increased from 0-2 cm. This occurs because the SLSC beamformer measures and displays the acoustic wavefield's spatial coherence, which is independent of signal amplitude. The beamforming can also be executed by the non-transitory computer readable medium processing the images.

In general, amplitude- and coherence-based beamforming is conducted by starting with $s_i(n)$, the time-delayed signal received by the $i^{th}$ transducer element at sample number (or depth), n. One pixel in a conventional amplitude-based DAS image may be obtained by summation of all $s_i$ at a particular depth n. In a coherence-based approach, the normalized spatial coherence across the receive aperture, $\hat{R}$, and the resulting short-lag spatial coherence, $R_{sl}$, may be calculated as follows:

$$\hat{R}(m) = \frac{1}{N-m} \sum_{i=1}^{N-m} \frac{\sum_{n=n_1}^{n_2} s_i(n) s_{i+m}(n)}{\sqrt{\sum_{n=n_1}^{n_2} s_i^2(n) \sum_{n=n_1}^{n_2} s_{i+m}^2(n)}} \quad (1)$$

$$R_{sl} = \sum_{m=1}^{M} \hat{R}(m) \quad (2)$$

where m is the lateral spacing, or lag, between two elements on the receive aperture, N is the number of receive elements, and M is the maximum number of lags integrated to make a SLSC image. One pixel in a SLSC photoacoustic image is formed by computing Eqs. 1 and 2 at a depth n of the channel signals, using a correlation kernel size equal to $n_2 - n_1$, centered about n. The performance of the two beamformers can be tested using target contrast and SNR as follows:

$$\text{Contrast} = 20\log_{10}\left(\frac{s_i}{s_0}\right) \quad (3)$$

$$SNR = 20\log_{10}\left(\frac{s_i}{\sigma_0}\right) \quad (4)$$

The SLSC beamformer has shown significant improvements over DAS when applied to ultrasound data from in vivo hearts, livers, vessels, and fetuses. Additional benefits are achieved in photoacoustic images when coherence-based beamformers are specifically developed to overcome conventional limitations with poor laser penetration and insufficient laser fluence. Other applications that will benefit from these beamformers include fusion of photoacoustic images with video images in minimally invasive surgeries.

Figures 4A, 4B, 4C:
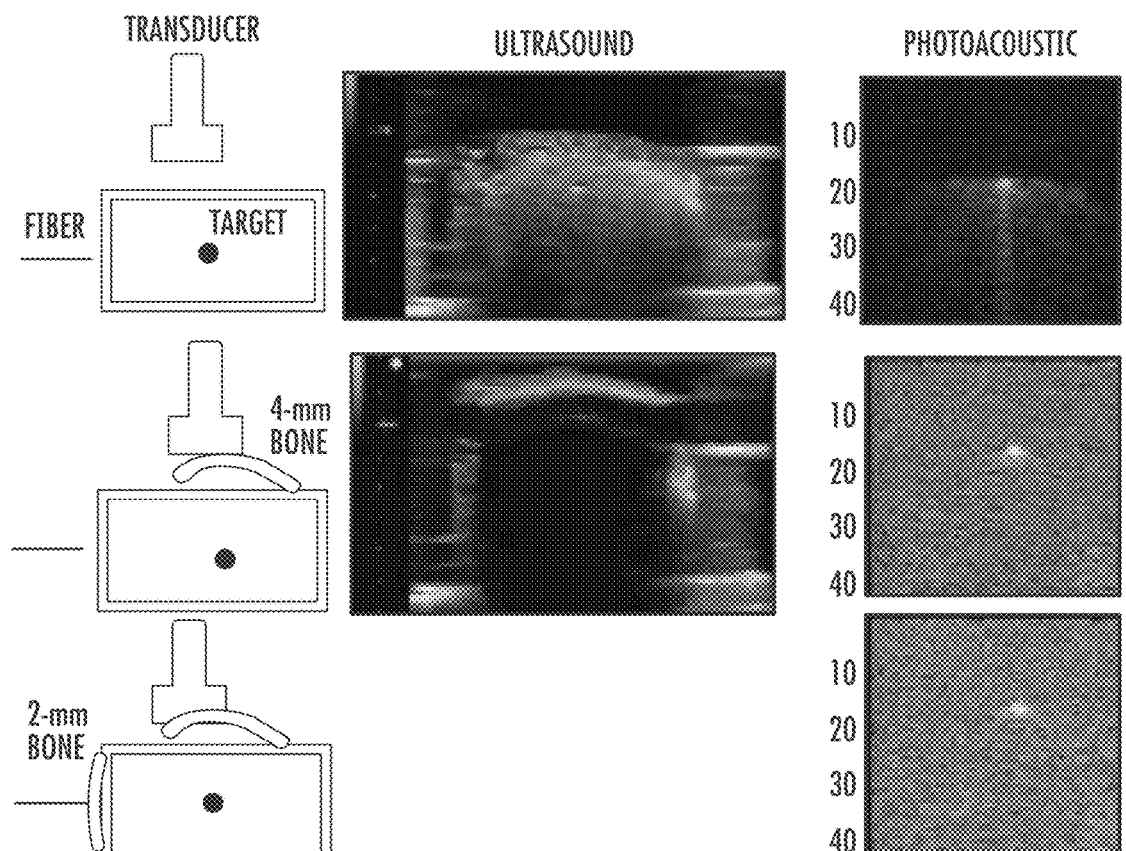
FIG. 4A illustrates a schematic diagram of an experimental setup according to an embodiment of the present invention.
FIG. 4B illustrates ultrasound images taken according to the experimental setup.
FIG. 4C illustrates photoacoustic images taken according to the experimental setup.

FIG. 4A illustrates a schematic diagram of an experimental setup according to an embodiment of the present invention, FIG. 4B illustrates ultrasound images taken according to the experimental setup, and FIG. 4C illustrates photoacoustic images taken according to the experimental setup. Preliminary work with a spherical metal target embedded in a plastisol phantom indicates that it is possible to detect a target in the presence of human adult skull specimens, as shown in FIG. 4B. Experiments were conducted to determine the feasibility of imaging through one and two formalin-fixed human adult cadaveric skull specimens. A plastisol phantom embedded with a spherical metal target was submerged in a water tank. An Ultrasonix L14-5W/60 linear transducer was placed approximately 1 cm above the phantom to acquire ultrasound and photoacoustic image data. An optical fiber was coupled to a 1064 nm Nd:YAG laser and the free end of the fiber was placed orthogonal to the probe. The target was located at a depth of 18 mm with no bone and 15.6 mm when the 4-mm thick bone was placed between the transducer and the phantom, which is consistent with the expected depth shift due to sound speed inhomogeneities between the bone and the phantom. When a 2-mm thick bone was added between the fiber and the phantom to simulate an imaging scenario prior to drill penetration, the target was similarly located at a depth of 15.6 mm. This expected depth shift is not a major concern if the distance between two targets (e.g. blood and bone or two blood vessels) in a photoacoustic image can be measured to inform the surgeon of his or her proximity to the carotid. An alternative is to add a margin of error equal to the expected depth shift when displaying interventional images for the neurosurgeons.

Figure 5:
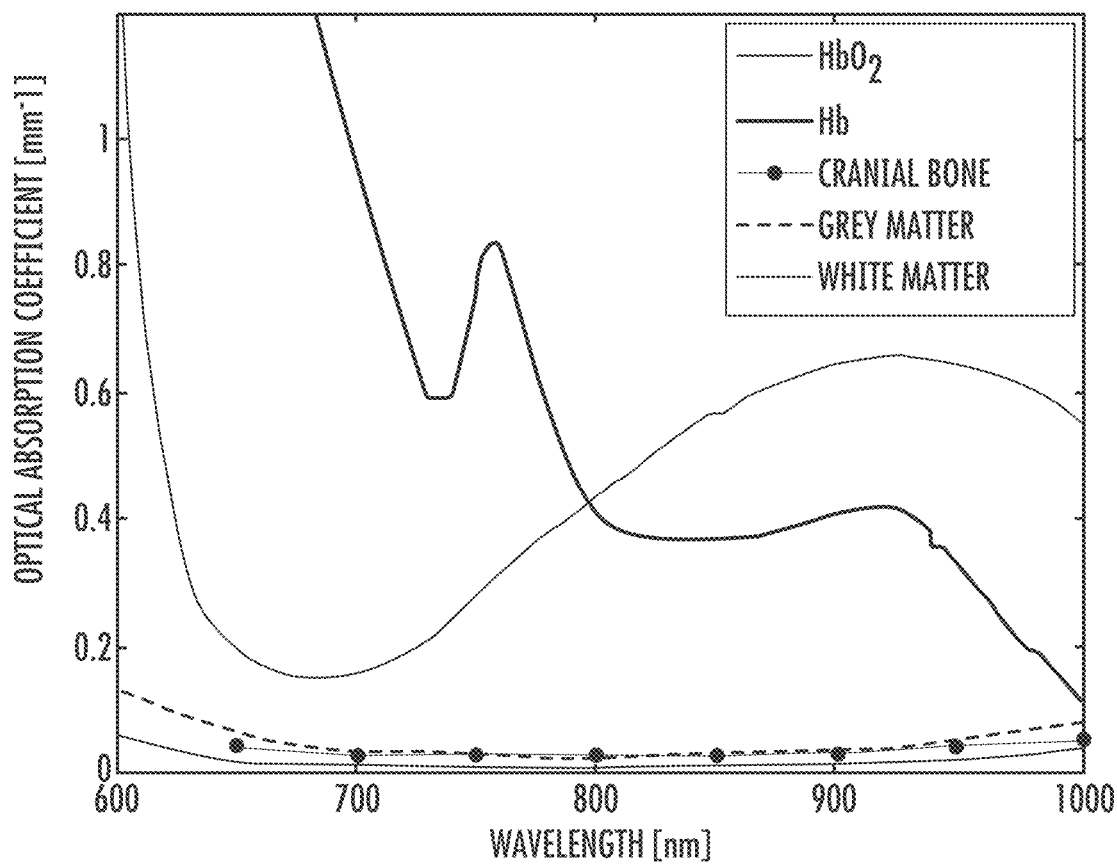
FIG. 5 illustrates a graphical view of optical absorption spectra of blood, bone, and brain tissues.

A wave simulation package is used to understand attributes of wave propagation in the complex cranial environment. A human skull can then be modeled using CT images from patients or the Visible Human Project®. Realistic acoustic properties (e.g. speed of sound, density) are set for each identifiable layer in the CT images. To distinguish between blood and sphenoidal bone as photoacoustic sources, the initial pressure distribution, $p_0$ of each target type is scaled relative to each other according to the equation:

$$p_o = \mu_a \Gamma F \qquad (5)$$

where, $\mu_a$ is the optical absorption coefficient (which is significantly different for bone and blood and varies with laser wavelength, as shown in FIG. 5), $\Gamma$ is the Grüneisen parameter (approximately 0.25 and 1.1 in blood and bone, respectively), and F is the laser fluence. The expected differences in laser fluence is calculated using light propagation and scattering properties and added as an input to the simulation to differentiate between blood and bone. These scaling attributes yield simulated photoacoustic images with signal amplitude distributions that are similar to expected values.

If the sphenoidal bone is thicker than 2 mm in some patients, one system limitation in these cases would be light penetration and detection of blood vessels only when at least 2 mm of bone remains to be drilled. If the energy needed to visualize targets in the presence of sphenoidal bone is higher than the ANSI limit, one alternative approach is to use larger fibers, within the limits of the nostril size. For example, utilizing a 1.5 mm core diameter rather than a 1 mm fiber marginally increases the required workspace, but offers a factor of 2.25 reduction in energy density. Another option is to use multiple fibers or modify the shape of the fiber tip to increase the surface area (i.e. circle vs. ellipse).

The SLSC beamformer is based on the van Cittert Zernike (VCZ) theorem applied to pulse-echo ultrasound, which predicts that the spatial coherence, C, of a wavefront is given by the following equation:

$$C = |\mathcal{F}\{H^2 \cdot \chi^2\}|, \qquad (6)$$

where $\mathcal{F}$ denotes the Fourier transform, H is the transmit beam pressure, and $\chi$ is the amplitude profile of the target being imaged (i.e. the target reflectivity profile, which might be constant if modeling uniform tissue or a square pulse if modeling a lesion). Note, in current implementations, when applied to photoacoustic imaging, the H in Eq. 6 can be considered as a broad unfocused optical transmit beam and thus coherence is mostly determined by target shape.

Figure 6:
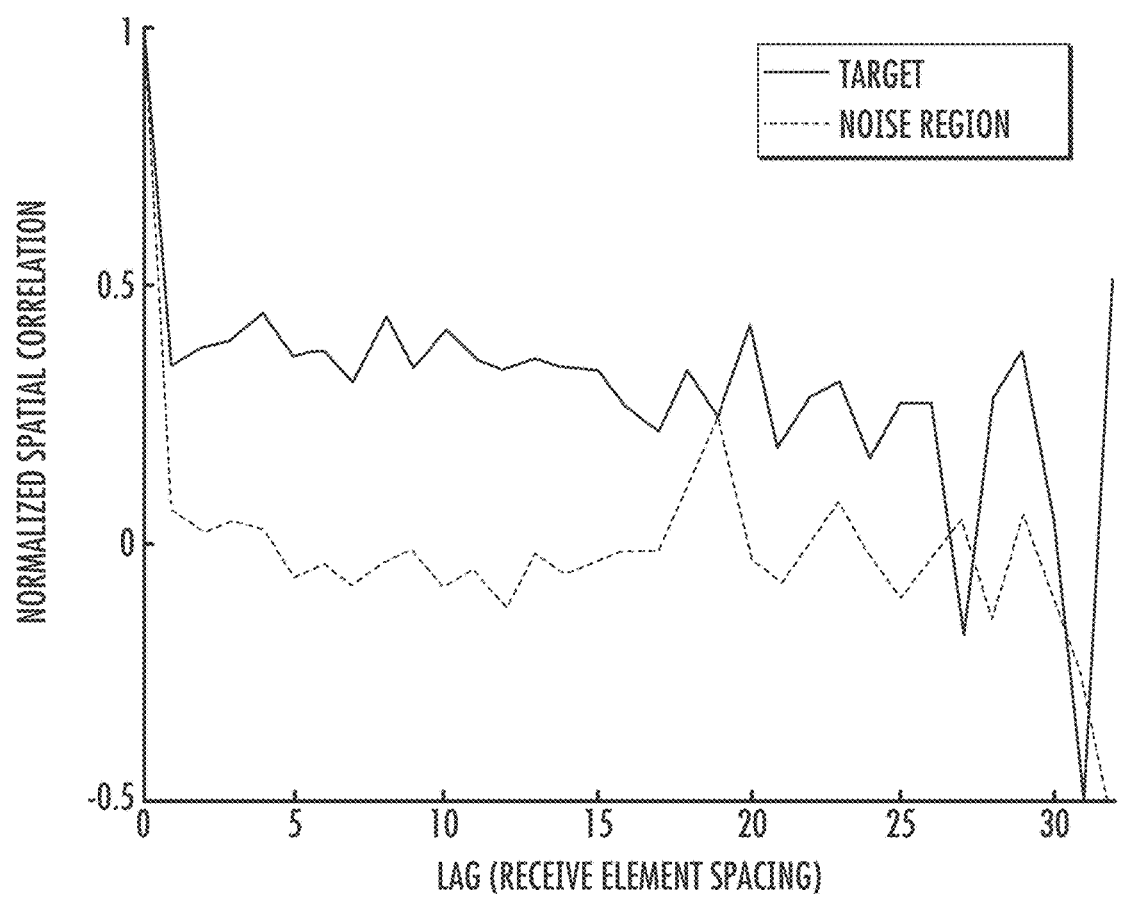
FIG. 6 illustrates a graphical view of coherence curves, according to an embodiment of the present invention.

FIG. 6 illustrates a graphical view of coherence curves, according to an embodiment of the present invention. The photoacoustic spatial coherence functions were investigated for the target shown in FIG. 4, in the presence and absence of the skull specimens. Coherence curves were calculated using Eq. 1. In general, the targets have higher spatial coherence across the receiver compared to the noise regions surrounding them. FIG. 6 shows the coherence curves of the target and noise regions when both skull specimens were present. In the absence of the skull specimens, signals from the target had higher spatial correlation than that shown in FIG. 6, indicating that the presence of cranial bone reduces the spatial coherence of acoustic waves emanating from a target. Coherence curves like those shown in FIG. 6 were integrated, as described by Eq. 2, to create the SLSC images shown in FIG. 7. The integral of the noise region is lower than that of the target, particularly in the short-lag region (i.e. the region where receive element spacings range from 1 to 10% of the receive aperture size).

Coherence curves for bone and blood, similar to those shown in FIG. 6, can be mapped under different imaging conditions (e.g. phantoms with and without bone specimens, simulations with no noise, simulations with added noise, and ex vivo). Theoretical equations can then be derived to describe these coherence functions and compare them to the simulation and experimental curves. If the van Cittert-Zernike theorem (Eq. 6) applies to these media, there will be good agreement between the theoretical and experimental curves. A relationship between acoustic receiver size and collimated laser beam size for creating optimal coherence-based photoacoustic images is also possible. H in Eq. 6, which originally refers to the ultrasound acoustic pressure, has a similar optics corollary (i.e. the initial optical beam irradiation pattern). This can be tested by combining Eq. 5 with optical diffraction theory (e.g. Huygens-Fresnel principle and the Fraunhofer approximation). The shape of the illumination pattern can be varied. The resulting coherence curves may vary as a function of the illumination pattern although the target is the same. The corollary to H in Eq. 6 may be optimized to uniquely design coherence-based beamformers by modifying the optical beam. This feature is not possible with the coherence-based beamforming (e.g. SLSC) applied to ultrasound data.

Image improvements are achieved with the SLSC beamformer, compared to the DAS beamformer, as shown in FIG. 7. The energy at the tip of the optical fiber was varied from 9 to 18 mJ, and photoacoustic images were acquired when bone specimens were placed between the phantom and transducer and between the fiber and phantom. The contrast of the target in SLSC beamformed images was 11-27 dB greater than that in matched DAS beamformed images, measured from the mean of five image acquisitions at each energy level. However, at lower energies (e.g. 9 mJ), although contrast was improved, the signal-to-noise ratio in SLSC images was reduced by up to 3 dB, compared to that of the DAS images.

Figure 11:
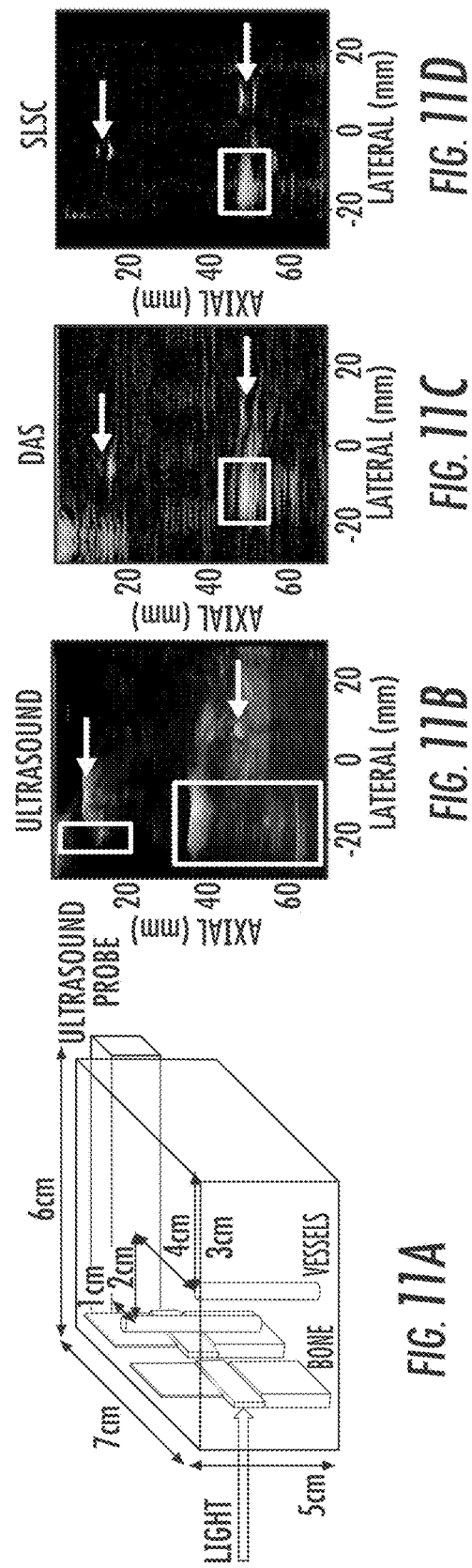
FIG. 11A illustrates a schematic diagram of an experimental setup according to the invention.
FIG. 11B illustrates an ultrasound image resulting from the setup illustrated in FIG. 11A.
FIG. 11C illustrates a corresponding DAS image for the setup illustrated in FIG. 11A.
FIG. 11D illustrates a SLSC image for the setup illustrated in FIG. 11A.

Although reducing the dynamic range of DAS images will display less background noise, this adjustment is not sufficient for the proposed technology, as the laser fluence incident on a vessel covered by bone is expected to be significantly lower than that incident on the bone. Reducing the dynamic range of a DAS image will remove the necessary vessel signal in the presence of bone, as demonstrated in FIGS. 11A-11D. FIG. 11A illustrates a schematic diagram of an experimental setup according to the invention. FIG. 11B illustrates an ultrasound image resulting from the setup illustrated in FIG. 11A. FIG. 11C illustrates a corresponding DAS image for the setup illustrated in FIG. 11A, and FIG. 11D illustrates a SLSC image for the setup illustrated in FIG. 11A. In FIGS. 11A-11D boxes and arrows indicate signals from bones and vessels, respectively. DAS and SLSC images are shown with 30 dB dynamic range, respectively. Laser energy was 14 mJ at 1064 nm. These results indicate that further improvements can be made to reduce background noise, enhance the signal at lower energies, and define the optimal beamformer based on clinicians' preferences.

Acoustic-based improvements include averaging before integrating coherence functions, filtering to remove high frequencies before integrating coherence functions, or application of the beamformer to envelope-detected data. Optics-based improvements might include using focused beams (e.g. Bessel beams or spatial-light modulators) to illuminate the target or using multiple fibers (e.g. a fiber bundle) to illuminate the target. One implementation of a fiber bundle could be 7 fibers wrapped around the circumference of the drill. A geometrically identical, 3D printed drill can be used for testing. This design will cause a different illumination profile, increase the incident surface area of light, and thereby potentially allow more energy to be deposited into the body without exceeding ANSI limits for energy density (defined as energy per area).

The quality and performance of each variation of a coherence-based beamformer, beamformer, or illumination method is to be quantitatively evaluated using performance metrics like resolution (based on the full-width at half maximum of point targets), contrast ($|\mu_i-\mu_o|/\mu_i$), contrast-to-noise ratio (CNR, $|\mu_i-\mu_o|/\sigma_o$), signal-to-noise ratio (SNR, $\mu_i/\sigma_i$), where $\mu$ and $\sigma$ represent the mean and standard deviation, respectively, of the data referenced by the subscripts i and o, which represent envelope-detected RF data within regions of interest inside and outside of a target area, respectively. These metrics may be used to guide surgical and interventional procedures (e.g. determine the thickness of bone that remains to be drilled, determine fiber location). In general, contrast is constant, SNR and CNR decrease, and lateral resolution is improved as the short-lag value (i.e. M in Eq. 2) is modulated.

Figure 8:
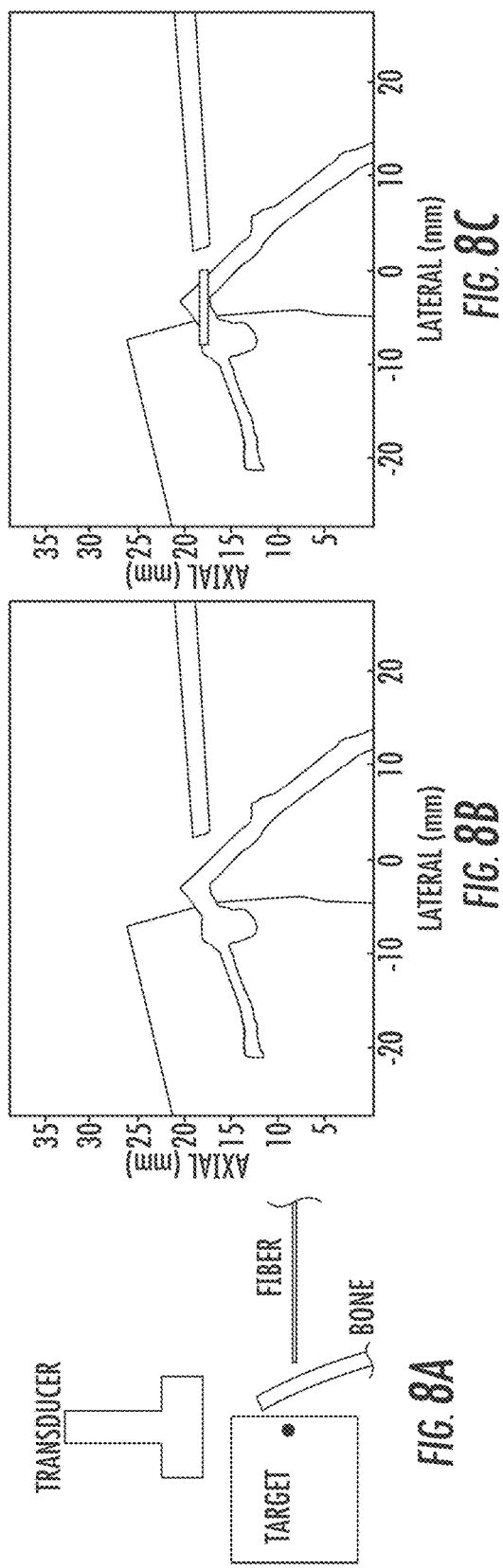
FIG. 8A illustrates a schematic diagram of an experimental setup according to an embodiment of the present invention.
FIG. 8B illustrates an ultrasound image.
FIG. 8C illustrates a corresponding photoacoustic image overlaid on ultrasound image.

FIG. 8A illustrates a schematic diagram of an experimental setup according to an embodiment of the present invention. FIG. 8B illustrates an ultrasound image, and FIG. 8C illustrates a corresponding photoacoustic image overlaid on ultrasound image. Coherence-based beamforming is ideal because it does not rely on signal amplitude, and the signal from bone is expected to be weaker than that from blood. Preliminary results indicate that it is possible to visualize both bone and another target in a photoacoustic image, as shown in FIG. 8C. A plastisol phantom was embedded with a spherical metal target and submerged in a water tank. A human cadaveric skull specimen was placed to the side of the phantom. The transducer was oriented orthogonal to the fiber, such that the target, bone, and fiber were in the same image plane. Photoacoustic images were acquired and overlaid on the ultrasound B-mode images in a yellow-red color scale. The overlay clearly indicates that a photoacoustic response from the target and bone were achieved. Results are promising for detecting bone and vessels in vivo.

Figure 9:
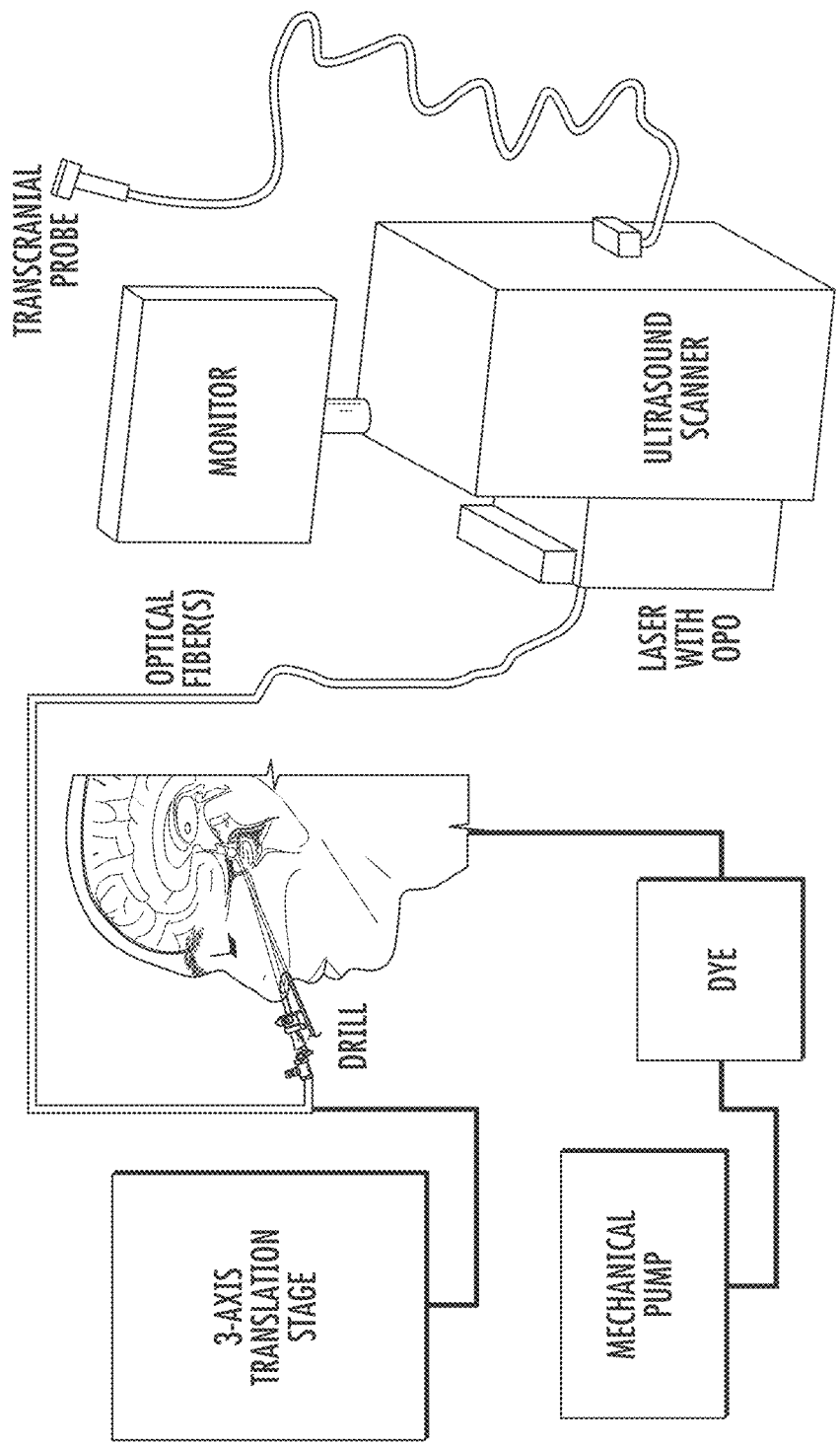
FIG. 9 illustrates a schematic diagram of system components for executing the photoacoustic imaging, according to an embodiment of the present invention.
Figure 10:
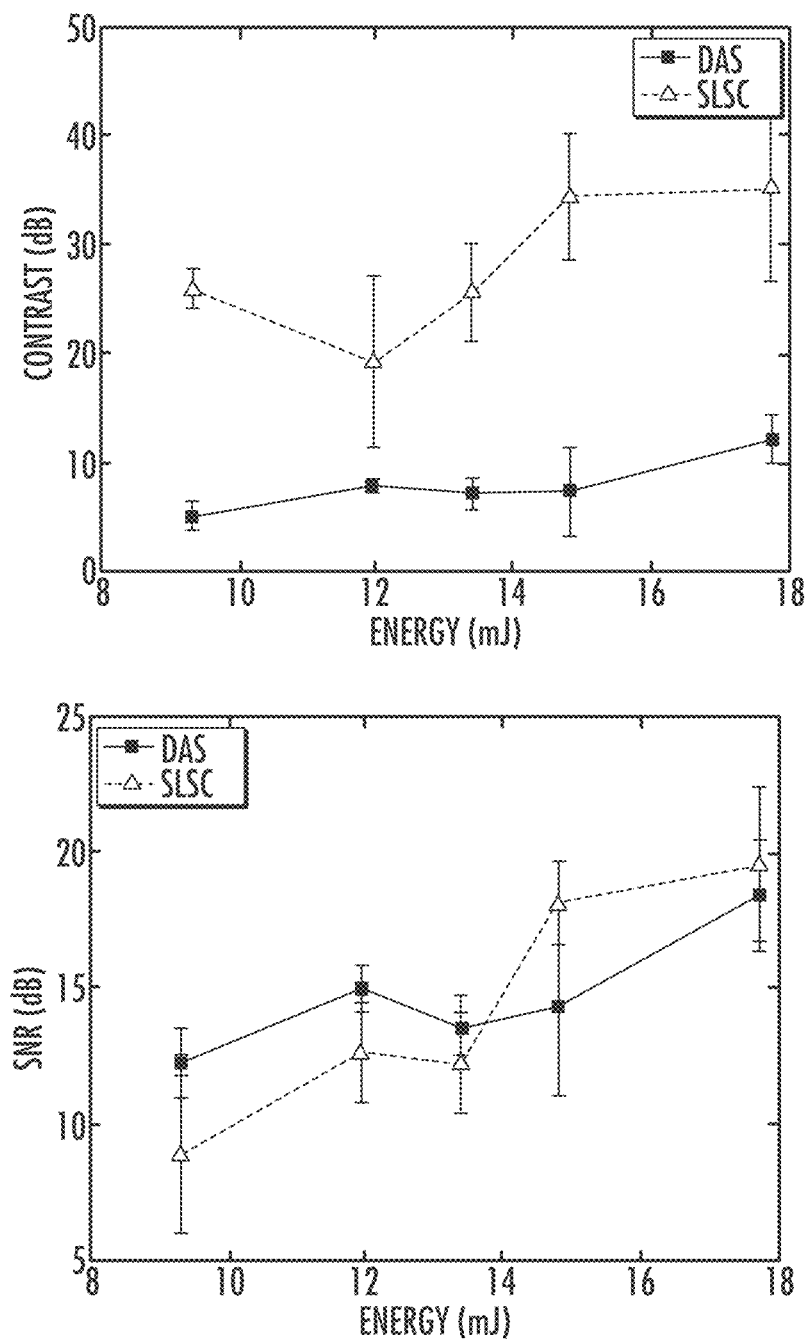
FIG. 10 illustrates graphical views of image improvements achieved with the SLSC beamformer, compared to the DAS beamformer.

FIG. 9 illustrates a schematic diagram of system components for executing the photoacoustic imaging, according to an embodiment of the present invention. The transcranial photoacoustic system, as illustrated in FIG. 9, includes one or more optical fibers attached to a surgical drill, an ultrasound transducer, and an ultrasound scanner synchronized to an Nd:YAG laser with an optical parametric oscillator (OPO). The OPO will enable variable laser wavelength imaging. In a living human, the dye is actually blood and the mechanical pump is the heart. In an experiment, these critical components are simulated.

It should also be noted that one or more robots can be used to control the drill, ultrasound probe, fiber or all three. This helps to achieve optimal photoacoustic images for several reasons: (1) the photoacoustic signal will always be in the central ultrasound plane; and (2) a feedback loop can be created to move the probe relative the orientation of the fiber (attached to the drill, other surgical tools or stand-alone/separated from any tools). This system could additionally be controlled by a robot to find the maximum signal within a given range and automatically puncture with an attached needle.

The robots can be controlled using a computer device and a non-transitory computer readable medium incorporated to or in communication with the robot. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard, disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device. The computing device can take the form of a PC, tablet, smartphone, processor, or any other suitable computing device known to or conceivable by one of skill in the art.

Exemplary Embodiments

The following exemplary embodiments are included by way of example and are in no way considered to be limiting to the present invention. The examples are included to further illustrate the principles of the present invention and other implementations known to or conceivable by one of skill in the art are possible and included within the scope of the invention.

In an exemplary implementation of the present invention, formalin-fixed cadaver heads, with similar properties to those used for achieving good-quality ultrasound tomograms are used.

Alternately, an empty cadaver skull, degassed in a vacuum chamber, and filled with a fresh intact, formalin-fixed human, canine, or monkey brain surrounded by tissue-mimicking material with tubes mimicking the carotid arteries inserted on either side of the pituitary.

The drill is used to access the sphenoid sinus, ensuring that the sphenoid bone closest to the pituitary gland remains intact. The drill is either placed manually or with the assistance of a robot. An endoscope is placed to visualize the surgical field while drilling. The ultrasound transducer is placed for an acoustic window through the temporal region of the skull. This placement could be performed either manually or with the assistance of a robot.

The surgical head model is prepared for vessel perfusion. Cannulated carotid arteries in the neck or the artery-mimicking tubes are connected to a reservoir containing dyed fluid with similar optical and acoustic properties to that of $HbO_2$. This fluid is perfused at a pressure of 80-120 mm Hg and a pulse rate of 60 beats/minute with a mechanical pump. A mock transsphenoidal surgery is performed. The external probe and the surgical head model are fixed for the duration of the surgery. An endoscope is placed to visualize the surgical field, and the drill is connected to a 3-axis translation stage. Before drilling, photoacoustic images are acquired as the drill and attached fiber are translated in a 2D plane orthogonal to the drill axis, above the sellar floor, within the 5-16 mm limits of the nostril size. Images are averaged to form 2D maps of vessel and bone locations.

In addition, photoacoustic images are acquired as the sphenoid bone is drilled Photoacoustic images are beamformed using amplitude- and coherence-based methods.

Brain tissue and bone have similar optical absorption spectra, as shown in FIG. 5. If laser penetration is sufficient to cause a photoacoustic response in brain tissues, the laser energy is lowered until the brain tissues are no longer visualized in the photoacoustic image. The carotid artery, which primarily carries $HbO_2$, is visualized separately when the fiber is closer by tuning the laser to approximately 900 nm, where the optical absorption of $HbO_2$ is orders of magnitude larger than that of bone. Then the two images are stitched together to visualize both bone and blood in the same image.

Figure 12:
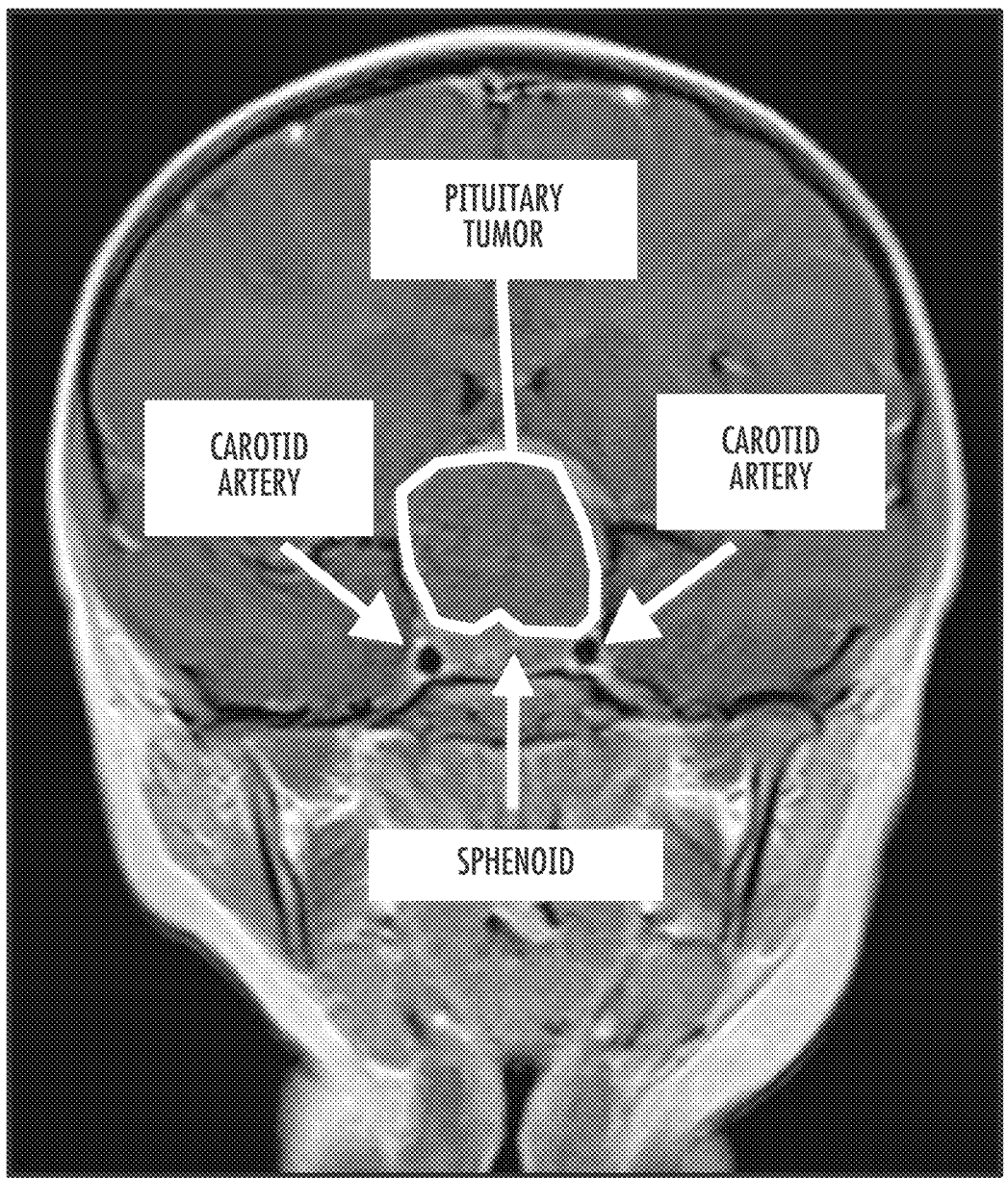
FIG. 12 illustrates an image of a sample coronal MRI of a patient.

The vessel-bone relationship in ex vivo photoacoustic images is compared to that of matched MRIs. FIG. 12 illustrates an image of a sample coronal MRI of a patient.

Using a similar experimental setup with the fiber placed for transsphenoidal light delivery in a cadaver head and a transducer placed on the temporal region of the cadaver's skull, the optical fiber is held with a passive arm. Photoacoustic images of the dyed ink that is perfused through the carotid arteries with a mechanical pump are acquired.

CT markers that align with the lateral dimension of the ultrasound probe are placed on the cadaver head. CT images are acquired for comparison with photoacoustic images.

An oblique slice that is registered to the externally-marked orientation of the ultrasound probe, is analyzed to measure distances in CT images. The photoacoustic images are evaluated with a custom-written computer program fixed on a non-transitory computer readable medium that segments the signals from vessel and bone and automatically measures the distance between the centroids of segmented signals. Segmentation is performed using thresholding of the photoacoustic images.

In addition, the optimized beamformers are tested and compared to more conventional beamformers using the phantom data and the cadaver data. The optimal performance metrics are used to evaluate images created with the optimized beamformers, compared to images obtained with conventional amplitude-based beamforming approaches (e.g. delay-and-sum, Fourier k-space).

Photoacoustic signals from the bone and blood may merge together as one, and it may be difficult to automatically segment the two different signals in photoacoustic images. This minimally affects surgical navigation, however as a contingency for distance verification measurements, two carotid arteries are used instead of one, to validate the accuracy of distances measured in the photoacoustic image.

The system can be used during a transsphenoidal surgery. Surgery proceeds as usual except prior to drilling the sella turcica (i.e the sphenoid bone closest to the pituitary) the optical fiber illuminates critical landmarks identified by the surgeon (e.g. sellar floor, tuberculum sellae, internal carotid arteries). Photoacoustic images and endoscopic images of the fiber locations are acquired with each fiber placement and correlated to the surgeon's expectations. In addition, the fiber is swept above the sellar floor in a 2D raster scan prior to drilling, and the resulting images are averaged to form a 2D map. The coherence-based photoacoustic images show a map of the carotid arteries that correlates with the surgeon's expectations based on endoscopic images. The probe can also be tracked in room coordinates. Preoperative CT or MR images and a navigation system can be used for probe placement.

Figure 13:
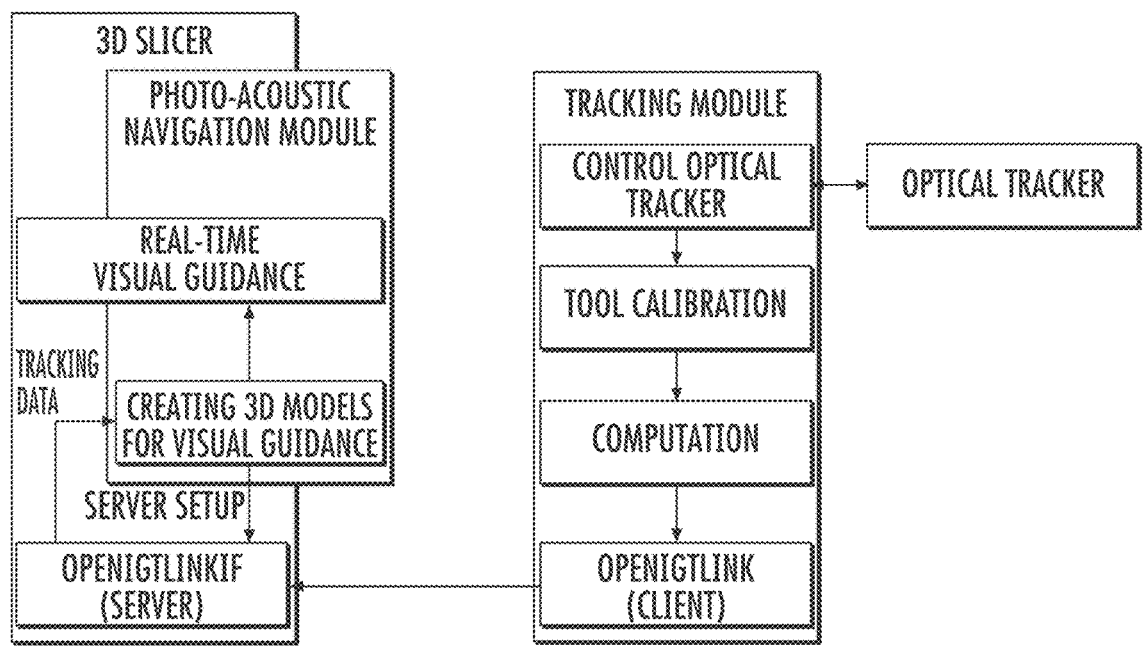
FIG. 13 illustrates a schematic diagram of an assistant system for photoacoustic imaging.

In another exemplary embodiment, the assistant system for photoacoustic imaging consists of the Tracking module and the Photoacoustic Navigation module, as shown in FIG. 13. FIG. 13 illustrates a schematic diagram of an assistant system for photoacoustic imaging.

Figure 14:
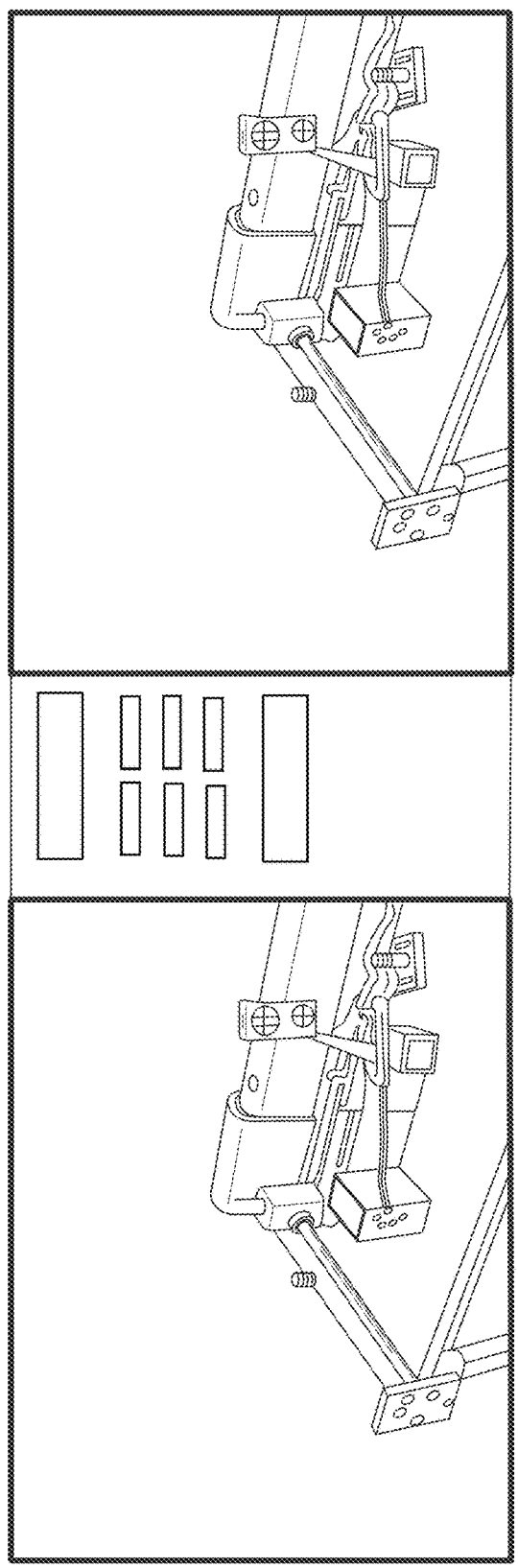
FIG. 14 illustrates images of a tracking module showing a GUI and left/right camera images.

The Tracking module, also shown in FIG. 14, acquires and processes data from an optical tracker, handles tool calibration, and sends the tracking information to the Photoacoustic Navigation module. FIG. 14 illustrates images of a tracking module showing a GUI and left/right camera images. It is implemented in C++ using the cisst libraries and the Surgical Assistant Workstation (SAW), which are open source software packages designed to ease the development of computer-assisted intervention systems. In particular, SAW includes components that interface to different tracking systems, including the Micron Tracker (Claron Technologies, Toronto, Canada), used for the experiments reported here.

The Tracking module is designed to track the position of three marker frames, attached to the laser, the ultrasound probe, and the patient. The patient-attached frame serves as the dynamic reference base (DRB); as in a typical navigation setup, this enables the system to track the laser and probe with respect to the DRB, thereby achieving robustness against motion of the patient or tracking camera. The Tracking module also includes methods for tool calibration. For the laser, this includes a non-contact pivot calibration method where a visible laser beam is directed to intersect a physical point in the workspace from different orientations.

Figure 15A:
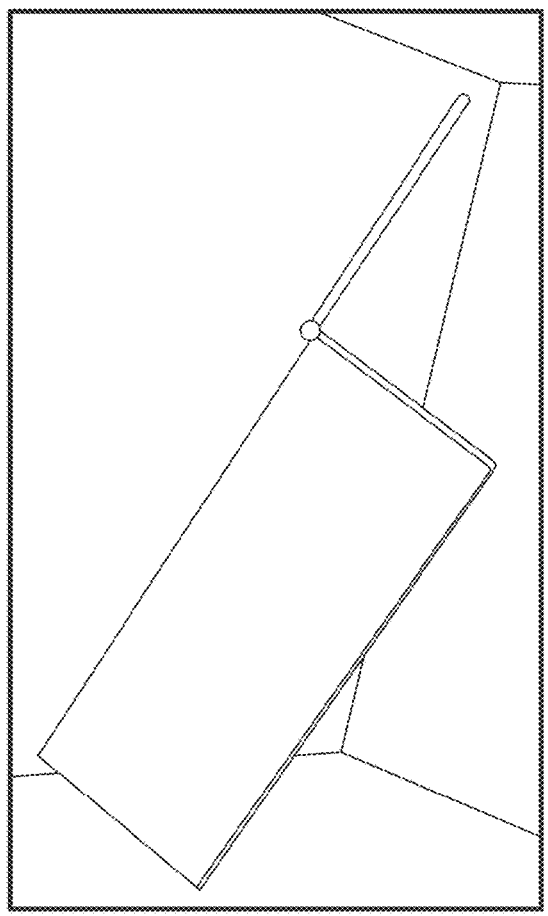
FIGS. 15A and 15B illustrate graphical representations of 3D models for presenting ultrasound probe and image plane (15A) and a virtual laser path (15B).
Figure 15B:
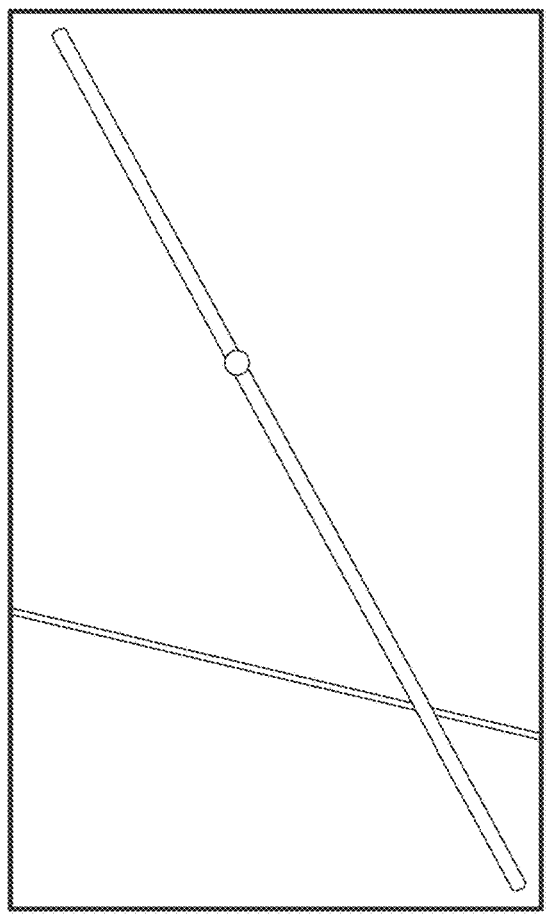

The Photoacoustic Navigation module is a plugin module, written in Python, that is integrated with 3D Slicer and provides visual guidance using the data from the Tracking module. Although implemented as two separate programs with an OpenIGTLink network interface used for data exchange between the programs, it is possible to combine all functionality into a single module within 3D Slicer. The Photoacoustic Navigation module includes 3D models of the ultrasound probe, laser tip, ultrasound plane, and virtual laser path. The probe and laser tip are represented as standard Slicer locator probes (see FIGS. 15A and 15B); these can be replaced by CAD models. The ultrasound plane from the linear transducer is represented by a 3D rectangle and the virtual laser path is represented by a cylinder, as shown in FIGS. 15A and 15B. FIGS. 15A and 15B illustrate graphical representations of 3D models for presenting ultrasound probe and image plane (FIG. 15A) and a virtual laser path (FIG. 15B).

Figure 16B:
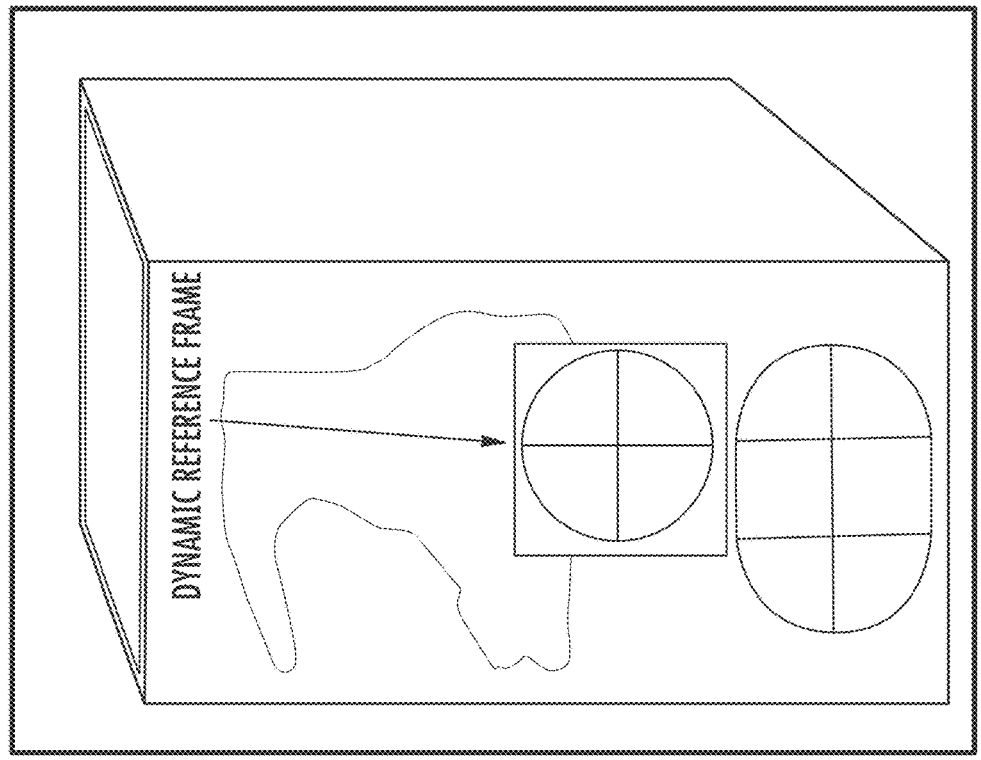
FIGS. 16A and 16B illustrate images of a phantom embedded with thin bones, spherical rubber targets, and a rubber rod.
Figure 16A:
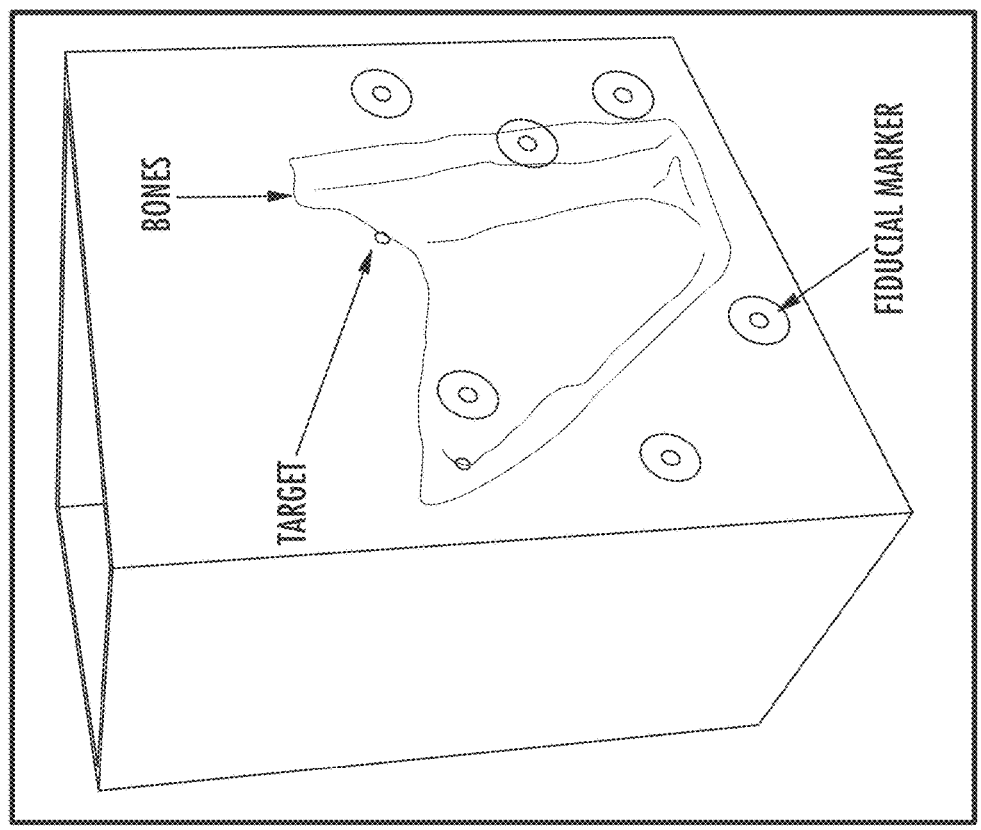

Two thin bones and four spherical rubber targets were placed in a gelatin material, as shown in FIGS. 16A and 16B. FIGS. 16A and 16B illustrate images of a phantom embedded with thin bones, spherical rubber targets, and a rubber rod. The size of phantom is 60×100×80 mm. The bones were obtained from a lamb skull and have thicknesses of 1.7 and 2.5 mm. The spherical rubber targets are 2.3 mm in diameter. In addition, 17 fiducial markers were attached to the surface of the plastic container to faciliate registration. Finally, a dynamic reference base (DRB) is fixed on the phantom to compensate for unexpected motion of the phantom or tracking camera. The phantom was CT scanned by the Small Animal Radiation Research Platform (SARRP, Xstrahl Ltd, Surrey, U.K.). The dimension of the CT volume is 216× 384×256 pixel, with a voxel size of 0.5×0.5×0.5 mm.

A SonixTouch ultrasound scanner, with an Ultrasonix L14-5W/60 linear transducer, was used for the experiment. This transducer has a 5-14 MHz bandwidth (a lower frequency probe would be preferable for transcranial imaging). For the photoacoustic imaging, a 1 mm core diameter optical fiber with a 0.37 mm numerical aperture was coupled to a 1064 nm Nd:YAG laser.

Marker frames were attached to the ultrasound transducer (probe), laser tip holder, and phantom. The marker frame on the phantom was used as the dynamic reference base (DRB).

Figure 17:
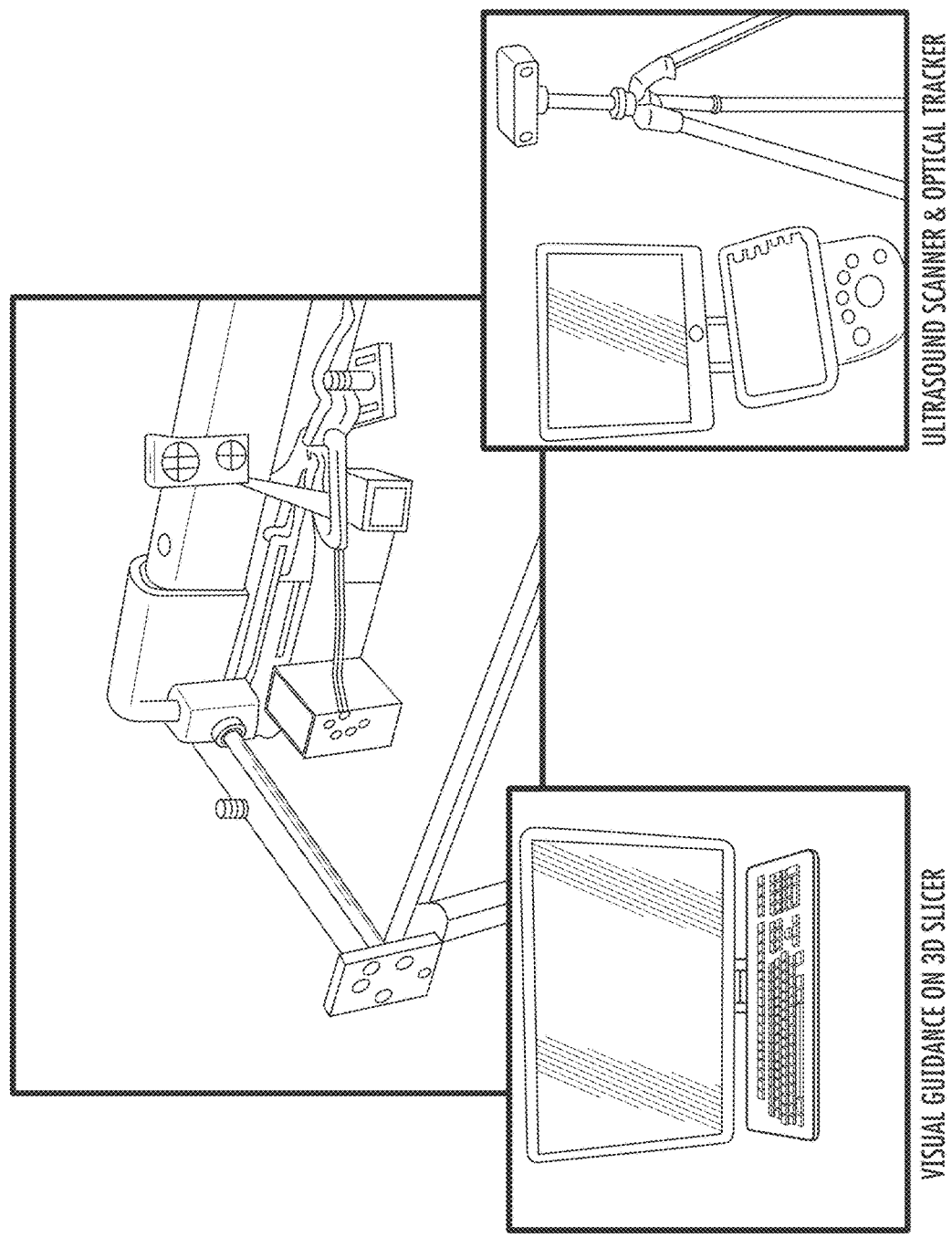
FIG. 17 illustrates images of an experimental setup for a photoacoustic imaging assistant system according to an embodiment of the present invention.

The phantom was placed beside the laser of the photoacoustic imaging system. The Micron Tracker was placed so that its field of view encompassed the entire scene of the experimental setup (FIG. 17). FIG. 17 illustrates images of an experimental setup for a photoacoustic imaging assistant system according to an embodiment of the present invention. The Tracking and Photoacoustic Navigation modules were installed on a laptop near the experimental setup.

After the optical fiber was fixed on the laser tip holder, three calibration procedures were conducted. First, the application provided by the manufacturer (Claron Technologies) was used to estimate the tool tip offset and the direction matrix of the tool tip. Second, the accuracy of the tool tip offset was confirmed via a standard pivot calibration method. Finally, the direction of the laser path was confirmed by using a non-contact pivot calibration method, where the laser spot was aimed at a fixed point in the workspace from different tool orientations.

Experiments were conducted to evaluate the localization accuracy of the assistant system for photoacoustic imaging. Two of the spherical rubber balls were selected as targets. The 2.5 mm bone was located between the ultrasound transducer and target, and the 1.7 mm bone was located between the laser tip and target.

After setting up all devices and applications, and before fixing the optical fiber to the optical fiber holder, the tracking system was registered to the preoperative CT image. This registration was accomplished by touching the fiducials affixed to the phantom with a tracked pointer (i.e., the optical fiber holder) and performing a paired-point registration between the fiducial positions measured by the tracker and their corresponding positions in the CT image. Because the dynamic reference base was attached to the phantom, it is not necessary to repeat the registration procedures if the phantom or tracking camera is repositioned.

The ultrasound transducer and laser tip were placed using the visual guidance information displayed in 3D Slicer. B-mode and photoacoustic ultrasound images of the two targets were acquired.

Figure 18:
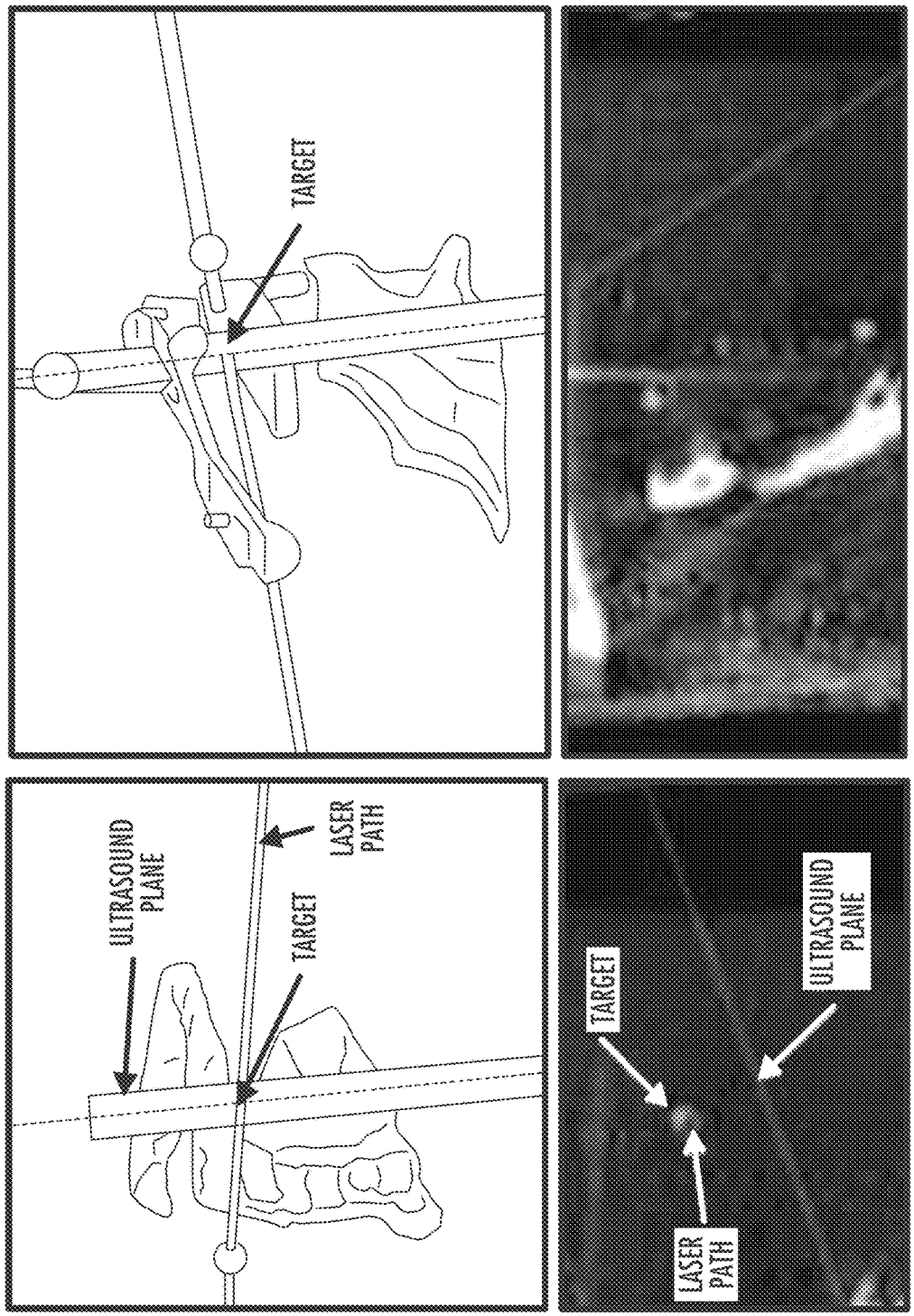
FIG. 18 illustrates images of screenshots for targets and CT cross-sections indicating US image plane and laser beam for targets.

FIG. 18 illustrates images of screenshots for targets and CT cross-sections indicating ultrasound (US) image plane and laser beam for targets. Annotated screenshots of the Photoacoustic Assistant module (e.g., the 3D view from 3D Slicer) are shown in the top row of FIG. 18. The bottom row of this figure shows a cross-section of the CT image, with annotations for the ultrasound image plane and the intersection of the virtual laser path. FIG. 18 shows that the ultrasound plane and virtual laser path are close to the targets, though small errors are evident.

Figure 19:
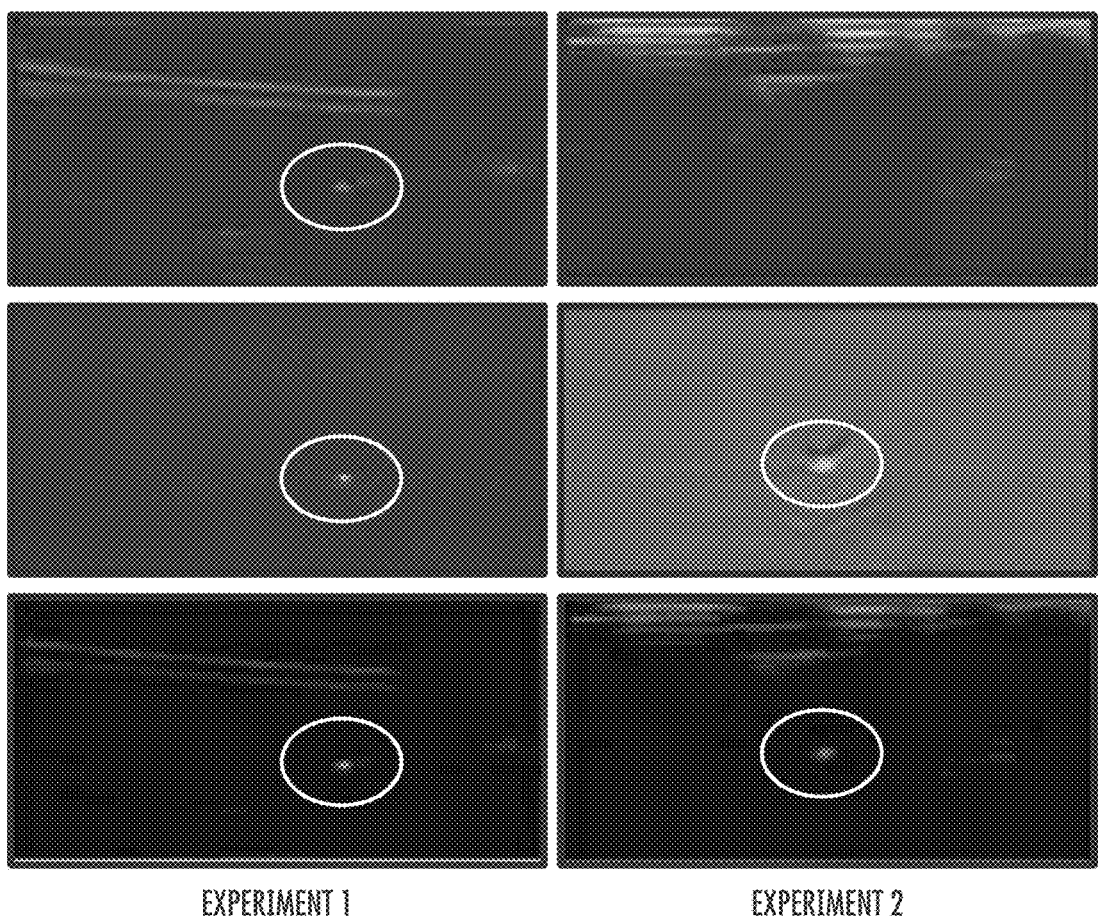
FIG. 19 illustrates photoacoustic imaging results for the targets, B-mode images (top), photoacoustic images (middle) and overlaid images (bottom).

The first target was visible on both B-mode and photoacoustic images, whereas the second target was only visible in the photoacoustic image (see FIG. 19). FIG. 19 illustrates photoacoustic imaging results for the targets, B-mode images (top), photoacoustic images (middle) and overlaid images (bottom). Circles indicate the target. The photoacoustic images and tracking data were used to evaluate two aspects: (1) the user's ability to follow the visualization guidance, and (2) the accuracy of the tracking system's localization of the target.

The user's ability to follow the visualization guidance is evaluated by computing the intersection of the laser path (3D line) with the ultrasound plane and comparing this intersection point to the target. The intersection point indicates where the user actually aimed the laser and probe; in the ideal case, this would coincide with the target. The error was 1.49-1.53 mm. Both the laser and US probe were hand-held in these experiments; in a setup where one or both of these devices is controlled by a robot, the targeting error should be even lower.

The second analysis focuses on the accuracy of the tracking system to localize the target, which is quantified by measuring the distance between the image origin and the target. In the photoacoustic image, the target appears as a spot and can be easily expressed in US image coordinates (i.e., with respect to the image origin). This point can also be obtained (with more computation) by locating the target in the CT image, using the registration to transform this position into tracking system coordinates, and then using the probe calibration to transform it to the US image coordinates. Table I shows the results, expressed in ultrasound image coordinates (axial and lateral) as well as an overall distance. These results indicate a discrepancy, primarily in the axial direction, between the two measurement methods.

TABLE I

TARGET LOCALIZATION: NAVIGATION VS. PHOTOACOUSTIC IMAGE

|  |  | Target 1 | Target 2 |
|---|---|---|---|
| Target position from navigation data, mm | Axial | 28.85 | 28.41 |
|  | Lateral | 37.93 | 28.42 |
| Target position from photoacoustic image, mm | Axial | 20.71 | 19.67 |
|  | Lateral | 36.80 | 28.98 |
| Differences, mm | Axial | 8.13 | 8.74 |
|  | Lateral | 1.13 | 0.56 |

This study focused on the development and experimental evaluation of a navigation system to guide the placement of a laser and/or ultrasound probe to obtain photoacoustic ultrasound images during endonasal skull base drilling. The ultimate goal is to use the photoacoustic images to provide real-time measurement of the location of critical structures, such as the carotid artery, with respect to the drill tip. In one envisioned scenario, the laser and drill are mounted on a robot system which can use this information to dynamically construct or adjust virtual fixtures to protect the critical anatomy. In this case, the navigation system would primarily be used to position the ultrasound probe, though it could also provide guidance to the surgeon (or robot) to make minor adjustments to the drill (laser) orientation to gain additional image information.

The experiments demonstrated that the developed navigation system is effective in enabling the user to align the laser and probe to obtain a photoacoustic image of a desired target. Here, the target is identified on a preoperative CT image, which is registered to the intraoperative (tracker) coordinate system. The results from the first experiment indicated that the user could follow the visual guidance with an accuracy of approximately 1.5 mm, which appears to be sufficient to capture the target in the photoacoustic image in the presence of registration and tracking errors Table I shows a large discrepancy between the target measured by the photoacoustic image and the tracking system. Most of this discrepancy is in the axial direction (in ultrasound image coordinates), which was 8.13 mm and 8.74 mm for targets 1 and 2, respectively. The tracking system measurement is affected by errors in the probe calibration, tracking system, and registration. The photoacoustic measurement is affected by speed of sound errors and acoustic inhomogeneities. The bone thickness may be measured on the CT image and used to minimize the impact of these effects.

The influence of the navigation system inaccuracies is reduced by directly measuring the distance from the cutter tip (or the bone surface) to the target anatomy on the photoacoustic image. Because the laser line is calibrated with respect to the drill, this distance measurement would indicate how far the drill is from the critical structure. For this method, the ultrasound probe should be oriented so that the image plane is aligned with the laser line, rather than perpendicular to it as in the experiments reported here.

Figure 20:
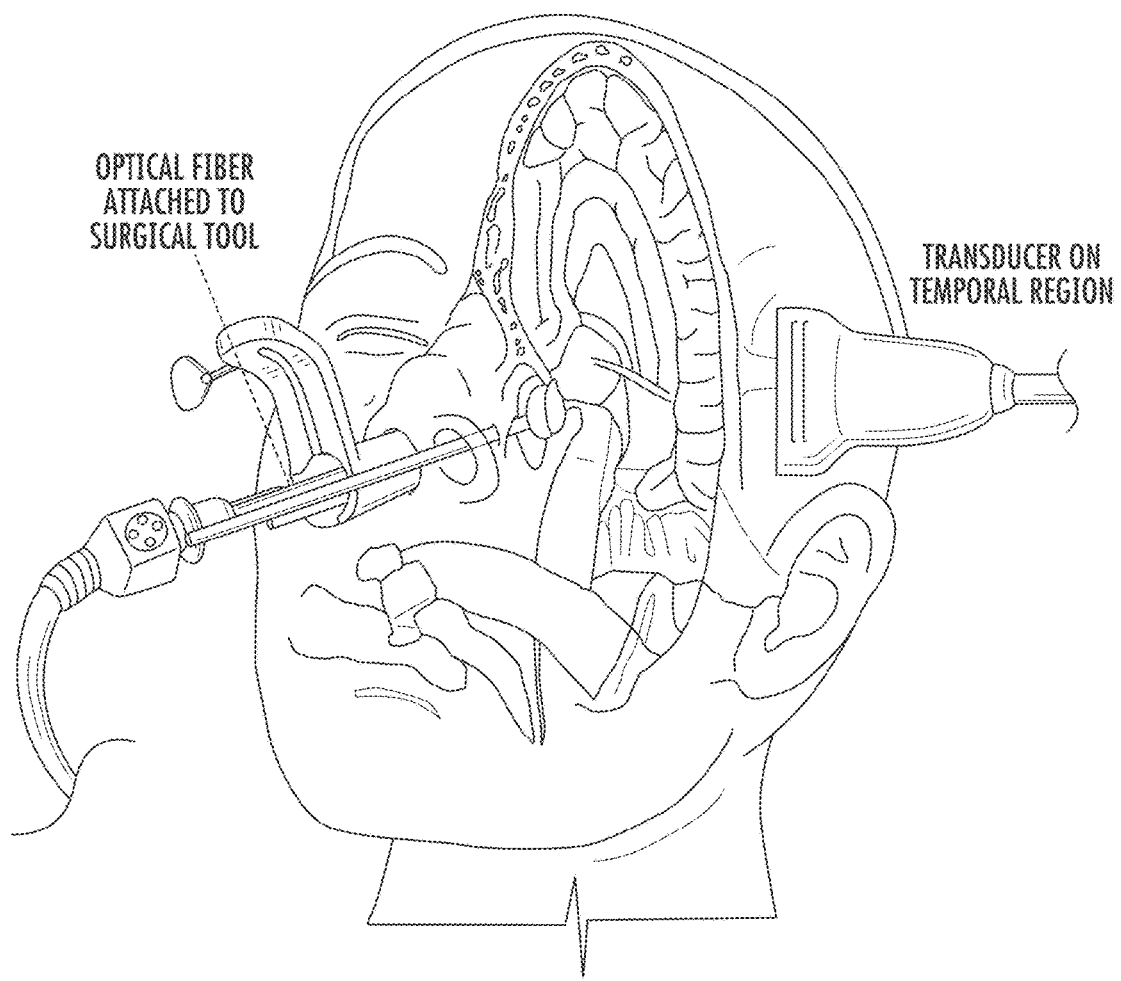
FIG. 20 illustrates an exemplary photoacoustic system for detecting a pressure field with an external ultrasound probe.

In another exemplary embodiment, a navigation system was integrated with a robot to enforce virtual fixtures that avoid critical areas defined on preoperative CT images. FIG. 20 illustrates an exemplary photoacoustic system for detecting a pressure field with an external ultrasound probe. One limitation of this system (and navigation systems in general) is that it relies on a single registration between the preoperative CT image and the intraoperative coordinate system with reported errors up to 3 mm. Better accuracy is required. In addition, patient motion and tissue deformation can reduce accuracy over time.

To overcome these limitations, the navigation system can be integrated with the photoacoustic system. The robot-held ultrasound probe and surgical tools are tracked relative to the intraoperative reference frame. A major limitation, however, is that the detected photoacoustic signal could be located wherever the light scatters after passing through bone and surrounding tissue. Thus, a method to localize vessel centers relative to the fiber axis is necessary for real-time definition of virtual fixtures.

This work investigates an image-based approach to estimate the fiber and vessel positions regardless of the limited tracking accuracy or the light distribution within tissue. The relationship between contrast and fiber position is first elucidated, then utilized to determine unknown fiber positions relative to vessel locations in the photoacoustic image.

For typical sizes of the carotid arteries (3.7-8.0 mm), only the boundaries are expected to be visible due to factors such as the bandwidth of transcranial probes, the presence of skull (which both attenuate the higher-frequency photoacoustic signals), and the limited angle probe view. Therefore, two contrast measurements (one from each boundary) may be obtained from each image acquired as the fiber is translated in equal increments across the sellar region. This region may be obtained from preoperative CT images or surgeon experience with suspected vessel locations. The difference between the two contrast measurements would then become calibration points that vary with the known fiber translation.

After obtaining these calibration points, any image with an uncertain fiber position can be used to calculate the contrast difference of vessel boundaries. This contrast difference may be used to estimate the fiber position, by first selecting calibration points that neighbor the measured contrast difference and applying least-squares linear regression to this subset of calibration points. The equation for the best fit line can then be solved to find the estimated fiber position.

A black, cylindrical, vessel-like target with a diameter of 3.5 mm and a 1 mm-thick bovine marrow bone cut to dimensions of 1.2 cm×1.8 cm were embedded in a plastisol phantom during the phantom fabrication process. A 1 mm core diameter optical fiber (0.37 numerical aperture) was coupled to a 1064 nm Nd:YAG laser and affixed to a manual translation stage. The absence of optical or acoustic scatterers enabled visual alignment of the fiber with the center of the bone, vessel, and transducer, and the fiber was placed in this initial position, approximately 1 mm above the phantom surface.

Figure 21:
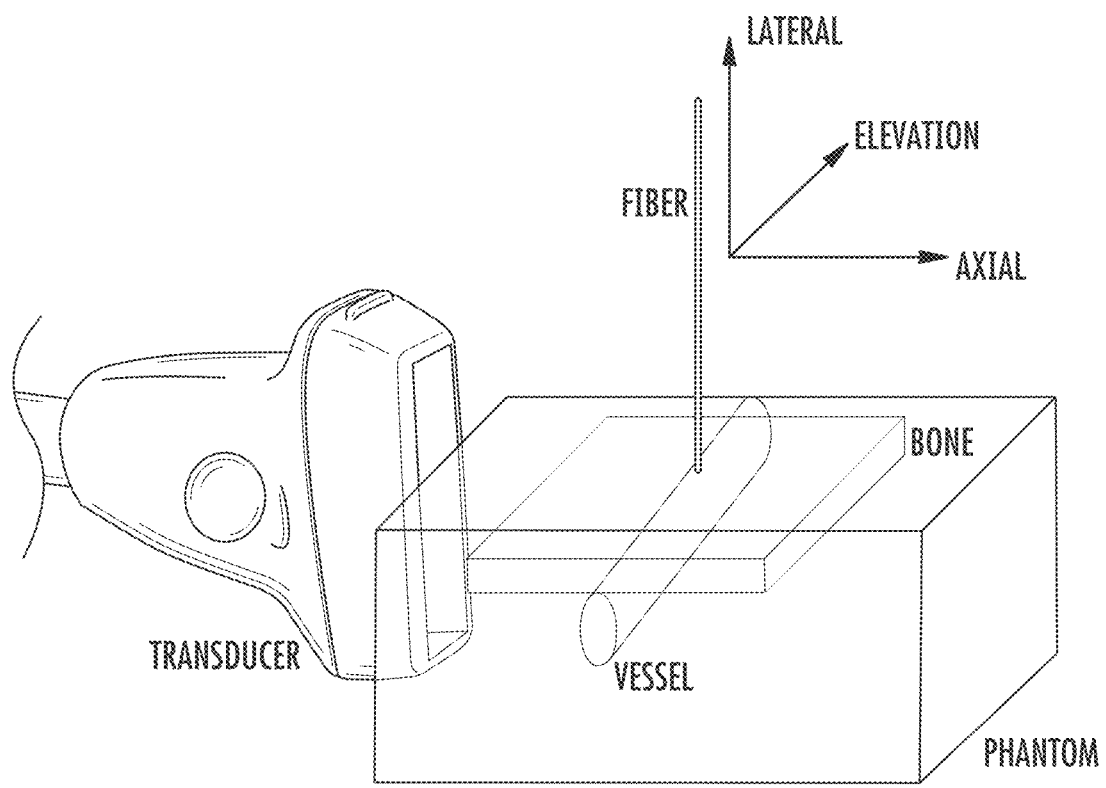
FIG. 21 illustrates a schematic diagram of an experimental setup illustrating fiber translation directions, according to the exemplary embodiment of the invention.

An Ultrasonix L14-5W/60 linear transducer (Richmond, BC, Canada) with a bandwidth of 5-14 MHz was placed with the long axis of the vessel perpendicular to the axial dimension of the probe. This probe was connected to a SonixTouch ultrasound scanner, and a SonixDAQ data acquisition unit was triggered by the flashlamp output signal of the laser to access raw, pre-beamformed radiofrequency photoacoustic data. The fiber traversed the axial, lateral, and elevational probe dimensions, as illustrated in FIG. 21, in 0.3 mm increments from the initial position, within the dimension limits of the sphenoid sinus. Ten images were acquired with each translation. FIG. 21 illustrates a schematic diagram of an experimental setup illustrating fiber translation directions, according to the exemplary embodiment of the invention.

Images were reconstructed with a delay-and-sum beamformer, and the resulting target contrast was measured as: Contrast=20 $\log_{10}$ ($S_i/S_o$), where $S_i$ and $S_o$ are the means of the image data within regions of interest (ROIs) located inside and outside of the target, respectively. Two ROIs were defined in one image by searching for the maximum signals within the expected proximal and distal boundary locations, surrounding each signal with a 0.4 mm (axial)×1.9 mm (lateral) rectangle, and automatically creating same-sized noise ROIs at the same depths, located approximately 1 mm from the left edge of the signal ROIs. All subsequent images used the same ROI positions.

The first half of acquired data from each fiber translation were used to create the initial calibration points, while the remaining half were placed in the "unknown" fiber position category. The two contrast measurements from each fiber position in this second category were averaged and subtracted to obtain contrast difference measurements. Fiber positions were estimated by applying the method described above to the range of known fiber translations for calibration points within 0.5 dB of the measured contrast difference values. Estimates were then compared with the ground truth.

Figures 22A, 22B, 22C:
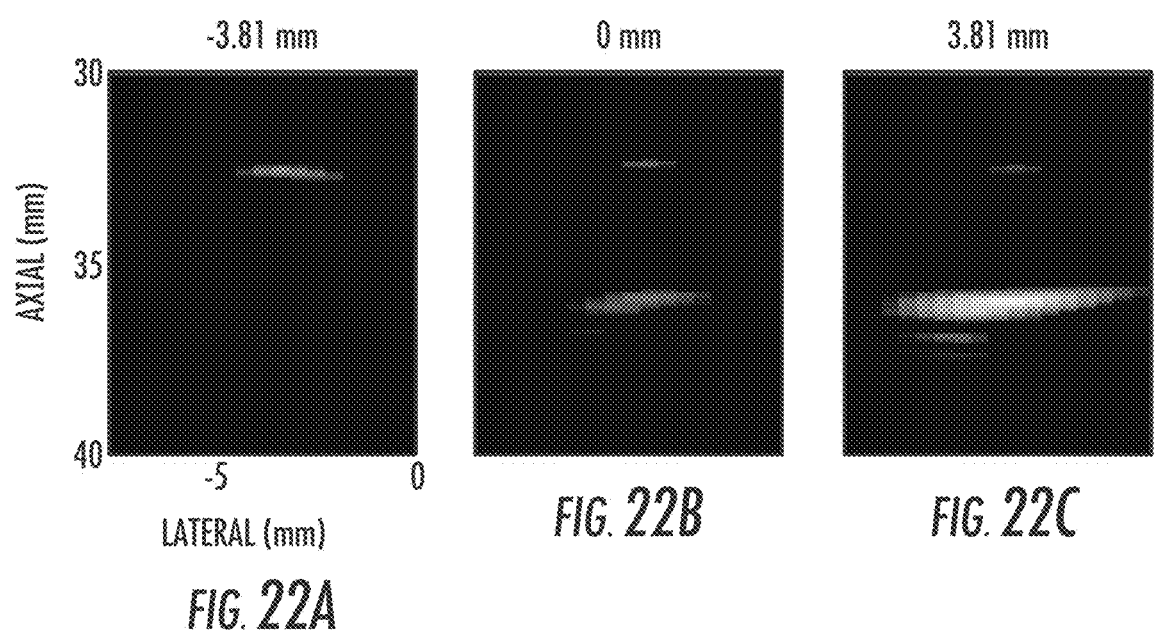
FIGS. 22A-22C illustrate photoacoustic images of the proximal (FIG. 22A), distal (FIG. 22C) and both (FIG. 22B)

Photoacoustic images of the target boundaries are shown in FIGS. 22A-22C. FIGS. 22A-22C illustrate photoacoustic images of the proximal (FIG. 22A), distal (FIG. 22C) and both (FIG. 22B) vessel boundaries as the fiber was translated by an axial distance noted above each figure. The scale applies to all images with distances defined relative to the probe. All images are shown with 20 dB dynamic range. The axial fiber position relative to the vessel center is indicated above each image. All images are taken from the same image location, defined relative to the probe.

Contrast values measured as the fiber was translated in the three dimensions indicated in FIG. 21 are shown in FIGS. 23A-23C, relative to the probe dimensions. FIGS. 23A-23C illustrate graphical views of mean contrast as a function of fiber translation in the axial (FIG. 23A), elevation (FIG. 23B), and lateral probe dimensions (FIG. 23C). Error bars represent±one standard deviation of five measurements. In all cases, the mean contrast of the proximal and distal vessel boundaries at 0 mm is approximately 21-24 dB, indicating that the manual translation stage sufficiently returned the fiber to its initial position (i.e. within 3 dB contrast error), and the vessel boundaries had <3 dB mean contrast difference at this fiber position.

The mean contrast difference between the two boundaries changes by up to 4 dB along the length of the vessel, as shown in FIG. 23A. This minimal change indicates that the fiber does not have to be in the same plane as the photoacoustic image to visualize the vessel and obtain contrast measurements.

FIG. 23B shows similarly minimal change in mean contrast measurements (<6 dB) as the fiber moves within 4 mm from the phantom surface, indicating that the fiber position in this probe dimension minimally affects the fiber position estimator. Note that translation in this dimension increases the surface area of light incident on the target, particularly for larger vessels, given the conical light profile. Translation in this dimension could therefore decrease the fluence incident on the bone as the fiber moves away from the phantom.

The greatest change is observed with axial translation as shown in FIG. 23C, where the mean contrast difference between the proximal and distal vessel boundaries varies by up to 14 dB with each fiber translation. The change also appears to be somewhat symmetrical about the initial translation position, with larger differences occurring in either direction from this initial position, likely due to the symmetry of the vessel.

The difference in contrast measurements (distal vessel boundary minus proximal vessel boundary) with axial fiber translation is shown in FIG. 24. FIG. 24 illustrates a graphical view of calibration points shown along with one measurement from the test set along with the "unknown" fiber position that was estimated and compared with the ground truth location illustrated in the plot. The difference is approximately 0 dB when the fiber is centered on the vessel (i.e. 0 mm translation), negative for translations toward the probe, and positive for translations away from the probe. These differences comprise the calibration points that can be obtained during surgery by sweeping the fiber across the expected location of a carotid artery. These calibration points are then used as an input for the fiber position estimator described in Section 2. An example of one contrast difference measurement (7.6 dB) is shown as a horizontal line in FIG. 24. The corresponding "unknown" fiber location was estimated as 1.29 mm after linear regression of the points enclosed in the box in FIG. 24. The true location was 1.27 mm.

The estimated distances for thirty measurements are plotted as a function of the true distance in FIG. 25. FIG. 25 illustrates a graphical view of estimated versus true distance for thirty fiber positions with the diagonal line indicating the ideal 1:1 relationship. Deviations from the diagonal line, representing the ideal relationship between true and estimated values, increase with distance from the vessel center. This increased error can be attributed to the larger variance of the calibration points farther away from the vessel center observed in FIGS. 23A and 24. The RMS error for the proposed estimator within 1, 2, 3, and 4 mm from the vessel center is 0.38, 0.61, 0.62, and 0.68 mm, respectively.

A novel method to recover fiber positions relative to vessel centers based on image contrast measurements was investigated. RMS errors increased with distance from the vessel center, ranging from 0.38 mm to 0.68 mm. Accurate knowledge of tool position in the lateral dimension of the probe (see FIG. 21) is additionally required to avoid injuries. The ability to detect vessels in this dimension is limited by the lateral resolution of the imaging system which is approximately 0.06-0.19 mm in the experiments and at most 0.1-3 mm depending on the vessel distance from the external probe (i.e. 32-77 mm), transducer bandwidth and aperture size, and optical diffraction limit. Visibility in both the axial and lateral dimensions define the accuracy for detecting vessel centers and defining virtual fixtures based on the proposed method. Reported errors are sufficient, as they are within the minimum separation of 4 mm between the carotid arteries in the sellar region.

Similar vessel contrast occurs when the fiber is located along a vessel, up to 4 mm from the center of the image plane (i.e. the elevation probe dimension) as shown in FIG. 23A. Thus, perfect fiber alignment with the image plane is not required to achieve suitable results with the proposed method. In addition, the vessel does not have to be perpendicular to the fiber. It may tilt away from the fiber (which is expected given the complex anatomy of the internal carotid arteries) without significantly affecting fiber contrast, as demonstrated in FIG. 23B.

Fiber translation, position calibrations, and vessel boundary contrast measurements can be combined to compensate for the loss of tracking accuracy. The proposed method is promising for surgeons to visualize carotid arteries, estimate proximity, and thereby avoid injury.

In another exemplary embodiment, the main components of the system are a surgical drill, pulsed laser, ultrasound probe and scanner, and navigation (tracking) system. The navigation system determines the spatial relationships between the drill (and laser beam), ultrasound probe, and patient. Ultimately, the drill is preferably to be mounted on the end of a robot, which is either teleoperated or cooperatively-controlled by the surgeon. The ultrasound probe could be held by a second robot or by a passive arm. The resulting system consists of several different coordinate systems and thus requires determination of the intervening transformations, as illustrated in FIG. 26. FIG. 26 illustrates a schematic diagram of major components, coordinate frames and transformations for an implementation of a navigational and photoacoustic system, according to an embodiment of the present invention. The optical tracking system measures several of these transformations, but other transformations are obtained by calibration or registration procedures. The registration between the phantom coordinate system and the (optically-tracked) dynamic reference base (DRB) is obtained by using a tracked pointer to touch fiducials on the phantom, followed by a paired-point registration between these measured points and the coordinates of the points in the CAD model of the phantom (for a patient, a CT scan would be used instead of a CAD model). The transformation between the (optically-tracked) marker frame on the US probe and the US image plane is obtained by a calibration method that uses an active point phantom. The offset (translation) between the (optically-tracked) marker frame on the tool (drill) and the tool tip is obtained by a standard pivot calibration method. The laser line is calibrated with respect to the tool marker frame using the method described below (Tracking module).

The transformation map shown in FIG. 26 supports three methods for computing the target with respect to the reference frame, PDRB, where BTA denotes the transformation from coordinate frame A to coordinate frame B and PC is the target measured with respect to coordinate frame C:

1) The target point (in CAD model) can be transformed to the reference frame using the registration:

$$P_{DRB} = {}^{DRB}T_{CAD} P_{CAD} \quad (7)$$

2) If the target is visible in the PA image, it can be transformed from US image coordinates to the reference frame using the US probe calibration and the tracker measurements of the marker frames attached to the US probe and DRB:

$$P_{DRB} = {}^{CAM}T_{DRB}{}^{-1} {}^{CAM}T_{PRB} {}^{PRB}T_{US} P_{US} \quad (8)$$

3) If the target is visible in the PA image, its position is computed from the intersection of the laser line with the US image plane:

$$P_{DRB} = {}^{CAM}T_{DRB}{}^{-1} {}^{CAM}T_{TL} {}^{TL}T_{OF} P_{OF} \quad (9)$$

where $P_{OF}$ is the intersection point expressed in the optical fiber (OF) coordinate system. In the experiments, the first method is used as the "ground truth". In a surgical scenario, this option may not be available if the critical structure (e.g., carotid artery) is not directly visible in the CT image. The second method is the most obvious approach, but the third method is proposed because it is less dependent on accurate measurements from PA-US. It does depend on accurate calibration of the laser line, which is easier to guarantee if the optical fiber is integrated with the tool. In the best case, if the laser can itself be the tool (i.e., if the laser is used for cutting), there would be zero error in the calibration. This approach essentially discards the position of the target in the PA image (i.e., it only cares whether or not the target is visible). One issue, however, is that this method is affected by divergence of the laser beam, which can be significant for an uncollimated fiber. But, this effect can be mitigated by sweeping the laser across the target and identifying the edges.

The software architecture consists of the Tracking module, Imaging module for B-mode or photoacoustic imaging, and the Photoacoustic Navigation module, as shown in FIG. 27. FIG. 27 illustrates a graphical view of a system overview for an assistant system for photoacoustic imaging. FIG. 27 is also a variation on FIG. 13, discussed above, but adds an imaging module to the tracking module and photo-acoustic navigation module.

The Tracking module acquires and processes data from an optical tracker, handles tool calibration, and sends the tracking information to the Photoacoustic Navigation module. It is implemented in C++ using the cisst libraries and the Surgical Assistant Workstation (SAW), which are open source software packages designed to ease the development of computer-assisted intervention systems. In particular, SAW includes components that interface to different tracking systems, including the Atracsys Tracker (Atracsys LLC, Switzerland), used for the experiments reported here (FIGS. 28A-28D). FIGS. 28A-28D illustrate images of optical tracker and tracking tools (FIG. 28A Optical Tracker, FIG. 28B Dynamic Reference Base attached to the phantom, FIG. 28C optical fiber holder, FIG. 28D marker frame attached to the ultrasound transducer).

The Tracking module is designed to track the position of three marker frames, attached to the laser, the ultrasound probe, and the patient. The patient-attached frame serves as the dynamic reference base (DRB); as in a typical navigation setup, this enables the system to track the laser and probe with respect to the DRB, thereby achieving robustness against motion of the patient or tracking camera. The Tracking module also includes methods for tool calibration. For the laser, this includes a non-contact pivot calibration method where a visible laser beam is directed to intersect a physical point in the workspace from different orientations.

The Photoacoustic Navigation module is a plugin module, written in Python, that is integrated with 3D Slicer and provides visual guidance using the data from the Tracking module. While it would have been possible to combine all functionality into a single module within 3D Slicer, for convenience they were implemented as two separate programs and the OpenIGTLink network interface was used for data exchange between the programs.

The Photoacoustic Navigation module includes 3D models of the ultrasound probe, laser tip, virtual laser path, and realtime ultrasound image plane. The probe is represented by a 3D CAD model of the ultrasound transducer and the laser tip is represented by a standard Slicer locator probe (see FIGS. 29A-29C). The real-time ultrasound image plane shows real-time images received from the Imaging module and the virtual laser path is represented by a cylinder, as shown in FIGS. 29A-29C. FIGS. 29A and 29B illustrate a perspective view of an ultrasound probe model and real time ultrasound imaging; FIG. 29C illustrates a schematic diagram of a laser tip and virtual laser path.

The Imaging module has two implementations, one for B-mode ultrasound and one for photoacoustic (PA) imaging, and is installed on the ultrasound scanner and PA imaging system, respectively. It is implemented in C++ using the MUSiiC toolkit and can provide real-time B-mode or PA ultrasound images via an OpenIGTLink network interface. Although the proposed system relies exclusively on PA imaging, B-mode imaging was used for some of the validation experiments.

A phantom to evaluate the accuracy of the system was created and is illustrated in FIGS. 30A-30D. FIG. 30A illustrates a phantom embedded with an inner structure for B-mode imaging. FIG. 30B illustrates a CAD model of the inner structure of the device of FIG. 30A. FIG. 30C illustrates the phantom of FIG. 30A embedded with additional spherical rubber targets, and FIG. 30D illustrates a CAD model of the inner structure of FIG. 30C. The inner structure was designed with the Solidworks 2013 (Dassault Systemes SolidWorks Corp., Concord, Mass., USA), 3D CAD software and manufactured with a 3D printing machine. This structure contains 5 square pillars of different heights, each used as groundtruth landmarks. The top of each pillar has a hemi-spherical concavity to facilitate registration and to place spherical rubber targets for the photoacoustic imaging. The size of the inner structure of the phantom is 60×25×25 mm and the size of plastic container is 100×60×100 mm. The inner structure was fixed in the plastic container and the dynamic reference base (DRB) was fixed on the surface of the plastic container to compensate for unexpected motion of phantom or tracking camera. During the experiments, the phantom was filled with water for ultrasound and photoacoustic imaging. After the registration procedure and experiment with ultrasound images, two spherical rubber targets (2.3 mm diameter) were fixed atop two of the pillars, which had a 10 mm height difference. The navigation assistant used the 3D CAD model, in STL format, rather than a CT scan.

The model was displayed in the 3D view of 3D Slicer and used for the registration. Note that this phantom does not contain any bone, so it enables performance of experiments with both B-mode and PA ultrasound imaging.

A SonixTouch ultrasound scanner, with an Ultrasonix L14-5W/38 linear transducer, was used for the experiments. This transducer has a 5-14 MHz bandwidth. For the photoacoustic imaging, a 1 mm core diameter optical fiber with a 0.37 mm numerical aperture was coupled to a 1064 nm Nd:YAG laser. Image data was obtained from the Imaging module with OpenIGTLink network interfaces. The ultrasound and photoacoustic images were displayed with the ultrasound transducer model, laser tip model and virtual laser path model on the 3D view of the 3D Slicer in real-time.

Marker frames were attached to the ultrasound transducer (probe), laser tip holder, and phantom, as illustrated in FIG. 26. The marker frame on the phantom was used as the DRB. To hold and move the ultrasound transducer, a UR5 robotic arm (Universal Robots Inc., Odense, Denmark) was applied to reduce subtle hand-related motions of the transducer during image acquisition and to move very precisely.

The phantom was placed beside the laser of the photoacoustic imaging system, and the optical fiber was fixed on the holder. The tracking camera was placed so that its field of view encompassed the entire scene of the experimental setup, as shown in FIG. 31. FIG. 31 illustrates images of an experimental setup according to the exemplary embodiment of the invention. The Tracking and Photoacoustic Navigation modules were installed on a laptop near the experimental setup.

After the optical fiber was fixed on the laser tip holder, three calibration procedures were conducted. First, the tool tip offset and the direction matrix of the tool tip were estimated using manual procedures. Second, the accuracy of the tool tip offset was confirmed via a standard pivot calibration method. Finally, the direction of the laser path was confirmed by using a non-contact pivot calibration method, where the laser spot was aimed at a fixed point in the workspace from different tool orientations.

Two different experiments were conducted to evaluate the accuracy of the assistant system for photoacoustic imaging. The first experiment uses B-mode imaging to evaluate the navigation accuracy of the experimental setup. The second experiment evaluates the accuracy of real-time measurement with the photoacoustic image, using the registered CAD model as the ground-truth. B-mode images were collected in this setup for comparison; although B-mode imaging is not ideal for the intended skull base surgery application (due to the bone), it may be applicable to procedures elsewhere in the body.

After setting up all devices and applications, and before fixing the optical fiber to the optical fiber holder, the tracking system was registered to the 3D CAD model. This registration was accomplished by touching the fiducials of the phantom with a tracked pointer (i.e., the optical fiber holder), and performing a paired-point registration between the fiducial positions measured by the tracker and their corresponding positions in the 3D CAD model. Because the dynamic reference base was attached to the phantom, it is not necessary to repeat the registration procedures if the phantom or tracking camera is repositioned.

For the first experiment, the ultrasound transducer was placed by an expert using the robotic arm for B-mode imaging, and then the positions of the pillars were compared with the B-mode image and 3D CAD model in the 3D view of 3D Slicer (FIGS. 32A and 32B). This procedure was repeated for the 5 pillars. FIG. 32A illustrates an image of positioning an ultrasound transducer for B-mode imaging, and FIG. 32B illustrates a view in 3D slicer corresponding to the setup in FIG. 32A.

For the first experiment, B-mode images were acquired after positioning the ultrasound transducer to locate each of the five pillars on the phantom Annotated screenshots of the Photoacoustic Assistant module (e.g., the 3D view from 3D Slicer) are shown in FIG. 34A. FIG. 34A illustrates a photoacoustic assistant module with real-time B-mode imaging capabilities. Here, the error between the B-mode image and the phantom model is visually apparent. The distance errors were computed between the pillars identified in the B-mode images and the corresponding positions in the 3D CAD model. This computation was performed in the DRB reference frame. Thus, the pillar positions in the B-mode images required the following three transformations: (1) ultrasound probe calibration, (2) ultrasound marker frame to tracking camera, and (3) tracking camera to DRB marker frame. The ground-truth positions (from the 3D CAD model) were transformed using the registration between the CAD model and the DRB, and thus are subject to registration error; however, this is small due to the use of multiple fiducials and the high accuracy of the CAD model. The results (Table II) show a mean accuracy of 0.97 mm for the overall system, which verifies the accuracy of the US probe calibration, tracking system, and registration between CAD model and DRB. Note that this experiment does not verify the accuracy of the tool tip or laser line calibration, since these do not affect the B-mode images.

TABLE II

| DISTANCE BETWEEN GROUND TRUTH AND B-MODE IMAGE | |
|---|---|
| US Target # | Error, mm |
| 1 | 1.631 |
| 2 | 0.865 |
| 3 | 0.902 |
| 4 | 0.866 |
| 5 | 0.563 |
| Mean | 0.966 |

For the second experiment, the ultrasound transducer and laser tip were placed using the visual guidance information of the 3D view of 3D Slicer (FIGS. 33A and 33B). FIG. 33A illustrates an image of positioning an ultrasound transducer and laser tip for photoacoustic imaging and FIG. 33B illustrates an image of a 3D slicer according to FIG. 33A. Subsequently, photoacoustic and B-mode ultrasound images were acquired. These procedures were performed for the two spherical rubber targets.

For each target in the second experiment, the ultrasound transducer and laser tip were positioned with visual guidance of the photoacoustic assistant system and photoacoustic and B-mode images were acquired (see FIG. 35). FIG. 34B illustrates images of the visual guidance interface with real-time photoacoustic images and models of the laser tip and laser path. This figure shows that the real-time photoacoustic image plane and virtual laser path are close to the targets, though small errors are evident. The B-mode images were acquired to give additional insight into the content of the PA images, as shown in FIG. 35 and are not used in the subsequent data analysis. FIG. 35 illustrates photoacoustic image results for two targets: B-mode images (top), photoacoustic images (middle), and photoacoustic images overlaid on B-mode images (bottom); circles indicate target.

The translation vector is computed from the laser tip to the target position using the three methods proposed above (technically, the vector preferably forms from the tool tip to the target, but for these experiments the tool tip is identical to the laser tip; in general, there would be a known offset). For more intuitive understanding, the results are expressed in the coordinate frame of the US image, where the US image plane is approximately orthogonal to the laser line. FIG. 36 illustrates a graphical view of the measurements expressed in the US image plane (i.e., lateral and axial directions) for photoacoustic and navigational methods. Units are in mm. Relative to each other, the methods produce similar results in the lateral direction, with a larger discrepancy in the axial direction. The elevational error (i.e., perpendicular to the image plane) is identical for the two methods because they are both restricted to the US image plane.

Table III compares each measurement to the ground-truth, obtained by applying the registration transformation to the target positions from the CAD model.

TABLE III

ERROR IN MEASURED TARGET POSITION FOR PHOTOACOUSTIC AND INTERSECTION/NAVIGATION, COMPARED TO GROUND-TRUTH. UNITS ARE MM

| PA Target # | Intersection (Nav) | | Photoacoustic | | (Both) |
|---|---|---|---|---|---|
| | Lateral | Axial | Lateral | Axial | Elevational |
| 1 | 0.12 | 0.32 | 0.7 | −1.99 | 0.079 |
| 2 | −0.92 | −0.16 | 0.11 | −2.74 | 1.332 |

This study focused on the development and experimental evaluation of a navigation system to guide the placement of a laser and/or ultrasound probe to obtain photoacoustic images during endonasal skull base drilling. The ultimate goal is to use the photoacoustic images to provide realtime measurement of the location of critical structures, such as the carotid artery, with respect to the tool tip. In one envisioned scenario, the laser and tool are mounted on a robot system which can use this information to dynamically construct or adjust virtual fixtures to protect the critical anatomy. In this case, the navigation system would primarily be used to position the ultrasound probe, though it could also provide guidance to the surgeon (or robot) to make minor adjustments to the tool (and thereby laser) orientation to gain additional image information.

The experiments demonstrated that the developed navigation system is effective in enabling the user to align the laser and probe to obtain a photoacoustic image of a desired target. Here, the target is identified on a 3D CAD model, which is registered to the intraoperative (tracker) coordinate system to provide a ground-truth measurement. The results in Table III indicated that the mean error of the real-time measurement of the distance between the laser tip and the target is less than 1 mm when the proposed method (Intersection/Navigation) is used; this method relies on the accuracy of the laser line calibration with respect to the tool and only uses the tracked US probe to determine the distance from the tip to the image plane. The US image is primarily used as a binary flag to indicate whether or not the target is in the path of the laser. In reality, the situation is more complex due to the use of an uncollimated fiber, which causes significant divergence of the laser beam. The fiber used in these experiments has a numerical aperture of 0.37, which corresponds to a half-angle of approximately 16 degrees in water. At the fiber-to-target distances used in these experiments (≈17 mm for PA Target #1 and ≈20 mm for PA Target #2), the initial 1 mm laser beam diameter diverges to diameters of ≈10.75 mm and ≈12.47 mm, respectively. Thus, the low errors in the lateral and axial directions shown in Table III for the Intersection (Nav.) measurement actually reflect good accuracy in the navigation system, which enabled the user to align the laser beam with the target.

The relatively large error in the axial direction for the photoacoustic method may be due to several other factors, since this measurement is affected by errors in the probe calibration and tracking system, as well as by physical phenomenon such as a system bulk delay offset, which is the time difference between the start of a normal transmit event and actual laser firing time. Assuming the speed of sound in water is 1460 m/s, if the system bulk delay is 2 µs, an offset of 2.92 mm is expected, which is comparable to the measured offsets in Table III. With the phantom modified to place real bone between the laser tip and target and the ultrasound transducer and target, a photoacoustic signal should be obtained from both the target and the bone adjacent to the laser tip. If so, the US probe can be positioned so that the image captures both measurements, enabling for direct measurement of the distance between the tool tip (assuming it is in contact with the bone, e.g., during drilling) and the target. This would remove any dependency on the tracking accuracy of the US probe. If, however, a photoacoustic signal is not obtained from the bone, the experiments reported in herein indicate that accuracy on the order of 1 mm is achievable with the system of the present invention.

In another exemplary embodiment, The penetration of light through the sphenoid bone and hence the quality of resulting photoacoustic images is expected to improve as the sphenoid bone is removed, given the proportional relationships between optical transmission through bone, laser fluence incident on underlying vessels, and photoacoustic signal amplitude. However, to the authors' knowledge, no experimental studies directly measure these relationships. The purpose of this work is to quantify the expected improvements in signal contrast and optical penetration as bone thickness decreases due to the drilling process, with additional applicability to identifying candidates for more general transcranial photoacoustic imaging based on skull thickness.

A plastisol phantom was fabricated with no optical or acoustic scatterers to isolate effects due to the presence of bone. A 3 mm diameter hole was drilled into the phantom and a black, cylindrical rubber target with a diameter of 3.5 mm was inserted into the hole. This target was chosen for its similar diameter to the internal carotid artery and to achieve an optical absorption at least an order of magnitude greater than bone (similar to blood). The target is not expected to significantly vary with wavelength in order to separate the effects of bone penetration from blood absorption as a function of wavelength.

A human frontal skull bone was cut into seven 3 cm×3 cm specimens and sanded to thicknesses ranging from 1.00-4.00 mm, as shown in FIGS. 37A and 37B. FIGS. 37A and 37B illustrate images of a skull bone sanded to the thickness indicated above each image and the experimental setup, respectively. A slit was cut approximately 1 cm from vessel and the skull specimens were individually placed in the slit to obstruct the optical path, as shown in FIG. 37B. Light was transmitted from the 5-mm diameter optical fiber bundle coupled to a combined Nd:YAG laser and optical parametric oscillator (OPO) system (Phocus InLine, Opotek, Carlsbad, Calif.) which tuned the wavelength from 700 nm to 940 nm, in 20 nm increments. An Ultrasonix L14-5W/60 linear transducer with a bandwidth of 5-14 MHz was placed with the long axis of the vessel perpendicular to the axial dimension of the probe. The transducer was connected to a SonixTouch ultrasound scanner, and a SonixDAQ data acquisition unit was triggered by the flashlamp output signal of the laser to access raw, pre-beamformed radiofrequency photoacoustic data.

Photoacoustic images were reconstructed with a delay-and-sum beamformer and the resulting contrast was measured using Eq. 3 where Si and So are the means of the image data within regions of interest (ROIs) located inside and outside of the target, respectively, and $\sigma_o$ is the standard deviation of the data within the ROI located outside of the target. ROIs were defined by searching for the maximum signal within the expected signal location, surrounding this signal with a rectangle, and automatically creating a same-sized noise ROI at the same depth to the right of the signal ROI. Contrast measurements were averaged over five independent acquisitions.

The contrast loss due to the placement of bone, $C_{loss}$, was measured as follows:

$$C_{loss} = \left(1 - \frac{c_b}{c_0}\right) * 100\% \tag{10}$$

where $C_0$ is the contrast when no bone was placed and $C_b$ is the contrast when one of the bone specimens were present. All image processing and data analyses were performed with Matlab software (The MathWorks, Natick, Mass.).

The average energy per pulse was recorded with and without the bone inserted between the fiber and energy meter (NOVA, Ophir, Jerusalem, Israel) as the wavelength of laser was tuned from 700 nm to 940 nm, in increments of 20 nm. A 5 mm diameter fiber bundle delivered the light with an average pulse energy that varied between 6.3 mJ and 14.5 mJ with each wavelength. Transmission was calculated as the ratio between the energy measurements before insertion of the bone to that measured after bone insertion. This ratio was multiplied by 100 to report optical transmission as a percentage and converted to insertion loss measurements through the expression:

$$\text{Insertion Loss} = (1 - \text{Transmission Ratio}) * 100\% \tag{11}$$

A one-layer tissue model with the average wavelength-dependent optical properties for skull bone, as listed in Table IV, was used to estimate optical transmission through bone with a Monte Carlo simulation package. The bone's thickness was varied between 0.5-4 mm in increments of 0.5 mm (which is within the range of sphenoid bone thickness), the wavelength was varied between 700-940 nm, and the refractive index was held constant at 1.56. The top and bottom ambient media were modeled as air with a refractive index of 1. The related optical insertion loss was calculated using Eq. 3. The parameters in Table IV were additionally adjusted within the error of reported measurements to find the best fit with the experimental data.

TABLE IV

Simulation parameters for absorption, a (cm$^{-1}$), scattering, s (cm$^{-1}$), and anisotropy factor (g)

| Wavelength (nm) | 700 | 720 | 740 | 760 | 780 | 800 | 820 | 840 | 860 | 880 | 900 | 920 | 940 |
|---|---|---|---|---|---|---|---|---|---|---|---|---|---|
| $\mu_a$ | 0.24 | 0.23 | 0.24 | 0.25 | 0.245 | 0.245 | 0.25 | 0.26 | 0.27 | 0.29 | 0.33 | 0.38 | 0.43 |
| $\mu_s$ | 333 | 326 | 320 | 313 | 306 | 300 | 293 | 286 | 280 | 273 | 266 | 260 | 253 |
| g | 0.932 | 0.935 | 0.936 | 0.937 | 0.938 | 0.938 | 0.938 | 0.939 | 0.939 | 0.940 | 0.941 | 0.943 | 0.944 |

FIG. 38 shows sample photoacoustic images of the target in FIG. 37B, taken with 800 nm wavelength (13.1 mJ per pulse) in the presence of the bone thicknesses indicated above each image and when no bone was present (0 mm), representing the changes in vessel contrast that would be observed as the sphenoid bone is drilled. Only the proximal and distal boundaries of the 3.5 mm diameter vessel are visible in these images. In addition, the signal appears less diffuse as bone thickness decreases.

Optical transmission measurements are shown as a function of bone thickness in FIG. 39A for both simulation and experimental measurements. In addition to the values reported in Table IV, the optical parameters were adjusted to obtain a "best fit" for all thicknesses ($\mu_s$=280 cm$^{-1}$; g=0:948) as well as an "upper limit" (i.e. max in FIG. 39A) based on the error reported in previous measurements ($\mu_s$=270 cm$^{-1}$; g=0:948). FIGS. 39A and 39B illustrate graphical views of optical transmission rate due to bones of varying thicknesses and varying laser wavelengths respectively, as measured with Monte Carlo simulations and experimental results. The optical parameters reported in Table IV were additionally adjusted in FIG. 39A to obtain the best fit with experimental data as a function of thickness and the maximum optical transmission. Error bars indicate±one standard deviation of three independent measurements for each wavelength and thickness, respectively.

With these adjustments, the simulation and experimental measurements differ by up to 5%. Note the measured transmission decreases up to 30% with increased thickness, a primary factor causing the poor image contrast observed with increased bone thickness in FIG. 38.

The simulation results in FIG. 39B show optical transmission measurements as a function of laser wavelength for experimental measurements and simulation results based on the parameters reported in Table IV. Contrary to variations as a function of bone thickness, the optical transmission increases by less than 4% as the wavelength is varied, indicating that the change in bone thickness would have a greater effect on image contrast than the change caused by different laser wavelengths, particularly within the 700-940 nm range. For all wavelengths investigated, the mean optical transmission through the specimens increased from 19% to 44% as bone thickness decreased from 4 mm to 1 mm.

Photoacoustic signal contrast is quantified as a function of bone thickness in FIG. 40A for laser wavelengths of 700 and 800 nm. Each data point shows the mean one standard deviation of five independent acquisitions. A majority of the changes in contrast occur for bone thicknesses less than or equal to 2 mm, which corresponds to measured transmission ratios greater than or equal to 30%. Poor target visibility (e.g. contrast) was observed at wavelengths of 700 nm (FIG. 40A and 920 nm (not shown), thus the data from these measurements were not included in subsequent analyses. FIGS. 40A and 40B illustrate graphical views of contrast of the photoacoustic signal as a function of bone thickness and a laser wavelength, respectively for the wavelengths or bone thicknesses indicated in the legends of each plot. Error bars indicate±one standard deviation of three independent measurements for each wavelength and thickness, respectively.

Contrast is shown as a function of wavelength in FIG. 40B for bone thicknesses of 0 mm (i.e. no bone), 1 mm, and 2 mm. The photoacoustic signal contrast was normalized for changes in laser energy as a function of wavelength, thus the contrast results for no bone depict the optical absorption spectra differences of the rubber target. When bone is present, contrast is increased by up to 20 dB as wavelength increases, which may be due to the increased absorption of the target or the increased optical penetration through bone (FIG. 39B).

The measured contrast loss as a function of bone thickness is shown in FIG. 41A. The gray lines show individual means for each wavelength and black lines shown mean results for all wavelengths one standard deviation. Note that the combination of all wavelengths (i.e. the black line) reduces the variations in the measurements for each wavelength (i.e. the gray lines). With this combination of spectroscopic information, it is clear that contrast loss increases with thickness and appears saturated when the thickness is greater than or equal to 2 mm. FIG. 41A illustrates a graphical view of loss in contrast relative to the signal with no bone with gray lines showing individual means for each wavelength and black lines showing mean results for all wavelengths±one standard deviation. FIG. 41B illustrates a graphical view of mean contrast loss vs. mean optical insertion loss over 720-940 nm wavelengths with gray points showing measurements for each wavelength for 1, 1.5, and 2 mm bone thicknesses, black points showing the mean values for all wavelengths and all thicknesses (1, 1.5 and 2.0 mm thicknesses are noted next to the corresponding points), and vertical and horizontal error bars representing±one standard deviation.

FIG. 41B directly relates contrast loss to insertion loss. For 56%, 66%, and 70% mean optical insertion loss (i.e. 1, 1.5, and 2 mm bone thickness, respectively) the mean contrast loss is 46%, 64%, and 75%, respectively. The errorbars show standard deviation and span 10-13% and 1-2% for the contrast loss and insertion loss measurements, respectively. A large component of this variation (e.g. up to 4% or 20 dB, respectively) is caused by the combination of all wavelengths. Nonetheless, this combination reduces variations in the measurements, revealing that changes in optical transmission are proportional to changes in image contrast, with scaling factors that range from 0.8 to 1.1, particularly when the bone thickness is less than or equal to 2 mm.

The expected relationships between optical transmission, bone thickness, and photoacoustic image contrast were confirmed, particularly for bone thicknesses of 2 mm or less. When the measured insertion loss was greater than 70% (i.e. less than 30% optical transmission, which corresponds with the 2.0 mm bone thickness), changes in contrast were subtle to nonexistent, likely because of anatomical variability, insufficient fluence to generate a photoacoustic signal, or low-amplitude signals that are difficult to detect with delay-and-sum beamforming. The latter challenge may be overcome with coherence based beamforming, which might be the preferred method for vessel visualization when more than 2 mm of bone remains to be drilled. Otherwise, with an amplitude-based beamformer like delay-and-sum, the contrast of photoacoustic signals increases with decreasing bone thickness.

The work herein extends previous measurements to a larger range of bone thicknesses. For the same wavelength range, the optical transmission through human adult skulls of thickness 1-4 mm is expected to increase from 14 to 49% as thickness decreases, with up to 5% deviation from expected values. This information may be used to identify successful candidates for transcranial imaging based solely on skull thickness.

Acoustic scattering and the presence of temporal bone between the transducer and phantom would reduce the final optical transmission measurements. Nonetheless, the presented experiments were designed to minimize the acoustic effects of transcranial photoacoustic imaging, which has been studied previously for human adult skulls with reports of approximately 0-40 dB acoustic insertion loss. In addition, the contrast loss relative to an initial measurement from the same acoustic environment, as illustrated in FIG. 41A, is not expected to be affected by the presence of temporal bone.

A key finding from this work is the 0.8-1.1 scaling factor between contrast loss and optical insertion loss measurements for bone thicknesses of 2 mm or less when the mean of all wavelengths is considered. Otherwise, if contrast is relatively constant as bone is drilled, surgeons may assume that more than 2 mm of bone remains. The expected mean contrast change in photoacoustic signals due to drilling can potentially be predicted using the proposed spectroscopic approach if the optical transmission through bone and an initial bone thickness (determined from preoperative CT or MR images) are known. The patient-specific optical transmission could potentially be provided by analyzing the initial specimens of sphenoid bone removed during an operation. If this type of analysis is unavailable (e.g. if the initial thickness of the sphenoid bone is 2 mm or less), Monte Carlo simulations may be utilized with an approximate 5% maximum deviation between simulated and measured optical transmission, based on the results presented in FIG. 39A. A contrast loss prediction that relies on either method may then be correlated with actual intraoperative contrast loss measurements to determine the amount of bone that remains to be drilled, which is the focus of future work.

The proportional relationships between photoacoustic image contrast, bone thickness (2 mm), and optical penetration were quantified with a spectroscopic approach that combines measurements from multiple wavelengths (720-940 nm). The scaling factor between contrast loss and insertion loss is 0.8-1.1 for bone thicknesses less than or equal to 2 mm and is relatively constant for greater thicknesses due to minimal changes in image contrast. Results additionally demonstrate that the optical penetration through human adult skull bone of thickness 1 mm to 4 mm is 50% to 15%, respectively. This work lays the foundation for determining the amount of bone that remains to be drilled by monitoring image contrast during endonasal transsphenoidal surgeries.

In another embodiment, FIG. 42 illustrates an image of Photoacoustic system for finding vessels for intravaneous (IV) treatments. Light is transmitted through a fiber attached to a conventional needle for drawing blood and sound is received by a finger ultrasound probe. Applications include finding vessels for administering chemotherapy, performing biopsies, delivering drugs, and establishing IV access in critically ill pediatric patients=. The system in the embodiment shown in FIG. 42 or in any of the other embodiments disclosed herein could also be used to differentiate arteries from veins with oxygen saturation measurements.

Alternatively, the fiber and probe may be integrated into the needle. The probe could be a small piezoelectric element or it could be an optical fiber with a Fabry-Perot interferometer (i.e. all-optical photoacoustic imaging). Whether integrated with or separated from the probe, the needle can house a display read-out that indicates: (1) the maximum strength of the PA signal to determine proximity to the vessel; (2) an image of the vessels; (3) the suggested direction for achieving a better signal; (4) a map of the signal strength history to aid in returning to the location where the signal was strongest (which indicates where the vessel is located); (5) oxygen saturation. This display may also be separated from the needle (although probably less convenient for the user). An embodiment of this display is illustrated in FIG. 43.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for photoacoustic imaging during a surgical or interventional procedure comprising:
   an acoustic sensor positioned on a patient at or near a site of the surgical or interventional procedure;
   an electromagnetic source configured to produce electromagnetic waves;
   one or more optical fibers coupled to the electromagnetic source,
      the one or more optical fibers for illuminating the site of the surgical or interventional procedure with the electromagnetic waves;
   a surgical or interventional tool configured for the surgical or interventional procedure,
      the one or more optical fibers being coupled to the surgical or interventional tool,
      the one or more optical fibers being positioned to illuminate the site of the surgical or interventional procedure with the electromagnetic waves,
      the one or more optical fibers to illuminate one or more structures within a body,
         the one or more structures including at least one of:
            at least one blood vessel, or
            bone,
      the one or more optical fibers including multiple fibers,
         the multiple fibers being disposed around a circumference of the surgical or interventional tool, and
         one or more optical beams associated with the multiple fibers being oriented in an illumination pattern, and
   the acoustic sensor being separate from the surgical or interventional tool; and one or more processors to:
   receive photoacoustic image data from the acoustic sensor;
   apply a short-lag spatial coherence beamformer to the photoacoustic image data,
      the short-lag spatial coherence beamformer being determined based upon:
         calculating a spatial correlation, and
         integrating the spatial correlation as a function of transducer element separation to determine a pixel in a line of a beamformed image,
      the short-lag spatial coherence beamformer being optimized based upon a shape of the illumination pattern of the one or more optical beams of the multiple fibers, and
      the illumination pattern being optimized to enhance visualization with the short-lag spatial coherence beamformer; and
   generate a display of the photoacoustic image data after the short-lag spatial coherence beamformer is applied.

2. The system for photoacoustic imaging of claim 1, wherein the one or more processors are further configured to:
   receive data from the one or more optical fibers.

3. The system for photoacoustic imaging of claim 1, further comprising:
   a robot to control at least one of:
      the surgical or interventional tool,
      the one or more optical fibers, or
      the acoustic sensor.

4. The system for photoacoustic imaging of claim 1, wherein the acoustic sensor is configured to acquire B-mode images.

5. The system of claim 1, wherein the one or more processors are further configured to:
   generate photoacoustic image quality and performance metrics,
      the photoacoustic image quality and performance metrics being used to provide information associated with guiding the surgical or interventional procedure.

6. The system of claim 1, wherein the one or more optical fibers are integrated with the acoustic sensor.

7. The system of claim 1, wherein the one or more optical fibers are separate from the acoustic sensor.

8. The system of claim 1, wherein a photoacoustic device is configured to acquire ultrasound images.

9. The system for photoacoustic imaging of claim 1, wherein the display of the photoacoustic image data includes a spatial coherence of the photoacoustic image independent of an amplitude of the photoacoustic image.

10. The system of claim 1, wherein a shape of a fiber tip of the one or more optical fibers is modified to increase a surface area of the fiber tip.

11. A system for photoacoustic imaging comprising:
   a tracking device, comprising:
      an optical fiber,
         the optical fiber being positioned to illuminate a site of a surgical or an interventional procedure with electromagnetic waves,
      one or more optical beams associated with the optical fiber being oriented in an illumination pattern,
      the optical fiber to illuminate one or more structures within a body, the one or more structures including at least one of:
    at least one blood vessel, or
    bone,
a medical device, and
a laser,
the tracking device being configured to generate tracking data;
a photoacoustic device,
    the photoacoustic device being configured to generate photoacoustic image data,
    the photoacoustic device being separate from the medical device; and
one or more processors to:
    receive the tracking data and the photoacoustic image data,
    apply a short-lag spatial coherence beamformer to the photoacoustic image data,
        the short-lag spatial coherence beamformer being determined based upon:
            calculating a spatial correlation, and
            integrating the spatial correlation as a function of transducer element separation to determine a pixel in a line of a beamformed image,
        the short-lag spatial coherence beamformer being optimized based upon a shape of the illumination pattern of the one or more optical beams of the optical fiber, and
        the illumination pattern being optimized to enhance visualization with the short-lag spatial coherence beamformer, and
    generate a display of the tracking data and the photoacoustic image data after the short-lag spatial coherence beamformer is applied.

12. The system of claim 11 wherein the photoacoustic device is configured to acquire ultrasound images.

13. The system of claim 11 further comprising:
a robot to control at least one of:
    the medical device,
    the photoacoustic device, or
    the optical fiber.

14. The system of claim 13 wherein the robot is coupled to the medical device, optical fiber, and/or the laser.

15. The system of claim 11, wherein the one or more processors are further configured to:
generate photoacoustic image quality and/or performance metrics,
    the photoacoustic image quality and/or performance metrics being used to provide information associated with guiding a surgical or interventional procedure.

16. The system of claim 11, wherein the display of the photoacoustic image data includes a spatial coherence of the photoacoustic image independent of an amplitude of the photoacoustic image.

17. A system, comprising:
an acoustic sensor configured to receive photoacoustic image data;
a laser configured to produce electromagnetic waves;
one or more optical fibers coupled to the laser,
    the one or more optical fibers configured to illuminate a site of a medical procedure with the electromagnetic waves,
    the one or more optical fibers being coupled to a medical tool,
    the one or more optical fibers being disposed within the medical tool,
    one or more optical beams associated with the one or more optical fibers being oriented in an illumination pattern, and
    the acoustic sensor being separate from the medical tool; and
one or more processors configured to:
    receive the photoacoustic image data from the acoustic sensor;
    apply a short-lag spatial coherence beamformer to the photoacoustic image data,
        the short-lag spatial coherence beamformer being determined based upon:
            calculating a spatial correlation, and
            integrating the spatial correlation as a function of transducer element separation to determine a pixel in a line of a beamformed image; and
    generate a display of the photoacoustic image data after the photoacoustic image data has been processed by the short-lag spatial coherence beamformer.

18. The system of claim 17, wherein the one or more optical fibers are separate from the acoustic sensor.

19. The system of claim 17, wherein the one or more optical fibers are integrated with the acoustic sensor.

20. The system of claim 17, further comprising:
a robot to control at least one of:
    the medical tool,
    the one or more optical fibers, or
    the acoustic sensor.

21. The system of claim 11, wherein the optical fiber is separate from the medical device.

* * * * *